United States Patent
Owens Merlo et al.

(10) Patent No.: US 9,909,133 B2
(45) Date of Patent: Mar. 6, 2018

(54) ROOT SPECIFIC EXPRESSION CONFERRED BY CHIMERIC GENE REGULATORY ELEMENTS

(71) Applicant: Dow AgroSciences LLC, Indianapolis, IN (US)

(72) Inventors: Patricia Ann Owens Merlo, Carmel, IN (US); Ronnie Hampton, Jr., Indianapolis, IN (US); Cory Larsen, Zionsville, IN (US); Aaron Woosley, Fishers, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 236 days.

(21) Appl. No.: 14/632,553

(22) Filed: Feb. 26, 2015

(65) Prior Publication Data

US 2015/0247155 A1 Sep. 3, 2015

Related U.S. Application Data

(60) Provisional application No. 61/946,066, filed on Feb. 28, 2014.

(51) Int. Cl.
| | |
|---|---|
| *C12N 15/82* | (2006.01) |
| *C12N 15/113* | (2010.01) |
| *C07K 14/415* | (2006.01) |

(52) U.S. Cl.
CPC ........ *C12N 15/8227* (2013.01); *C12N 15/113* (2013.01); *C12N 15/8286* (2013.01); *C07K 14/415* (2013.01)

(58) Field of Classification Search
None
See application file for complete search history.

(56) References Cited

U.S. PATENT DOCUMENTS

| | | | |
|---|---|---|---|
| 6,590,142 B1 * | 7/2003 | Petell | C07K 14/24 435/418 |
| 2004/0143868 A1 * | 7/2004 | Ainley | C12N 9/0065 800/278 |

OTHER PUBLICATIONS

Kim et al. A 20 nucleotide upstream element is essential for the nopaline synthase (nos) promoter activity. Plant Molecular Biology. 1994. 24: 105-117.*
Kennell. Principles and practices of nucleic acid hybridization. Progress in Nucleic Acid Research and Molecular Biology. 1971. 11: 259-301.*
Maniatis et al. Molecular cloning: a laboratory manual. Cold Spring Harbor Laboratory. 1982. pp. 324-343 and 387-389.*

* cited by examiner

*Primary Examiner* — Ashley K Buran
(74) *Attorney, Agent, or Firm* — Ronald S. Maciak; Barnes & Thornburg LLP

(57) ABSTRACT

Provided are constructs and methods for expressing a transgene in plant cells and/or plant tissues using chimeric gene regulatory elements.

13 Claims, No Drawings

ROOT SPECIFIC EXPRESSION CONFERRED BY CHIMERIC GENE REGULATORY ELEMENTS

CROSS-REFERENCE TO RELATED APPLICATIONS

This application claims the benefit under 35 USC § 119(e) of U.S. Provisional Application Ser. No. 61/946,066, filed on Feb. 28, 2014, which is expressly incorporated herein by reference.

REFERENCE TO SEQUENCE LISTING SUBMITTED ELECTRONICALLY

The official copy of the sequence listing is submitted electronically via EFS-Web as an ASCII formatted sequence listed with a filed named "68242_ST25.txt", created on Feb. 26, 2015, and having a size of 49.7 kilobytes and is filed concurrently with the specification. The sequence listing contained in the ASCII formatted document is part of the specification and is herein incorporated by reference in its entirety.

FIELD OF THE INVENTION

This invention is generally related to the field of plant molecular biology, and more specifically, to the field of expression of transgenes in plants.

BACKGROUND

Many plant species are capable of being transformed with transgenes to introduce agronomically desirable traits or characteristics. Plant species are developed and/or modified to have particular desirable traits. Generally, desirable traits include, for example, improving nutritional value quality, increasing yield, conferring pest or disease resistance, increasing drought and stress tolerance, improving horticultural qualities (e.g., pigmentation and growth), imparting herbicide resistance, enabling the production of industrially useful compounds and/or materials from the plant, and/or enabling the production of pharmaceuticals.

Transgenic plant species comprising multiple transgenes stacked at a single genomic locus are produced via plant transformation technologies. Plant transformation technologies result in the introduction of a transgene into a plant cell, recovery of a fertile transgenic plant that contains the stably integrated copy of the transgene in the plant genome, and subsequent transgene expression via transcription and translation of the plant genome resulting in transgenic plants that possess desirable traits and phenotypes. However, mechanisms that allow the production of transgenic plant species to highly express multiple transgenes engineered as a trait stack are desirable.

Likewise, mechanisms that allow the expression of a transgene within particular tissues or organs of a plant are desirable. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene in plant tissues that are in a particular growth or developmental phase such as, for example, cell division or elongation.

Described herein are chimeric promoter regulatory elements (e.g., promoter sequences comprising upstream promoters, introns, and 5'-UTRs). Further described are constructs and methods utilizing chimeric promoter regulatory elements.

SUMMARY

Disclosed herein are constructs and methods for expressing a transgene in plant cells and/or plant tissues. In an embodiment, a construct includes a gene expression cassette comprising a chimeric polynucleotide sequence comprising an upstream-promoter polynucleotide sequence that was obtained from Zea mays Peroxidase 5 and followed by the Zea mays alcohol dehydrogenase (I) intron 6 and Maize Streak Virus 5'-UTR. The resulting chimeric promoter sequence comprises a novel chimeric gene regulatory element.

In an embodiment, a gene expression cassette includes a chimeric gene promoter regulatory element operably linked to a transgene or a heterologous coding sequence. In an embodiment, a gene expression cassette includes at least one, two, three, four, five, six, seven, eight, nine, ten, or more transgenes.

Methods of growing plants expressing a transgene using a chimeric gene promoter regulatory element (e.g., upstream-promoter, intron, and 5'-UTR) are disclosed herein. Methods of culturing plant tissues and cells expressing a transgene using the chimeric gene promoter regulatory element are also disclosed herein. In an embodiment, methods as disclosed herein include tissue-specific gene expression in plant roots. Methods of isolating a polynucleotide sequence comprising the chimeric gene promoter regulatory element are also disclosed herein.

In an embodiment, the subject disclosure relates to a gene expression cassette comprising a promoter operably linked to a transgene, wherein the promoter comprises a polynucleotide that hybridizes under stringent conditions to a polynucleotide probe comprising a sequence identity of at least 90% to a complement of SEQ ID NO:1. In an subsequent aspect of the embodiment, the polynucleotide has at least 90% sequence identity to SEQ ID NO:1. In other aspects, the operably linked transgene encodes a polypeptide or a small RNA. In yet further aspects, the transgene is selected from the group consisting of an insecticidal resistance transgene, a herbicide tolerance transgene, a nitrogen use efficiency transgene, a water use efficiency transgene, a nutritional quality transgene, a DNA binding transgene, and a selectable marker transgene. In an aspect, the embodiment relates to a gene expression cassette comprising a 3'-untranslated region. In an embodiment, the subject disclosure relates to a recombinant vector comprising the gene expression cassette. In an aspect of the embodiment, the vector is selected from the group consisting of a plasmid, a cosmid, a bacterial artificial chromosome, a virus, and a bacteriophage. In other embodiments, the subject disclosure relates to a transgenic cell comprising the gene expression cassette. In another embodiment, the transgenic cell is a transgenic plant cell. In a further embodiment, the subject disclosure relates to a transgenic plant comprising the transgenic plant cell. In an aspect of the embodiment, the transgenic plant is a monocotyledonous or a dicotyledonous plant. In other aspects, the monocotyledonous plant is selected from the group consisting of a maize plant, a rice plant, and a wheat plant. In a further embodiment, the disclosure relates to a transgenic seed from the transgenic plant. In another embodiment, the promoter is a tissue-preferred promoter. In a subsequent embodiment, the tissue-preferred promoter is a root tissue-preferred promoter.

In an embodiment, the subject disclosure relates to a transgenic cell comprising a synthetic polynucleotide that hybridizes under stringent conditions to a polynucleotide probe comprising a sequence identity of at least 90% to a complement of SEQ ID NO:1. In an aspect of the embodiment, the polynucleotide has at least 90% sequence identity to SEQ ID NO:1. In a further aspect of the embodiment, the transgenic cell is a transgenic plant cell. In another aspect, the transgenic plant cell is produced by a plant transformation method. In other aspects, the plant transformation method is selected from the group consisting of an *Agrobacterium*-mediated transformation method, a biolistics transformation method, a silicon carbide transformation method, a protoplast transformation method, and a liposome transformation method. In a further embodiment, the subject disclosure relates to a transgenic plant comprising the transgenic plant cell. In an aspect of the embodiment, the transgenic plant is a monocotyledonous or a dicotyledonous plant. In other aspects, the monocotyledonous plant is selected from the group consisting of a maize plant, a rice plant, and a wheat plant. In further embodiments, the subject disclosure relates to a transgenic seed from the transgenic plant. In an additional embodiment, the promoter is a tissue-preferred promoter. In further embodiments, the tissue-preferred promoter is a root tissue-preferred promoter.

In an embodiment, the subject disclosure relates to a chimeric polynucleotide sequence that hybridizes under stringent conditions to a polynucleotide probe comprising a sequence identity of at least 90% to a complement of SEQ ID NO:1. In another aspect of the embodiment, the polynucleotide has at least 90% sequence identity to SEQ ID NO:1. In a further aspect, the chimeric polynucleotide sequence is operably linked to a transgene. In another aspect, the operably linked transgene encodes a polypeptide or small RNA. In an aspect, the chimeric polynucleotide sequence is operably linked to the transgene. In further aspects, the transgene is selected from the group consisting of an insecticidal resistance transgene, a herbicide tolerance transgene, a nitrogen use efficiency transgene, a water use efficiency transgene, a nutritional quality transgene, a DNA binding transgene, and a selectable marker transgene. In an additional embodiment, the subject disclosure relates to a recombinant vector comprising the gene expression cassette. Further aspects include wherein the vector is selected from the group consisting of a plasmid, a cosmid, a bacterial artificial chromosome, a virus, and a bacteriophage. In an embodiment, the subject disclosure relates to a transgenic cell comprising the gene expression cassette. In other aspects the transgenic cell is a transgenic plant cell. In an embodiment, the subject disclosure relates to a transgenic plant comprising the transgenic plant cell. An additional aspect includes, where the transgenic plant is a monocotyledonous plant. Further aspects include, where the monocotyledonous plant is selected from the group consisting of a maize plant, a wheat plant, and a rice plant. In an embodiment, the subject disclosure relates to a transgenic seed from the transgenic plant. In a further aspect of the embodiment, the chimeric polynucleotide sequence promotes root-preferred expression of a transgene.

In an embodiment, the subject disclosure relates to a method for expressing a heterologous coding sequence in a transgenic plant, the method comprising:
  transforming a plant cell with a gene expression cassette comprising a polynucleotide sequence comprising a sequence identity of at least 90% to SEQ ID NO:1 operably linked to the heterologous coding sequence, which is operably linked to a 3'-untranslated region;
  isolating the transformed plant cell comprising the gene expression cassette;
  regenerating the transformed plant cell into a transgenic plant; and,
  obtaining the transgenic plant, wherein the transgenic plant comprises the gene expression cassette comprising the polynucleotide sequence comprising SEQ ID NO:1.

In an aspect of the embodiment, the heterologous coding sequence is selected from the group consisting of an insecticidal resistance coding sequence, a herbicide tolerance coding sequence, a nitrogen use efficiency coding sequence, a water use efficiency coding sequence, a nutritional quality coding sequence, a DNA binding coding sequence, and a selectable marker coding sequence. In other aspects, the transforming of a plant cell is a plant transformation method. In subsequent aspects, the plant transformation method is selected from the group consisting of an *Agrobacterium*-mediated transformation method, a biolistics transformation method, a silicon carbide transformation method, a protoplast transformation method, and a liposome transformation method. In other aspects, the transgenic plant is a monocotyledonous or dicotyledonous transgenic plant. Further aspects include wherein the monocotyledonous transgenic plant is selected from the group consisting of a maize plant, a wheat plant, and a rice plant. In an embodiment, the subject disclosure relates to a transgenic seed from the transgenic plant. In additional aspects, the heterologous coding sequence is expressed in a transgenic plant tissue. In subsequent aspects, the transgenic plant tissue is a transgenic plant root tissue.

In an embodiment, the subject disclosure relates to a method for isolating a polynucleotide sequence comprising a sequence identity of at least 90% to SEQ ID NO:1, the method comprising:
  identifying the polynucleotide sequence comprising a sequence identity of at least 90% to SEQ ID NO:1;
  producing a plurality of oligonucleotide primer sequences, wherein the oligonucleotide primer sequences bind to the polynucleotide sequence comprising a sequence identity of at least 90% to SEQ ID NO:1;
  amplifying the polynucleotide sequence comprising a sequence identity of at least 90% to SEQ ID NO: 1 from a DNA sample with oligonucleotide primer sequences selected from the plurality of oligonucleotide primer sequences; and,
  isolating the polynucleotide sequence comprising a sequence identity of at least 90% to SEQ ID NO:1.

In another aspect of the embodiment, the isolated polynucleotide sequence comprising a sequence identity of at least 90% to SEQ ID NO:1 is operably linked to a transgene. In a subsequent aspect of the embodiment the operably linked transgene encodes a polypeptide or a small RNA.

The following numbered embodiments are contemplated and are non-limiting:
  1. A gene expression cassette comprising a promoter operably linked to a transgene, wherein the promoter comprises a polynucleotide that hybridizes under stringent conditions to a polynucleotide probe comprising a sequence identity of at least 90% to a complement of SEQ ID NO:1.
  2. The gene expression cassette of clause 1, wherein the polynucleotide has at least 90% sequence identity to SEQ ID NO:1.

3. The gene expression cassette of clause 1, wherein the operably linked transgene encodes a polypeptide or a small RNA.
4. The gene expression cassette of clause 1, wherein the transgene is selected from the group consisting of an insecticidal resistance transgene, a herbicide tolerance transgene, a nitrogen use efficiency transgene, a water use efficiency transgene, a nutritional quality transgene, a DNA binding transgene, and a selectable marker transgene.
5. The gene expression cassette of clause 1 further comprising a 3'-untranslated region.
6. A recombinant vector comprising the gene expression cassette of clause 1.
7. The recombinant vector of clause 6, wherein the vector is selected from the group consisting of a plasmid, a cosmid, a bacterial artificial chromosome, a virus, and a bacteriophage.
8. A transgenic cell comprising the gene expression cassette of clause 1.
9. The transgenic cell of clause 8, wherein the transgenic cell is a transgenic plant cell.
10. A transgenic plant comprising the transgenic plant cell of clause 9.
11. The transgenic plant of clause 10, wherein the transgenic plant is a monocotyledonous or a dicotyledonous plant.
12. The transgenic plant of clause 11, wherein the monocotyledonous plant is selected from the group consisting of a maize plant, a rice plant, and a wheat plant.
13. A transgenic seed from the transgenic plant of clause 10.
14. The gene expression cassette of clause 1, wherein the promoter is a tissue-preferred promoter.
15. The gene expression cassette of clause 1, wherein the tissue-preferred promoter is a root tissue-preferred promoter.
16. A transgenic cell comprising a synthetic polynucleotide that hybridizes under stringent conditions to a polynucleotide probe comprising a sequence identity of at least 90% to a complement of SEQ ID NO:1.
17. The transgenic cell of clause 16, wherein the synthetic polynucleotide has at least 90% sequence identity to SEQ ID NO:1.
18. The transgenic cell of clause 16, wherein the transgenic cell is a transgenic plant cell.
19. The transgenic cell of clause 18, wherein the transgenic plant cell is produced by a plant transformation method.
20. The transgenic cell of clause 19, wherein the plant transformation method is selected from the group consisting of an *Agrobacterium*-mediated transformation method, a biolistics transformation method, a silicon carbide transformation method, a protoplast transformation method, and a liposome transformation method.
21. A transgenic plant comprising the transgenic plant cell of clause 18.
22. The transgenic plant of clause 21, wherein the transgenic plant is a monocotyledonous or a dicotyledonous plant.
23. The transgenic plant of clause 22, wherein the monocotyledonous plant is selected from the group consisting of a maize plant, a rice plant, and a wheat plant.
24. A transgenic seed from the transgenic plant of clause 21.
25. The transgenic cell of clause 16, wherein the promoter is a tissue-preferred promoter.
26. The transgenic cell of clause 16, wherein the tissue-preferred promoter is a root tissue-preferred promoter.
27. A chimeric polynucleotide sequence that hybridizes under stringent conditions to a polynucleotide probe comprising a sequence identity of at least 90% to a complement of SEQ ID NO:1.
28. The chimeric polynucleotide sequence of clause 27, wherein the polynucleotide has at least 90% sequence identity to SEQ ID NO:1.
29. The chimeric polynucleotide sequence of clause 27, wherein the chimeric polynucleotide sequence is operably linked to a transgene.
30. The operably linked transgene of clause 29, wherein the operably linked transgene encodes a polypeptide or small RNA.
31. A gene expression cassette comprising the chimeric polynucleotide sequence operably linked to the transgene of clause 27.
32. The gene expression cassette of clause 31, wherein the transgene is selected from the group consisting of an insecticidal resistance transgene, a herbicide tolerance transgene, a nitrogen use efficiency transgene, a water use efficiency transgene, a nutritional quality transgene, a DNA binding transgene, and a selectable marker transgene.
33. A recombinant vector comprising the gene expression cassette of clause 31.
34. The recombinant vector of clause 33, wherein the vector is selected from the group consisting of a plasmid, a cosmid, a bacterial artificial chromosome, a virus, and a bacteriophage.
35. A transgenic cell comprising the gene expression cassette of clause 31.
36. The transgenic cell of clause 35, wherein the transgenic cell is a transgenic plant cell.
37. A transgenic plant comprising the transgenic plant cell of clause 36.
38. The transgenic plant of clause 37, wherein the transgenic plant is a monocotyledonous plant.
39. The transgenic plant of clause 38, wherein the monocotyledonous plant is selected from the group consisting of a maize plant, a wheat plant, and a rice plant.
40. A transgenic seed from the transgenic plant of clause 37.
41. The chimeric polynucleotide sequence of clause 27, wherein the chimeric polynucleotide sequence promotes root-preferred expression of a transgene.
42. A method for expressing a heterologous coding sequence in a transgenic plant, the method comprising:
a) transforming a plant cell with a gene expression cassette, wherein the gene expression cassette comprises a polynucleotide sequence comprising a sequence identity of at least 90% to SEQ ID NO:1 operably linked to the heterologous coding sequence, which is operably linked to a 3'-untranslated region;
b) isolating the transformed plant cell comprising the gene expression cassette;
c) regenerating the transformed plant cell into a transgenic plant; and,
d) obtaining the transgenic plant, wherein the transgenic plant comprises the gene expression cassette comprising the polynucleotide sequence comprising SEQ ID NO:1.
43. The method of clause 42, wherein the heterologous coding sequence is selected from the group consisting of an insecticidal resistance coding sequence, a herbicide tolerance coding sequence, a nitrogen use efficiency coding sequence, a water use efficiency coding sequence, a nutritional quality coding sequence, a DNA binding coding sequence, and a selectable marker coding sequence.
44. The method of clause 42, wherein transforming a plant cell is a plant transformation method.
45. The method of clause 44, wherein the plant transformation method is selected from the group consisting of an *Agrobacterium*-mediated transformation method, a biolistics transformation method, a silicon carbide transformation method, a protoplast transformation method, and a liposome transformation method.
46. The method of clause 42, wherein the transgenic plant is a monocotyledonous or dicotyledonous transgenic plant.
47. The method of clause 46, wherein the monocotyledonous transgenic plant is selected from the group consisting of a maize plant, a wheat plant, and a rice plant.
48. A transgenic seed from the transgenic plant of clause 42.
49. The method of clause 42, wherein the heterologous coding sequence is expressed in a transgenic plant tissue.
50. The method of clause 42, wherein the transgenic plant tissue is a transgenic plant root tissue.
51. A method for isolating a polynucleotide sequence comprising a sequence identity of at least 90% to SEQ ID NO:1, the method comprising:
a) identifying the polynucleotide sequence comprising a sequence identity of at least 90% to SEQ ID NO:1;
b) producing a plurality of oligonucleotide primer sequences, wherein the oligonucleotide primer sequences bind to the polynucleotide sequence comprising a sequence identity of at least 90% to SEQ ID NO:1;
c) amplifying the polynucleotide sequence comprising a sequence identity of at least 90% to SEQ ID NO: 1 from a DNA sample with oligonucleotide primer sequences selected from the plurality of oligonucleotide primer sequences; and,
d) isolating the polynucleotide sequence comprising a sequence identity of at least 90% to SEQ ID NO:1.
52. The method of clause 51, wherein the isolated polynucleotide sequence comprising a sequence identity of at least 90% to SEQ ID NO:1 is operably linked to a transgene.
53. The method of clause 52, wherein the operably linked transgene encodes a polypeptide or a small RNA.

DETAILED DESCRIPTION

Definitions

As used herein, the articles, "a", "an", and "the" include plural references unless the context clearly and unambiguously dictates otherwise.

As used herein, the term "backcrossing" refers to a process in which a breeder crosses hybrid progeny back to one of the parents, for example, a first generation hybrid F1 with one of the parental genotypes of the F1 hybrid.

As used herein, the term "intron" refers to any nucleic acid sequence comprised in a gene (or expressed nucleotide sequence of interest) that is transcribed but not translated. Introns include untranslated nucleic acid sequence within an expressed sequence of DNA, as well as corresponding sequence in RNA molecules transcribed therefrom.

A construct described herein can also contain sequences that enhance translation and/or mRNA stability such as introns. An example of one such intron is the first intron of gene II of the histone variant of *Arabidopsis thaliana* or any other commonly known intron sequence. Introns can be used in combination with a promoter sequence to enhance translation and/or mRNA stability.

As used herein, the terms "5' untranslated region" or "5'-UTR" refer to an untranslated segment in the 5' terminus of pre-mRNAs or mature mRNAs. For example, on mature mRNAs, a 5'-UTR typically harbors on its 5' end a 7-methylguanosine cap and is involved in many processes such as splicing, polyadenylation, mRNA export towards the cytoplasm, identification of the 5' end of the mRNA by the translational machinery, and protection of the mRNAs against degradation.

As used herein, the term "3' untranslated region" or "3'-UTR" refers to an untranslated segment in a 3' terminus of the pre-mRNAs or mature mRNAs. For example, on mature mRNAs this region harbors the poly-(A) tail and is known to have many roles in mRNA stability, translation initiation, and mRNA export.

As used herein, the term "polyadenylation signal" refers to a nucleic acid sequence present in mRNA transcripts that allows for termination of transcripts, when in the presence of a poly-(A) polymerase, to be polyadenylated on the polyadenylation site, for example, located 10 to 30 bases downstream of the poly-(A) signal. Many polyadenylation signals are known in the art and are useful for the present invention. An exemplary sequence includes AAUAAA and variants thereof, as described in Loke J., et al., (2005) *Plant Physiology* 138(3); 1457-1468.

As used herein, the term "isolated" refers to a biological component (including a nucleic acid or protein) that has been separated from other biological components in the cell of the organism in which the component naturally occurs (i.e., other chromosomal and extra-chromosomal DNA).

As used herein, the term "purified" in reference to nucleic acid molecules does not require absolute purity (such as a homogeneous preparation); instead, it represents an indication that the sequence is relatively more pure than in its native cellular environment (compared to the natural level this level should be at least 2-5 fold greater, e.g., in terms of concentration or gene expression levels). The DNA molecules obtained directly from total DNA or from total RNA. In addition, cDNA clones are not naturally occurring, but rather are preferably obtained via manipulation of a partially purified, naturally occurring substance (messenger RNA). The construction of a cDNA library from mRNA involves the creation of a synthetic substance (cDNA). Individual cDNA clones can be purified from the synthetic library by clonal selection of the cells carrying the cDNA library. Thus, the process which includes the construction of a cDNA library from mRNA and purification of distinct cDNA clones yields an approximately $10^6$-fold purification of the native message. Likewise, a promoter DNA sequence could be cloned into a plasmid. Such a clone is not naturally occurring, but rather is preferably obtained via manipulation of a partially purified, naturally occurring substance such as a genomic DNA library. Thus, purification of at least one order of magnitude, preferably two or three orders, and more preferably four or five orders of magnitude is favored in these techniques.

Similarly, purification represents an indication that a chemical or functional change in the component DNA sequence has occurred. Nucleic acid molecules and proteins that have been "purified" include nucleic acid molecules and proteins purified by standard purification methods. The term "purified" also embraces nucleic acids and proteins prepared by recombinant DNA methods in a host cell (e.g., plant cells), as well as chemically-synthesized nucleic acid molecules, proteins, and peptides.

The term "recombinant" means a cell or organism in which genetic recombination has occurred. It also includes a molecule (e.g., a vector, plasmid, nucleic acid, polypeptide, or a small RNA) that has been artificially or synthetically (i.e., non-naturally) altered by human intervention. The alteration can be performed on the molecule within, or removed from, its natural environment or state.

As used herein, the term "expression" refers to the process by which a polynucleotide is transcribed into mRNA (including small RNA molecules) and/or the process by which the transcribed mRNA (also referred to as "transcript") is subsequently translated into peptides, polypeptides, or proteins. Gene expression can be influenced by external signals, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, the terms "homology-based gene silencing" or "HBGS" are generic terms that include both transcriptional gene silencing and post-transcriptional gene silencing. Silencing of a target locus by an unlinked silencing locus can result from transcription inhibition (transcriptional gene silencing; TGS) or mRNA degradation (post-transcriptional gene silencing; PTGS), owing to the production of double-stranded RNA (dsRNA) corresponding to promoter or transcribed sequences, respectively. Involvement of distinct cellular components in each process suggests that dsRNA-induced TGS and PTGS likely result from the diversification of an ancient common mechanism. However, a strict comparison of TGS and PTGS has been difficult to achieve because it generally relies on the analysis of distinct silencing loci. A single transgene locus can be described to trigger both TGS and PTGS, owing to the production of dsRNA corresponding to promoter and transcribed sequences of different target genes.

As used herein, the terms "nucleic acid molecule", "nucleic acid", or "polynucleotide" (all three terms are synonymous with one another) refer to a polymeric form of nucleotides, which may include both sense and anti-sense strands of RNA, cDNA, genomic DNA, and synthetic forms, and mixed polymers thereof. "A nucleotide" may refer to a ribonucleotide, deoxyribonucleotide, or a modified form of either type of nucleotide. A nucleic acid molecule is usually at least 10 bases in length, unless otherwise specified. The terms may refer to a molecule of RNA or DNA of indeterminate length. The terms include single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" relative to a further element if they are bonded or would be bonded to the same nucleic acid in the 5' direction from that element. Similarly, discrete elements may be "downstream" relative to a further element if they are or would be bonded to the same nucleic acid in the 3' direction from that element.

As used herein, the term "base position" refers to the location of a given base or nucleotide residue within a designated nucleic acid. A designated nucleic acid may be defined by alignment with a reference nucleic acid.

As used herein, the term "hybridization" refers to a process where oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and bonding of a pyrimidine to a purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

As used herein, the terms "specifically hybridizable" and "specifically complementary" refer to a sufficient degree of complementarity such that stable and specific binding occurs between an oligonucleotide and the DNA or RNA target. Oligonucleotides need not be 100% complementary to the target sequence to specifically hybridize. An oligonucleotide is specifically hybridizable when binding of the oligonucleotide to the target DNA or RNA molecule interferes with the normal function of the target DNA or RNA, and there is sufficient degree of complementarity to avoid non-specific binding of an oligonucleotide to non-target sequences under conditions where specific binding is desired, for example under physiological conditions in the case of in vivo assays or systems. Such binding is referred to as specific hybridization. Hybridization conditions resulting in particular degrees of stringency will vary depending upon the nature of the chosen hybridization method and the composition and length of the hybridizing nucleic acid sequences. Generally, the temperature of hybridization and the ionic strength (especially $Na^+$ and/or $Mg^{2+}$ concentration) of a hybridization buffer will contribute to the stringency of hybridization, though wash times also influence stringency. Calculations regarding hybridization conditions required for attaining particular degrees of stringency are discussed in Sambrook et al. (ed.), Molecular Cloning: A Laboratory Manual, 2nd ed., vol. 1-3, Cold Spring Harbor Laboratory Press, Cold Spring Harbor, N.Y., 1989.

As used herein, the term "stringent conditions" encompasses conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize. In particular embodiments, stringent conditions can include hybridization at 65° C., followed by washes at 65° C. with 0.1×SSC/0.1% SDS for 40 minutes. The following are representative, non-limiting hybridization conditions:

Very High Stringency: hybridization in 5×SSC buffer at 65° C. for 16 hours; wash twice in 2×SSC buffer at room temperature for 15 minutes each; and wash twice in 0.5×SSC buffer at 65° C. for 20 minutes each.

High Stringency: Hybridization in 5-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency: Hybridization in 6×SSC buffer at room temperature to 55° C. for 16-20 hours; wash at least twice in 2-3×SSC buffer at room temperature to 55° C. for 20-30 minutes each.

In an embodiment, specifically hybridizable nucleic acid molecules can remain bound under very high stringency hybridization conditions. In an embodiment, specifically hybridizable nucleic acid molecules can remain bound under high stringency hybridization conditions. In an embodiment, specifically hybridizable nucleic acid molecules can remain bound under moderate stringency hybridization conditions.

As used herein, the term "oligonucleotide" refers to a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in polymerase chain reaction, a technique for the amplification of small DNA sequences. In polymerase chain reaction, an oligonucleotide is typically referred to as a "primer" which allows a DNA polymerase to extend the oligonucleotide and replicate the complementary strand.

As used herein, the terms "Polymerase Chain Reaction" or "PCR" refer to a procedure or technique in which minute amounts of nucleic acid, RNA and/or DNA, are amplified as described in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51:263 (1987); Erlich, ed., PCR Technology, (Stockton Press, NY, 1989).

As used herein, the term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, that may include constituents which are co-factors or which affect conditions such as pH and the like at various suitable temperatures. A primer is preferably a single strand sequence, such that amplification efficiency is optimized, but double stranded sequences can be utilized.

As used herein, the term "probe" refers to an oligonucleotide or polynucleotide sequence that hybridizes to a target sequence. In the TaqMan® or TaqMan®-style assay procedure, the probe hybridizes to a portion of the target situated between the annealing site of the two primers. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides.

In the Southern blot assay procedure, the probe hybridizes to a DNA fragment that is attached to a membrane. A probe includes about ten nucleotides, about 100 nucleotides, about 250 nucleotides, about 500 nucleotides, about 1,000 nucleotides, about 2,500 nucleotides, or about 5,000 nucleotides. In some embodiments, a probe includes from about 500 nucleotides to about 2,500 nucleotides.

A probe can further include a detectable label, e.g., a radioactive label, a biotinylated label, a fluorophore (Texas-Red®, fluorescein isothiocyanate, etc.,). The detectable label can be covalently attached directly to the probe oligonucleotide, e.g., located at the probe's 5' end or at the probe's 3' end. A probe including a fluorophore may also further include a quencher, e.g., Black Hole Quencher™, Iowa Black™, etc.

As used herein, the terms "sequence identity" or "identity" can be used interchangeably and refer to nucleic acid residues in two sequences that are the same when aligned for maximum correspondence over a specified comparison window.

As used herein, the term "percentage of sequence identity" refers to a value determined by comparing two optimally aligned sequences (e.g., nucleic acid sequences or amino acid sequences) over a comparison window, wherein the portion of a sequence in the comparison window may comprise additions or deletions (i.e., gaps) as compared to a reference sequence (that does not comprise additions or deletions) for optimal alignment of the two sequences. A percentage is calculated by determining the number of positions at which an identical nucleic acid or amino acid residue occurs in both sequences to yield the number of matched positions, dividing the number of matched positions by the total number of positions in the comparison window, and multiplying the result by 100 to yield the percentage of sequence identity. Methods for aligning sequences for comparison are well known. Various programs and alignment algorithms are described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.*

85:2444; Higgins and Sharp (1988) *Gene* 73:237-44; Higgins and Sharp (1989) *CABIOS* 5:151-3; Corpet et al. (1988) *Nucleic Acids Res.* 16:10881-90; Huang et al. (1992) *Comp. Appl. Biosci.* 8:155-65; Pearson et al. (1994) *Methods Mol. Biol.* 24:307-31; Tatiana et al. (1999) *FEMS Microbiol. Lett.* 174:247-50.

The National Center for Biotechnology Information (NCBI) Basic Local Alignment Search Tool (BLAST™; Altschul et al. (1990) *J. Mol. Biol.* 215:403-10) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

As used herein, the term "operably linked" refers to a nucleic acid placed into a functional relationship with another nucleic acid. Generally, "operably linked" can mean that linked nucleic acids are contiguous. Linking can be accomplished by ligation at convenient restriction sites. If such sites do not exist, synthetic oligonucleotide adaptors or linkers are ligated or annealed to the nucleic acid and used to link the contiguous polynucleotide fragment. However, elements need not be contiguous to be operably linked.

As used herein, the term "promoter" refers to a region of DNA that generally is located upstream (towards the 5' region of a gene) of a gene and is needed to initiate and drive transcription of the gene. A promoter may permit proper activation or repression of a gene that it controls. A promoter may contain specific sequences that are recognized by transcription factors. These factors may bind to a promoter DNA sequence, which results in the recruitment of RNA polymerase, an enzyme that synthesizes RNA from the coding region of the gene. The promoter generally refers to all gene regulatory elements located upstream of the gene, including, upstream promoters, 5'-UTR, introns, and leader sequences.

As used herein, the term "upstream-promoter" refers to a contiguous polynucleotide sequence that is sufficient to direct initiation of transcription. As used herein, an upstream-promoter encompasses the site of initiation of transcription with several sequence motifs, which include TATA Box, initiator sequence, TFIIB recognition elements and other promoter motifs (Jennifer, E. F. et al, (2002) *Genes & Dev.,* 16: 2583-2592). The upstream promoter provides the site of action to RNA polymerase II which is a multi-subunit enzyme with the basal or general transcription factors like, TFIIA, B, D, E, F and H. These factors assemble into a transcription pre initiation complex that catalyzes the synthesis of RNA from DNA template.

The activation of the upstream-promoter is done by the additional sequence of regulatory DNA sequence elements to which various proteins bind and subsequently interact with the transcription initiation complex to activate gene expression. These gene regulatory elements sequences interact with specific DNA-binding factors. These sequence motifs may sometimes referred to as cis-elements. Such cis-elements, to which tissue-specific or development-specific transcription factors bind, individually or in combination, may determine the spatiotemporal expression pattern of a promoter at the transcriptional level. These cis-elements vary widely in the type of control they exert on operably linked genes. Some elements act to increase the transcription of operably-linked genes in response to environmental responses (e.g., temperature, moisture, and wounding). Other cis-elements may respond to developmental cues (e.g., germination, seed maturation, and flowering) or to spatial information (e.g., tissue specificity). See, for example, Langridge et al. (1989) Proc. Natl. Acad. Sci. USA 86:3219-23. These cis-elements are located at a varying distance from transcription start point, some cis-elements (called proximal elements) are adjacent to a minimal core promoter region while other elements can be positioned several kilobases upstream or downstream of the promoter (enhancers).

A "DNA binding transgene" is a polynucleotide coding sequence that encodes a DNA binding protein. The DNA binding protein is subsequently able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

Examples of DNA binding proteins include; meganucleases, zinc fingers, CRISPRs and TALE binding domains that can be "engineered" to bind to a predetermined nucleotide sequence. Typically, the engineered DNA binding proteins (e.g., zinc fingers, CRISPRs, or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP, CRISPR, and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication Nos. 20110301073, 20110239315 and 20119145940.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261 and 6,794,136; see also WO 98/53058; WO 98/53059; WO 98/53060; WO 02/016536 and WO 03/016496.

In other examples, the DNA-binding domain of one or more of the nucleases comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than different effector proteins into the plant cell. Among these injected proteins are transcription activator-like (TALEN) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar strain GMI1000 and in the biovar 4 strain RS1000 (See Heuer et al (2007) *Appl and Enviro Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Patent Publication No. 20110301073, incorporated by reference in its entirety.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target).

The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and Archea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer". Cas9 cleaves the DNA to generate blunt ends at the DSB at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al (2012) Science 337, p. 816-821, Jinek et al, (2013), eLife 2:e00471, and David Segal, (2013) eLife 2:e00563). Thus, the CRISPR/Cas system can be engineered to create a double-stranded break (DSB) at a desired target in a genome, and repair of the DSB can be influenced by the use of repair inhibitors to cause an increase in error prone repair.

In other examples, the DNA binding transgene is a site specific nuclease that comprises an engineered (non-naturally occurring) Meganuclease (also described as a homing endonuclease). The recognition sequences of homing endonucleases or meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-30 3388; Dujon et al. (1989) *Gene* 82:115-118; Perler et al. (1994) *Nucleic Acids Res.* 22, 11127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 5 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

As used herein, the term "transformation" encompasses all techniques that a nucleic acid molecule can be introduced into such a cell. Examples include, but are not limited to: transfection with viral vectors; transformation with plasmid vectors; electroporation; lipofection; microinjection (Mueller et al. (1978) Cell 15:579-85); *Agrobacterium*-mediated transfer; direct DNA uptake; WHISKERS™-mediated transformation; and microprojectile bombardment. These techniques may be used for both stable transformation and transient transformation of a plant cell. "Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms. "Transient transformation" refers to the introduction of a nucleic acid fragment into the nucleus, or DNA-containing organelle, of a host organism resulting in gene expression without genetically stable inheritance.

As used herein, the term "transduce" refers to a process where a virus transfers nucleic acid into a cell.

As used herein, the term "transgene" refers to an exogenous nucleic acid sequence. In one example, a transgene is a gene sequence (e.g., an herbicide-resistance gene), a gene encoding an industrially or pharmaceutically useful compound, or a gene encoding a desirable agricultural trait. In yet another example, a transgene is a small RNA, such as an antisense nucleic acid sequence, wherein expression of the small RNA sequence inhibits expression of a target nucleic acid sequence. A transgene may contain regulatory sequences operably linked to the transgene (e.g., a promoter, intron, or 3'-UTR). In some embodiments, a nucleic acid of interest is a transgene. However, in other embodiments, a nucleic acid of interest is an endogenous nucleic acid, wherein additional genomic copies of the endogenous nucleic acid are desired, or a nucleic acid that is in the antisense orientation with respect to the sequence of a target nucleic acid in a host organism.

As used herein, the term "small RNA" refers to several classes of non-coding ribonucleic acid (ncRNA). The term small RNA describes the short chains of ncRNA produced in bacterial cells, animals, plants, and fungi. These short chains of ncRNA may be produced naturally within the cell or may be produced by the introduction of an exogenous sequence that expresses the short chain or ncRNA. The small RNA sequences do not directly code for a protein, and differ in function from other RNA in that small RNA sequences are only transcribed and not translated. The small RNA sequences are involved in other cellular functions, including gene expression and modification. Small RNA molecules are usually made up of about 20 to 30 nucleotides. The small RNA sequences may be derived from longer precursors. The precursors form structures that fold back on each other in self-complementary regions; they are then processed by the nuclease Dicer in animals or DCL1 in plants.

Many types of small RNA exist either naturally or produced artificially, including microRNAs (miRNAs), short interfering RNAs (siRNAs), antisense RNA, short hairpin RNA (shRNA), and small nucleolar RNAs (snoRNAs). Certain types of small RNA, such as microRNA and siRNA, are important in gene silencing and RNA interference (RNAi). Gene silencing is a process of genetic regulation in which a gene that would normally be expressed is "turned off" by an intracellular element, in this case, the small RNA. The protein that would normally be formed by this genetic information is not formed due to interference, and the information coded in the gene is blocked from expression.

As used herein, the term "small RNA" encompasses RNA molecules described in the literature as "tiny RNA" (Storz, (2002) *Science* 296:1260-3; Illangasekare et al., (1999) *RNA* 5:1482-1489); prokaryotic "small RNA" (sRNA) (Wassarman et al., (1999) *Trends Microbiol.* 7:37-45); eukaryotic "noncoding RNA (ncRNA)"; "micro-RNA (miRNA)"; "small non-mRNA (snmRNA)"; "functional RNA (fRNA)"; "transfer RNA (tRNA)"; "catalytic RNA" [e.g., ribozymes, including self-acylating ribozymes (Illangaskare et al., (1999) *RNA* 5:1482-1489); "small nucleolar RNAs (snoRNAs)"; "tmRNA" (a.k.a. "10S RNA", Muto et al., (1998) *Trends Biochem Sci.* 23:25-29; and Gillet et al., (2001) *Mol Microbiol.* 42:879-885); RNAi molecules including without limitation "small interfering RNA (siRNA)", "endoribonuclease-prepared siRNA (e-siRNA)", "short hairpin RNA (shRNA)", and "small temporally regulated RNA (stRNA)"; "diced siRNA (d-siRNA)", and aptamers, oligonucleotides and other synthetic nucleic acids that comprise at least one uracil base.

As used herein, the term "vector" refers to a nucleic acid molecule as introduced into a cell, thereby producing a transformed cell. A vector may include nucleic acid sequences that permit it to replicate in the host cell, such as an origin of replication. Examples include, but are not limited to, a plasmid, cosmid, bacteriophage, bacterial artificial chromosome (BAC), or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector. A vector may optionally include materials to aid in achieving entry of the nucleic acid molecule into the cell (e.g., a liposome).

As used herein, the terms "cassette", "expression cassette", and "gene expression cassette" refer to a segment of DNA that can be inserted into a nucleic acid or polynucleotide at specific restriction sites or by homologous recombination. A segment of DNA comprises a polynucleotide containing a gene of interest that encodes a small RNA or a polypeptide of interest, and the cassette and restriction sites are designed to ensure insertion of the cassette in the proper reading frame for transcription and translation. In an embodiment, an expression cassette can include a polynucleotide that encodes a small RNA or a polypeptide of interest and having elements in addition to the polynucleotide that facilitate transformation of a particular host cell. In an embodiment, a gene expression cassette may also include elements that allow for enhanced expression of a small RNA or a polynucleotide encoding a polypeptide of interest in a host cell. These elements may include, but are not limited to: a promoter, a minimal promoter, an enhancer, a response element, an intron, a 5' untranslated, a 3' untranslated region sequence, a terminator sequence, a polyadenylation sequence, and the like.

As used herein, the term "heterologous coding sequence" is used to indicate any polynucleotide that codes for, or ultimately codes for, a peptide or protein or its equivalent amino acid sequence, e.g., an enzyme, that is not normally present in the host organism and can be expressed in the host cell under proper conditions. As such, "heterologous coding sequences" may include one or additional copies of coding sequences that are not normally present in the host cell, such that the cell is expressing additional copies of a coding sequence that are not normally present in the cells. The heterologous coding sequences can be RNA or any type thereof, e.g., mRNA, DNA or any type thereof, e.g., cDNA, or a hybrid of RNA/DNA. Examples of coding sequences include, but are not limited to, full-length transcription units that comprise such features as the coding sequence, introns, promoter regions, 5'-UTR, 3'-UTRs and enhancer regions.

"Heterologous coding sequences" also includes the coding portion of the peptide or enzyme, i.e., the cDNA or mRNA sequence, of the peptide or enzyme, as well as the coding portion of the full-length transcriptional unit, i.e., the gene comprising introns and exons, as well as "codon optimized" sequences, truncated sequences or other forms of altered sequences that code for the enzyme or code for its equivalent amino acid sequence, provided that the equivalent amino acid sequence produces a functional protein. Such equivalent amino acid sequences can have a deletion of one or more amino acids, with the deletion being N-terminal, C-terminal or internal. Truncated forms are envisioned as long as they have the catalytic capability indicated herein.

As used herein, the term "control" refers to a sample used in an analytical procedure for comparison purposes. A control can be "positive" or "negative". For example, where the purpose of an analytical procedure is to detect a differentially expressed transcript or polypeptide in cells or tissue, it is generally preferable to include a positive control, such as a sample from a known plant exhibiting the desired expression, and a negative control, such as a sample from a known plant lacking the desired expression.

As used herein, the term "plant" includes plants and plant parts including but not limited to plant cells and plant tissues such as leaves, stems, roots, flowers, pollen, and seeds. A class of plant that can be used in the present invention is generally as broad as the class of higher and lower plants amenable to mutagenesis including angiosperms, gymnosperms, ferns and multicellular algae. Thus, "plant" includes dicot and monocot plants. Examples of dicotyledonous plants include tobacco, Arabidopsis, soybean, tomato, papaya, canola, sunflower, cotton, alfalfa, potato, grapevine, pigeon pea, pea, Brassica, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledonous plants include corn, rice, wheat, sugarcane, barley, rye, sorghum, orchids, bamboo, banana, cattails, lilies, oat, onion, millet, and triticale.

As used herein, the term "plant material" refers to leaves, stems, roots, flowers or flower parts, fruits, pollen, egg cells, zygotes, seeds, cuttings, cell or tissue cultures, or any other part or product of a plant. In an embodiment, plant material includes cotyledon and leaf. In an embodiment, plant material includes root tissues and other plant tissues located underground.

As used herein, the term "selectable marker gene" refers to a gene that is optionally used in plant transformation to, for example, protect plant cells from a selective agent or provide resistance/tolerance to a selective agent. In addition, "selectable marker gene" is meant to encompass reporter genes. Only those cells or plants that receive a functional selectable marker are capable of dividing or growing under conditions having a selective agent. Examples of selective agents can include, for example, antibiotics, including spectinomycin, neomycin, kanamycin, paromomycin, gentamicin, and hygromycin. These selectable markers include neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes can include genes encoding herbicide resistance including bar or pat (resistance against glufosinate ammonium or phosphinothricin), acetolactate synthase (ALS, resistance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), glyphosate, 2,4-D, and metal resistance or sensitivity. Examples of "reporter genes" that can be used as a selectable marker gene include the visual observation of expressed reporter gene proteins such as proteins encoding β-glucuronidase (GUS), luciferase, green fluorescent protein (GFP), yellow fluorescent protein (YFP), DsRed, β-galactosidase, chloramphenicol acetyltransferase (CAT), alkaline phosphatase, and the like. The phrase "marker-positive" refers to plants that have been transformed to include a selectable marker gene.

As used herein, the term "detectable marker" refers to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In an embodiment, a detectable marker can be attached by spacer arms of various lengths to reduce potential steric hindrance.

As used herein, the term "detecting" is used in the broadest sense to include both qualitative and quantitative measurements of a specific molecule, for example, measurements of a specific polypeptide.

Unless otherwise specifically explained, all technical and scientific terms used herein have the same meaning as commonly understood by those of ordinary skill in the art that this disclosure belongs. Definitions of common terms in molecular biology can be found in, for example: Lewin, Genes V, Oxford University Press, 1994; Kendrew et al. (eds.), The Encyclopedia of Molecular Biology, Blackwell Science Ltd., 1994; and Meyers (ed.), Molecular Biology and Biotechnology: A Comprehensive Desk Reference, VCH Publishers, Inc., 1995.

Regulatory Elements

Plant promoters used for basic research or biotechnological applications are generally unidirectional, directing the expression of transgene that has been fused at its 3' end (downstream). It is often necessary to robustly express transgenes within plants for metabolic engineering and trait stacking. In addition, multiple novel promoters are typically required in transgenic crops to drive the expression of multiple genes. Disclosed herein is a chimeric promoter that can direct the expression of a transgene that has been fused at its 3' end (downstream).

Development of transgenic products is becoming increasingly complex, which requires robustly expressing transgenes and stacking multiple transgenes into a single locus. Traditionally, each transgene requires a unique promoter for expression wherein multiple promoters are required to express different transgenes within one gene stack. With an increasing size of gene stacks, this frequently leads to repeated use of the same promoter to obtain similar levels of expression patterns of different transgenes for expression of a single polygenic trait. Multi-gene constructs driven by the same promoter are known to cause gene silencing resulting in less efficacious transgenic products in the field. Excess of transcription factor (TF)-binding sites due to promoter repetition can cause depletion of endogenous TFs leading to transcriptional inactivation. The silencing of transgenes will likely undesirably affect performance of a transgenic plant produced to express transgenes. Repetitive sequences within a transgene may lead to gene intra locus homologous recombination resulting in polynucleotide rearrangements.

Tissue specific (i.e., tissue-preferred) or organ specific promoters drive gene expression in a certain tissue such as in the kernel, root, leaf or tapetum of the plant. Tissue and developmental stage specific promoters derive the expression of genes, which are expressed in particular tissues or at particular time periods during plant development. Tissue specific promoters are required for certain applications in the transgenic plants industry and are desirable as they permit specific expression of heterologous genes in a tissue and/or developmental stage selective manner, indicating expression of the heterologous gene differentially at a various organs, tissues and/or times, but not in other. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene in plant tissues that are in a particular growth or developmental phase such as, for example, cell division or elongation. Another application is the desirability of using tissue specific promoters, e.g. such that would confine the expression of the transgenes encoding an agronomic trait in developing xylem. One particular problem remaining in the identification of tissue specific promoters is how to identify the potentially most important genes and their corresponding promoters, and to relate these to specific developmental properties of the cell. Another problem is to clone all relevant cis-acting transcriptional control elements so that the cloned DNA fragment drives transcription in the wanted specific expression pattern. A particular problem is to identify tissue-specific promoters, related to specific cell types, developmental stages and/or functions in the plant that are not expressed in other plant tissues.

Transgene expression may also be regulated by an intron and 5'-UTR region located downstream of the promoter sequence. A chimeric promoter comprising an upstream-promoter from operably linked to an intron, and 5'-UTR can regulate transgene expression. While an upstream-promoter is necessary to drive transcription, the presence of an intron and 5'-UTR can increase expression levels resulting in mRNA transcript for translation and protein synthesis. Addition of an intron and 5'-UTR to an upstream-promoter polynucleotide sequence can aid stable expression of a transgene.

Provided are methods and constructs using a chimeric promoter gene regulatory element comprising an upstream-promoter from *Zea mays* Peroxidase 5 followed by the *Zea mays* alcohol dehydrogenase (I), intron 6 and Maize Streak Virus 5'-UTR (e.g., leader) to express transgenes in plant. In an embodiment, a chimeric promoter can be a promoter of:

```
                                              (SEQ ID NO: 1)
ACCACTGTTGTAACTTGTAAGCCACTAGCTCACGTTCTCCATGAGCTCTT

CTCTCTGCTGTTTCTTCCTCTGCTAACTGCGTTATGATATGACGTCGTAT

AAATAATCTCACAATACTTCCTTATTTTCAGCATGGCCTCTTTTATGTTT

ATTTAACAGTAGCAACCAACGCCGCTCGATGTTTCCTTCAAGAAACGGCC

ACTCACTATGTGGTGTGCAGAAGAACAAATGTAAGCAGCTCCTACAGGTA

CCAGTAGTCATGTCAGTGTGGAAGCTTTCCAACCAACGCCTCCTTCGAGG

AACCTGGTCGTGCTGACATGAATGTAGGCCATGCAAGCACAAGCACCTAA

CGCGAATCATCACGACGCGCCGTGTACTGGGCGTTGGTACATCACACCCC

GCGTTTGACCTGATCGGAAGCATGCGTGTGTGTTGGCTGCAGGACCGGCT

ATAGGTTTCCTGCATTGGACAGCAGAAGCCAGTCATGTTAGGCACTCACG

CGCTCCTGCCGTTTGATGAATCATCCGGTCTTTCGTATTGATCACTAGTT

CACTACGCTGATATAGCAAATTTTAAGATGTGAAACCACGAGACGAGCGA

TAAATCTTAGACGTTACCTATCCATATGAAGCTTGTGCGAAAAAAAGGCG

TGCCGCTGTAGCATCATTCGTATACACTTTTGTCCCAAAGACAGGGATA

CGAATCCATGCTCGACAGAACCCTCCCTTCCCTGCAGATAACGACACTTA

AGTATAACAAAAGTAGTTGGATTATTTCAGAAGCAAAATCTCACTTTTCG

CTGGCCTTTTTGTACTTTGGTTACTTGAGTTCAGACAGTGTATGCTATAT

TGTCATGTGCTGCGTAAGGTTTAAATATGGTTCGACAAATATATCAGTAT

ATCACTACTTTGTTATGGGTGGGGCCTAGCACAAACTTGATACAGCTAGG

ATAAAGTTAGAACGATGACTGATCTACTGTAAAGCGACACCTGTCCTGTT

ATGGTAGTTTAAGTCCATTCCTGGACGACTCCAGATCCAGGATATGATGC

TGTTACATAATGCGATTGTTCACAATAAAATTGCATGATGTTCTTCTACT

CTTTAGGCAGTTTTGTTCAACAGGCAAGTTGCATAATGCATGTGCATATA

TGAGCAGCATAATCATCAATTAATCATAGGTTCGTCATTTTAGTTTCACT

CCTTCACATTATTCCAGCCCTTGAAGAAAAATGTAGCAGTGCTTGCTGTT

TAATAAGTGGCAGAGCTGTTTTCACTCCACCTACGCTTGTCTAGGACCAA

AATTTTAATCTGTCACTTTGAGCTAAAACTGAAGCACCAAACCGCTACAA

AAGAACGTAGGAGCTGAATTGTAACTTGATGGGATTACTATAGCAGTTGC

TACAGTTCTAGCTAGCTACCTTATTCTATACGCATCACCCTAACAACCCG

GCTGACTGCTGCATCTGACCCCACCGTCCCTGCTCCAAACCAACTCTCC

TTTCCTTGCATGCACTACACCCACTTCCTGCAGCTATATATACCACCATA

TGCCCATCTTATGAAACCATCCACAAGAGGAGAAGAAACAATCAACCAGC

AACACTCTTCTCTTATAACATAGTACAGCGAAGGTAACTCACGGTACCCT

GAAGGCTCGACAAGGCAGTCCACGGAGGAGCTGATATTTGGTGGACAAGC

TGTGGATAGGAGCAACCCTATCCCTAATATACCAGCACCACCAAGTCAGG

GCAATCCCCAGATCACCCCAGCAGATTCGAAGAAGGTACAGTACACACAC

ATGTATATATGTATGATGTATCCCTTCGATCGAAGGCATGCCTTGGTATA

ATCACTGAGTAGTCATTTTATTACTTTGTTTTGACAAGTCAGTAGTTCAT

CCATTTGTCCCATTTTTTCAGCTTGGAAGTTTGGTTGCACTGGCCTTGGT

CTAATAACTGAGTAGTCATTTTATTACGTTGTTTCGACAAGTCAGTAGCT

CATCCATCTGTCCCATTTTTTCAGCTAGGAAGTTTGGTTGCACTGGCCTTT

GGACTAATAACTGATTAGTCATTTTATTACATTGTTTCGACAAGTCAGTA

GCTCATCCATCTGTCCCATTTTTCAGCTAGGAAGTTCGGATCTGGGGCCA

TTTGTTCCAGGCACGGGATAAGCATTCAG
```

In an embodiment, a gene expression cassette comprises a promoter. In an embodiment, a promoter can be a chimeric promoter of the subject disclosure. In an embodiment, a gene expression cassette comprises a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1. In an embodiment, a gene expression cassette comprises a chimeric promoter that is operably linked to a transgene. In an embodiment, a gene expression cassette comprising the chimeric promoter may drive expression of two or more transgenes. In an illustrative embodiment, a gene expression cassette comprises a chimeric promoter that is operably linked to a transgene, wherein the transgene can be an insecticidal resistance transgene, a herbicide tolerance transgene, a nitrogen use efficiency transgene, a water use efficiency transgene, a nutritional quality transgene, a DNA binding transgene, a selectable marker transgene, or combinations thereof.

Selectable Markers

Various selectable markers also described as reporter genes can be incorporated into a chosen expression vector to allow for identification and selection of transformed plants ("transformants"). Many methods are available to confirm expression of selectable markers in transformed plants, including for example DNA sequencing and PCR (polymerase chain reaction), Southern blotting, RNA blotting, immunological methods for detection of a protein expressed from the vector, e g., precipitated protein that mediates phosphinothricin resistance, or visual observation of other proteins such as reporter genes encoding β-glucuronidase (GUS), luciferase, green fluorescent protein (GFP), yellow fluorescent protein (YFP), DsRed, β-galactosidase, chloramphenicol acetyltransferase (CAT), alkaline phosphatase, and the like (See Sambrook, et al., Molecular Cloning: A Laboratory Manual, Third Edition, Cold Spring Harbor Press, N.Y., 2001, the content is incorporated herein by reference in its entirety).

Selectable marker genes are utilized for selection of transformed cells or tissues. Selectable marker genes include genes encoding antibiotic resistance, such as those encoding neomycin phosphotransferase II (NEO) and hygromycin phosphotransferase (HPT) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate has been obtained by using genes coding for mutant target enzymes, 5-enolpyruvylshikimate-3-phosphate synthase (EPSPS). Genes and mutants for EPSPS are well known, and further described below. Resistance to glufosinate ammonium, bromoxynil, and 2,4-dichlorophenoxyacetate (2,4-D) have been obtained by using bacterial genes encoding pat or DSM-2, a nitrilase, an aad-1 or an aad-12 gene, which detoxifies the respective herbicides.

In an embodiment, herbicides can inhibit the growing point or meristem, including imidazolinone or sulfonylurea, and genes for resistance/tolerance of acetohydroxyacid synthase (AHAS) and acetolactate synthase (ALS) for these herbicides are well known. Glyphosate resistance genes include mutant 5-enolpyruvylshikimate-3-phosphate synthase (EPSPs) and dgt-28 genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include bar genes from *Streptomyces* species, including *Streptomyces hygroscopicus* and *Streptomyces viridichromogenes*, and pyridinoxy or phenoxy proprionic acids and cyclohexones (ACCase inhibitor-encoding genes). Exemplary genes conferring resistance to cyclohexanediones and/or aryloxyphenoxypropanoic acid (including Haloxyfop, Diclofop, Fenoxyprop, Fluazifop, Quizalofop) include genes of acetyl coenzyme A carboxylase (ACCase)—Accl-S1, Accl-S2 and Accl-S3. In an embodiment, herbicides can inhibit photosynthesis, including triazine (psbA and ls+ genes) or benzonitrile (nitrilase gene).

In an embodiment, selectable marker genes include, but are not limited to genes encoding: neomycin phosphotransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvyl-shikimate-phosphate synthase (aroA); haloarylnitrilase; acetyl-coenzyme A carboxylase; dihydropteroate synthase (sul I); and 32 kD photosystem II polypeptide (psbA).

An embodiment also includes genes encoding resistance to: chloramphenicol; methotrexate; hygromycin; spectinomycin; bromoxynil; glyphosate; and phosphinothricin.

The above list of selectable marker genes is not meant to be limiting. Any reporter or selectable marker gene are encompassed by the present invention.

Selectable marker genes are synthesized for optimal expression in a plant. For example, in an embodiment, a coding sequence of a gene has been modified by codon optimization to enhance expression in plants. A selectable marker gene can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a selectable marker gene is designed to be expressed in plants at a higher level resulting in higher transformation efficiency. Methods for plant optimization of genes are well known. Guidance regarding the optimization and manufacture of synthetic polynucleotide sequences can be found in, for example, WO2013016546, WO2011146524, WO1997013402, U.S. Pat. No. 6,166,302, and U.S. Pat. No. 5,380,831, herein incorporated by reference.

Transgenes

The disclosed methods and compositions can be used to express polynucleotide gene sequences within the plant genome. Accordingly, expression of genes encoding herbicide tolerance, insect resistance, nutrients, antibiotics or therapeutic molecules can be driven by a plant promoter.

In one embodiment the chimeric regulatory element of the subject disclosure is combined or operably linked with gene encoding polynucleotide sequences that provide resistance or tolerance to glyphosate or another herbicide, and/or provides resistance to select insects or diseases and/or nutritional enhancements, and/or improved agronomic characteristics, and/or proteins or other products useful in feed, food, industrial, pharmaceutical or other uses. The transgenes can be "stacked" with two or more nucleic acid sequences of interest within a plant genome. Stacking can be accomplished, for example, via conventional plant breeding using two or more events, transformation of a plant with a construct which contains the sequences of interest, re-transformation of a transgenic plant, or addition of new traits through targeted integration via homologous recombination.

Such polynucleotide sequences of interest include, but are not limited to, those examples provided below:

1. Genes or Coding Sequence (e.g. iRNA) That Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium flavum* (Jones et al., 1994 Science 266:789), tomato Pto gene, which encodes a protein kinase, for resistance to *Pseudomonas syringae* pv. tomato (Martin et al., 1993 Science 262:1432), and *Arabidopsis* RSSP2 gene for resistance to *Pseudomonas syringae* (Mindrinos et al., 1994 Cell 78:1089).

(B) A *Bacillus thuringiensis* protein, a derivative thereof or a synthetic polypeptide modeled thereon, such as, a nucleotide sequence of a Bt δ-endotoxin gene (Geiser et al., 1986 Gene 48:109), and a vegetative insecticidal (VIP) gene (see, e.g., Estruch et al. (1996) Proc. Natl. Acad. Sci. 93:5389-94). Moreover, DNA molecules encoding δ-endotoxin genes can be purchased from American Type Culture Collection (Rockville, Md.), under ATCC accession numbers 40098, 67136, 31995 and 31998.

(C) A lectin, such as, nucleotide sequences of several *Clivia miniata* mannose-binding lectin genes (Van Damme et al., 1994 Plant Molec. Biol. 24:825).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include a rice cysteine proteinase inhibitor (Abe et al., 1987 J. Biol. Chem. 262:16793), a tobacco proteinase inhibitor I (Huub et al., 1993 Plant Molec. Biol. 21:985), and an α-amylase inhibitor (Sumitani et al., 1993 Biosci. Biotech. Biochem. 57:1243).

(F) An insect-specific hormone or pheromone such as an ecdysteroid and juvenile hormone a variant thereof, a mimetic based thereon, or an antagonist or agonist thereof, such as baculovirus expression of cloned juvenile hormone esterase, an inactivator of juvenile hormone (Hammock et al., 1990 Nature 344:458).

(G) An insect-specific peptide or neuropeptide which, upon expression, disrupts the physiology of the affected pest (J. Biol. Chem. 269:9). Examples of such genes include an insect diuretic hormone receptor (Regan, 1994), an allostatin identified in *Diploptera punctata* (Pratt, 1989), and insect-specific, paralytic neurotoxins (U.S. Pat. No. 5,266,361).

(H) An insect-specific venom produced in nature by a snake, a wasp, etc., such as a scorpion insectotoxic peptide (Pang, 1992 Gene 116:165).

(I) An enzyme responsible for a hyperaccumulation of monoterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., 1993 Insect Molec. Biol. 23:691), and parsley ubi4-2 polyubiquitin gene (Kawalleck et al., 1993 Plant Molec. Biol. 21:673).

(K) A molecule that stimulates signal transduction. Examples of such molecules include nucleotide sequences for mung bean calmodulin cDNA clones (Botella et al., 1994 Plant Molec. Biol. 24:757) and a nucleotide sequence of a maize calmodulin cDNA clone (Griess et al., 1994 Plant Physiol. 104:1467).

(L) A hydrophobic moment peptide. See U.S. Pat. Nos. 5,659,026 and 5,607,914; the latter teaches synthetic antimicrobial peptides that confer disease resistance.

(M) A membrane permease, a channel former or a channel blocker, such as a cecropin-β lytic peptide analog (Jaynes et al., 1993 Plant Sci. 89:43) which renders transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al. (1990) Ann. Rev. Phytopathol. 28:451.

(O) An insect-specific antibody or an immunotoxin derived therefrom. Thus, an antibody targeted to a critical metabolic function in the insect gut would inactivate an affected enzyme, killing the insect. For example, Taylor et al. (1994) Abstract #497, Seventh Int'l. Symposium on Molecular Plant-Microbe Interactions shows enzymatic inactivation in transgenic tobacco via production of single-chain antibody fragments.

(P) A virus-specific antibody. See, for example, Tavladoraki et al. (1993) Nature 266:469, which shows that transgenic plants expressing recombinant antibody genes are protected from virus attack.

(Q) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., 1992) Bio/Technology 10:1436. The cloning and characterization of a gene which encodes a bean endopolygalacturonase-inhibiting protein is described by Toubart et al. (1992 Plant J. 2:367).

(R) A developmental-arrestive protein produced in nature by a plant, such as the barley ribosome-inactivating gene that provides an increased resistance to fungal disease (Longemann et al., 1992). Bio/Technology 10:3305.

(S) RNA interference, in which an RNA molecule is used to inhibit expression of a target gene. An RNA molecule in one example is partially or fully double stranded, which triggers a silencing response, resulting in cleavage of dsRNA into small interfering RNAs, which are then incorporated into a targeting complex that destroys homologous mRNAs. See, e.g., Fire et al., U.S. Pat. No. 6,506,559; Graham et al. U.S. Pat. No. 6,573,099.

2. Genes That Confer Resistance to a Herbicide (A) Genes encoding resistance or tolerance to a herbicide that inhibits the growing point or meristem, such as an imidazalinone, sulfonanilide or sulfonylurea herbicide. Exemplary genes in this category code for mutant acetolactate synthase (ALS) (Lee et al., 1988 EMBO J. 7:1241) also known as acetohydroxyacid synthase (AHAS) enzyme (Miki et al., 1990 Theor. Appl. Genet. 80:449).

(B) One or more additional genes encoding resistance or tolerance to glyphosate imparted by mutant EPSP synthase and aroA genes, or through metabolic inactivation by genes such as DGT-28, 2mEPSPS, GAT (glyphosate acetyltransferase) or GOX (glyphosate oxidase) and other phosphono compounds such as glufosinate (pat,bar, and dsm-2 genes), and aryloxyphenoxypropionic acids and cyclohexanediones (ACCase inhibitor encoding genes). See, for example, U.S. Pat. No. 4,940,835, which discloses the nucleotide sequence of a form of EPSP which can confer glyphosate resistance. A DNA molecule encoding a mutant aroA gene can be obtained under ATCC Accession Number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricinacetyl-transferase gene is provided in European application No. 0 242 246. De Greef et al. (1989) Bio/Technology 7:61 describes the production of transgenic plants that express chimeric bar genes coding for phosphinothricin acetyl transferase activity. Exemplary of genes conferring resistance to aryloxyphenoxypropionic acids and cyclohexanediones, such as sethoxydim and haloxyfop, are the Accl-S1, Accl-S2 and Accl-S3 genes described by Marshall et al. (1992) Theor. Appl. Genet. 83:435.

(C) Genes encoding resistance or tolerance to a herbicide that inhibits photosynthesis, such as a triazine (psbA and gs+ genes) and a benzonitrile (nitrilase gene). Przibilla et al. (1991) Plant Cell 3:169 describe the use of plasmids encoding mutant psbA genes to transform Chlamydomonas. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a glutathione 5-transferase is described by Hayes et al. (1992) Biochem. J. 285:173.

(D) Genes encoding resistance or tolerance to a herbicide that bind to hydroxyphenylpyruvate dioxygenases (HPPD), enzymes which catalyze the reaction in which para-hydroxyphenylpyruvate (HPP) is transformed into homogentisate. This includes herbicides such as isoxazoles (EP418175, EP470856, EP487352, EP527036, EP560482, EP682659, U.S. Pat. No. 5,424,276), in particular isoxaflutole, which is a selective herbicide for maize, diketonitriles (EP496630, EP496631), in particular 2-cyano-3-cyclopropyl-1-(2-SO2CH3-4-CF3 phenyl)propane-1,3-dione and 2-cyano-3-cyclopropyl-1-(2-S02CH3-4-2,3Cl2phenyl)propane-1,3-dione, triketones (EP625505, EP625508, U.S. Pat. No. 5,506, 195), in particular sulcotrione, and pyrazolinates. A gene that produces an overabundance of HPPD in plants can provide tolerance or resistance to such herbicides, including, for example, genes described in U.S. Pat. Nos. 6,268,549 and 6,245,968 and U.S. Patent Application, Publication No. 20030066102.

(E) Genes encoding resistance or tolerance to phenoxy auxin herbicides, such as 2,4-dichlorophenoxyacetic acid (2,4-D) and which may also confer resistance or tolerance to aryloxyphenoxypropionate (AOPP) herbicides. Examples of such genes include the α-ketoglutarate-dependent dioxygenase enzyme (aad-1) gene, described in U.S. Pat. No. 7,838,733.

(F) Genes encoding resistance or tolerance to phenoxy auxin herbicides, such as 2,4-dichlorophenoxyacetic acid (2,4-D) and which may also confer resistance or tolerance to pyridyloxy auxin herbicides, such as fluroxypyr or triclopyr. Examples of such genes include the α-ketoglutarate-dependent dioxygenase enzyme gene (aad-12), described in WO 2007/053482 A2.

(G) Genes encoding resistance or tolerance to dicamba (see, e.g., U.S. Patent Publication No. 20030135879).

(H) Genes providing resistance or tolerance to herbicides that inhibit protoporphyrinogen oxidase (PPO) (see U.S. Pat. No. 5,767,373).

(I) Genes providing resistance or tolerance to triazine herbicides (such as atrazine) and urea derivatives (such as diuron) herbicides which bind to core proteins of photosystem II reaction centers (PS II) (See Brussian et al., (1989) EMBO J. 1989, 8(4): 1237-1245.

3. Genes That Confer or Contribute to a Value-Added Trait (A) Modified fatty acid metabolism, for example, by transforming maize or Brassica with an antisense gene or stearoyl-ACP desaturase to increase stearic acid content of the plant (Knultzon et al., 1992) Proc. Nat. Acad. Sci. USA 89:2624.

(B) Decreased phytate content (1) Introduction of a phytase-encoding gene, such as the Aspergillus niger phytase gene (Van Hartingsveldt et al., 1993 Gene 127:87), enhances breakdown of phytate, adding more free phosphate to the transformed plant.

(2) A gene could be introduced that reduces phytate content. In maize, this, for example, could be accomplished by cloning and then reintroducing DNA associated with the single allele which is responsible for maize mutants characterized by low levels of phytic acid (Raboy et al., 1990 Maydica 35:383).

(C) Modified carbohydrate composition effected, for example, by transforming plants with a gene coding for an enzyme that alters the branching pattern of starch. Examples of such enzymes include, Streptococcus mucus fructosyl-transferase gene (Shiroza et al., 1988) J. Bacteriol. 170:810, Bacillus subtilis levansucrase gene (Steinmetz et al., 1985 Mol. Gen. Genel. 200:220), Bacillus licheniformis α-amylase (Pen et al., 1992 Bio/Technology 10:292), tomato invertase genes (Elliot et al., 1993), barley amylase gene (Sogaard et al., 1993 J. Biol. Chem. 268:22480), and maize endosperm starch branching enzyme II (Fisher et al., 1993 Plant Physiol. 102:10450).

Transformation

Suitable methods for transformation of plants include any method that DNA can be introduced into a cell, for example and without limitation: electroporation (see, e.g., U.S. Pat. No. 5,384,253); micro-projectile bombardment (see, e.g., U.S. Pat. Nos. 5,015,580; 5,550,318; 5,538,880; 6,160,208; 6,399,861; and 6,403,865); Agrobacterium-mediated transformation (see, e.g., U.S. Pat. Nos. 5,635,055; 5,824,877; 5,591,616; 5,981,840; and 6,384,301); and protoplast transformation (see, e.g., U.S. Pat. No. 5,508,184). These methods may be used to stably transform or transiently transform a plant.

A DNA construct may be introduced directly into the genomic DNA of the plant cell using techniques such as agitation with silicon carbide fibers (See, e.g., U.S. Pat. Nos. 5,302,523 and 5,464,765), or the DNA constructs can be introduced directly to plant tissue using biolistic methods, such as DNA particle bombardment (see, e.g., Klein et al., (1987) Nature 327:70-73). Alternatively, the DNA construct can be introduced into the plant cell via nanoparticle transformation (see, e.g., U.S. Patent Publication No. 2009/0104700, incorporated herein by reference in its entirety).

In addition, gene transfer may be achieved using non-Agrobacterium bacteria or viruses such as Rhizobium sp. NGR234, Sinorhizoboium meliloti, Mesorhizobium loti, potato virus X, cauliflower mosaic virus and cassava vein mosaic virus and/or tobacco mosaic virus, see, e.g., Chung et al. (2006) Trends Plant Sci. 11(1):1-4.

Through the application of transformation techniques, cells of virtually any plant species may be stably transformed, and these cells may be developed into transgenic plants by well-known techniques. For example, techniques that may be particularly useful in the context of cotton transformation are described in U.S. Pat. Nos. 5,846,797; 5,159,135; 5,004,863; and 6,624,344; techniques for transforming Brassica plants in particular are described, for example, in U.S. Pat. No. 5,750,871; techniques for transforming soy bean are described, for example, in U.S. Pat. No. 6,384,301; and techniques for transforming maize are described, for example, in U.S. Pat. Nos. 7,060,876 and 5,591,616, and International PCT Publication WO 95/06722.

After effecting delivery of an exogenous nucleic acid to a recipient cell, a transformed cell is generally identified for further culturing and plant regeneration. In order to improve the ability to identify transformants, one may desire to employ a selectable marker gene with the transformation vector used to generate the transformant. In an illustrative embodiment, a transformed cell population can be assayed by exposing the cells to a selective agent or agents, or the cells can be screened for the desired marker gene trait.

Cells that survive exposure to a selective agent, or cells that have been scored positive in a screening assay, may be cultured in media that supports regeneration of plants. In an embodiment, any suitable plant tissue culture media may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a desired nucleic acid comprising constructs provided in regenerating plants, a variety of assays may be performed. Such assays may include: molecular biological assays, such as Southern and Northern blotting and PCR; biochemical assays, such as detecting the presence of a protein product, e.g., by immunological means (ELISA, western blots, and/or LC-MS MS spectrophotometry) or by enzymatic function; plant part assays, such as leaf or root assays; and/or analysis of the phenotype of the whole regenerated plant.

Transgenic events may be screened, for example, by PCR amplification using, e.g., oligonucleotide primers specific for nucleic acid molecules of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (see, e.g., Rios et al. (2002) Plant J. 32:243-53), and may be applied to genomic DNA derived from any plant species or tissue type, including cell cultures. Combinations of oligonucleotide primers that bind to both target sequence and introduced sequence may be used sequentially or multiplexed in PCR amplification reactions. Oligonucleotide primers designed to anneal to the target site, introduced nucleic acid sequences, and/or combinations of the two may be produced. Thus, PCR genotyping strategies may include, for example and without limitation: amplification of specific sequences in the plant genome; amplification of multiple specific sequences in the plant genome; amplification of non-specific sequences in the plant genome; and combinations of any of the foregoing. One skilled in the art may devise additional combinations of primers and amplification reactions to interrogate the genome. For example, a set of forward and reverse oligonucleotide primers may be designed to anneal to nucleic acid sequence(s) specific for the target outside the boundaries of the introduced nucleic acid sequence.

Forward and reverse oligonucleotide primers may be designed to anneal specifically to an introduced nucleic acid molecule, for example, at a sequence corresponding to a coding region within a nucleotide sequence of interest comprised therein, or other parts of the nucleic acid molecule. Primers may be used in conjunction with primers described herein. Oligonucleotide primers may be synthesized according to a desired sequence and are commercially available (e.g., from Integrated DNA Technologies, Inc., Coralville, Iowa). Amplification may be followed by cloning and sequencing, or by direct sequence analysis of amplification products. In an embodiment, oligonucleotide primers specific for the gene target are employed in PCR amplifications.

Method of Expressing a Transgene

In an embodiment, a method of expressing at least one transgene in a plant comprises growing a plant comprising a chimeric promoter operably linked to at least one transgene. In an embodiment, a method of expressing at least one transgene in a plant tissue or plant cell comprises culturing a plant comprising a chimeric promoter operably linked to at least one transgene. In an embodiment, a method of expressing at least one transgene in a plant comprises growing a plant tissue or plant cell comprising a chimeric promoter operably linked to at least one transgene. In an embodiment, a method of expressing at least one transgene in a plant tissue or plant cell comprises culturing a plant tissue or plant cell comprising a chimeric promoter operably linked to at least one transgene.

In an embodiment, a method of expressing at least one transgene in a plant comprises growing a plant comprising a gene expression cassette comprising a chimeric promoter operably linked to at least one transgene.

In an embodiment, a method of expressing at least one transgene in a plant tissue or plant cell comprises culturing a plant tissue or plant cell comprising a gene expression cassette a chimeric promoter operably linked to at least one transgene.

In an embodiment, a plant, plant tissue, or plant cell comprises a gene expression cassette comprising a chimeric promoter operably linked to a transgene. Wherein, the chimeric promoter is comprised of an upstream-promoter, intron and 5'-UTR. In an embodiment, a plant, plant tissue, or plant cell comprises a gene expression cassette comprising an upstream-promoter, intron, and 5'-UTR. In an embodiment, the upstream-promoter, intron, and 5'-UTR is a polynucleotide of SEQ ID NO:1. In an embodiment, a plant, plant tissue, or plant cell comprises a gene expression cassette comprising a upstream-promoter, intron, and 5'-UTR, wherein the upstream-promoter, intron, and 5'-UTR is at least 80%, 85%, 90%, 91%, 92%, 93%, 94%, 95%, 96%, 97%, 98%, 99%, 99.5%, 99.8%, or 100% identical to SEQ ID NO:1. In an illustrative embodiment, a plant, plant tissue, or plant cell comprising a gene expression cassette comprising a upstream-promoter, intron, and 5'-UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, a plant, plant tissue, or plant cell comprises a gene expression cassette comprising a chimeric promoter operably linked to a transgene. Wherein, the chimeric promoter is comprised of an upstream-promoter, intron and 5'-UTR. The upstream-promoter, intron, and 5'-UTR can be operably linked to different transgenes within a gene expression cassette when a gene expression cassette includes two or more transgenes. In an illustrative embodiment, a gene expression cassette comprises an upstream-promoter, intron and 5'-UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, transgene expression using methods described herein is preferably expressed within a plant's root tissues. In an embodiment, transgene expression includes more than one transgene expressed in the plant's root tissues. In an embodiment, a method of growing a transgenic plant as described herein includes root-preferred transgene expression. In an embodiment, a method of expressing a transgene in a plant tissue or plant cell includes root-preferred tissues and root-preferred cells. In an embodiment, the root-preferred expression includes maize root-preferred expression.

In an embodiment, a plant, plant tissue, or plant cell comprises a vector comprising a chimeric gene promoter regulatory element as disclosed herein. In an embodiment, a plant, plant tissue, or plant cell comprises a vector comprising a chimeric gene promoter regulatory element as disclosed herein operably linked to a transgene. In an embodiment, a plant, plant tissue, or plant cell comprises a vector comprising a gene expression cassette as disclosed herein. In an embodiment, a vector can be a plasmid, a cosmid, a bacterial artificial chromosome (BAC), a bacteriophage, or a virus fragment.

In an embodiment, a plant, plant tissue, or plant cell according to the methods disclosed herein can be monocotyledons. The monocotyledon plant, plant tissue, or plant cell can be, but not limited to corn, rice, wheat, sugarcane, barley, rye, sorghum, orchids, bamboo, banana, cattails, lilies, oat, onion, millet, and triticale.

In an embodiment, a plant, plant tissue, or plant cell according to the methods disclosed herein can be dicotyledons. The dicotyledon plant, plant tissue, or plant cell can be, but not limited to rapeseed, canola, Indian mustard, Ethiopian mustard, soybean, sunflower, and cotton.

With regard to the production of genetically modified plants, methods for the genetic engineering of plants are well known in the art. For instance, numerous methods for plant transformation have been developed, including biological and physical transformation protocols for dicotyledonous plants as well as monocotyledonous plants (e.g., Goto-Fumiyuki et al., *Nature Biotech* 17:282-286 (1999); Miki et al., Methods in Plant Molecular Biology and Biotechnology, Glick, B. R. and Thompson, J. E. Eds., CRC Press, Inc., Boca Raton, pp. 67-88 (1993)). In addition, vectors and in vitro culture methods for plant cell or tissue transformation and regeneration of plants are available, for example, in Gruber et al., Methods in Plant Molecular Biology and Biotechnology, Glick, B. R. and Thompson, J. E. Eds., CRC Press, Inc., Boca Raton, pp. 89-119 (1993).

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed cells can also be identified by screening for the activities of any visible marker genes (e.g., the yfp, gfp, β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, 51 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) next generation sequencing (NGS) analysis; 5) protein gel electrophoresis, western blot techniques, immunoprecipitation, or enzyme-linked immunosorbent assay (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, Northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product. In addition, the levels of polypeptide expressed can be measured immunochemically, i.e., ELISA, RIA, EIA and other antibody based assays well known to those of skill in the art, such as by electrophoretic detection assays (either with staining or western blotting). As one non-limiting example, the detection of the AAD-1 (aryloxyalkanoate dioxygenase; see WO 2005/107437) and PAT (phosphinothricin-N-acetyltransferase) proteins using an ELISA assay is described in U.S. Patent Publication No. 20090093366 which is herein incorporated by reference in its entirety. The transgene may be selectively expressed in some cell types or tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed comprises the transgene or gene expression cassette. The present disclosure further encompasses the progeny, clones, cell lines or cells of the transgenic plants described above wherein said progeny, clone, cell line or cell comprise the transgene or gene construct.

While the invention has been described with reference to specific methods and embodiments, it will be appreciated that various modifications and changes may be made without departing from the invention.

EXAMPLES

Example 1: Novel Chimeric Gene Promoter Regulatory Elements

The chimeric promoter sequences are made up of an upstream-promoter polynucleotide sequence that was obtained from *Zea mays* Peroxidase 5 followed by the *Zea mays* alcohol dehydrogenase (I) intron 6 and Maize Streak Virus 5'-UTR. The 1,642 bp *Zea mays* Peroxidase 5 upstream promoter sequence (SEQ ID NO:2), is shown with underlining. The 117 bp Maize Streak Virus 5'-UTR (also referred to as a leader sequence) sequence (SEQ ID NO:3) is show in lower case font. The 341 bp *Zea mays* alcohol dehydrogenase (I) intron 6 sequence (SEQ ID NO:4) is italicized.

```
                                                  (SEQ ID NO: 1)
ACCACTGTTGTAACTTGTAAGCCACTAGCTCACGTTCTCCATGAGCTCTT

CTCTCTGCTGTTTCTTCCTCTGCTAACTGCGTTATGATATGACGTCGTAT

AAATAATCTCACAATACTTCCTTATTTTCAGCATGGCCTCTTTTATGTTT

ATTTAACAGTAGCAACCAACGCCGCTCGATGTTTCCTTCAAGAAACGGCC

ACTCACTATGTGGTGTGCAGAAGAACAAATGTAAGCAGCTCCTACAGGTA

CCAGTAGTCATGTCAGTGTGGAAGCTTTCCAACCAACGCCTCCTTCGAGG

AACCTGGTCGTGCTGACATGAATGTAGGCCATGCAAGCACAAGCACCTAA

CGCGAATCATCACGACGCGCCGTGTACTGGGCGTTGGTACATCACACCCC

GCGTTTGACCTGATCGGAAGCATGCGTGTGTGTTGGCTGCAGGACCGGCT

ATAGGTTTCCTGCATTGGACAGCAGAAGCCAGTCATGTTAGGCACTCACG

CGCTCCTGCCGTTTGATGAATCATCCGGTCTTTCGTATTGATCACTAGTT

CACTACGCTGATATAGCAAATTTTAAGATGTGAAACCACGAGACGAGCGA

TAAATCTTAGACGTTACCTATCCATATGAAGCTTGTGCGAAAAAAAGGCG

TGCCGCTGTAGCATCATTCGTATACACTTTTGTCCCCAAAGACAGGGATA

CGAATCCATGCTCGACAGAACCCTCCCTTCCCTGCAGATAACGACACTTA

AGTATAACAAAAGTAGTTGGATTATTTCAGAAGCAAAATCTCACTTTTCG

CTGGCCTTTTTGTACTTTGGTTACTTGAGTTCAGACAGTGTATGCTATAT

TGTCATGTGCTGCGTAAGGTTTAAATATGGTTCGACAAATATATCAGTAT

ATCACTACTTTGTTATGGGTGGGGCCTAGCACAAACTTGATACAGCTAGG

ATAAAGTTAGAACGATGACTGATCTACTGTAAAGCGACACCTGTCCTGTT

ATGGTAGTTTAAGTCCATTCCTGGACGACTCCAGATCCAGGATATGATGC

TGTTACATAATGCGATTGTTCACAATAAAATTGCATGATGTTCTTCTACT

CTTTAGGCAGTTTTGTTCAACAGGCAAGTTGCATAATGCATGTGCATATA

TGAGCAGCATAATCATCAATTAATCATAGGTTCGTCATTTTAGTTTCACT

CCTTCACATTATTCCAGCCCTTGAAGAAAATGTAGCAGTGCTTGCTGTT

TAATAAGTGGCAGAGCTGTTTTCACTCCACCTACGCTTGTCTAGGACCAA

AATTTTAATCTGTCACTTTGAGCTAAAACTGAAGCACCAAACCGCTACAA

AAGAACGTAGGAGCTGAATTGTAACTTGATGGGATTACTATAGCAGTTGC

TACAGTTCTAGCTAGCTACCTTATTCTATACGCATCACCCTAACAACCCG

GCTGACTGCTGCATCTGACCCCACCGTCCCCTGCTCCAAACCAACTCTCC

TTTCCTTGCATGCACTACACCCACTTCCTGCAGCTATATATACCACCATA

TGCCCATCTTATGAAACCATCCACAAGAGGAGAAGAAACAATCAACCAGC

AACACTCTTCTCTTATAACATAGTACAGCGAAGGTAACTCACGGTACCct gaaggctcgacaaggcagtccacggaggagctgatatttggtggacaagc tgtggataggagcaaccctatccctaatataccagcaccaccaagtcagg gcaatcccagatcaCCCCAGCAGATTCGAAGAAGGTACAGTACACACAC

ATGTATATATGTATGATGTATCCCTTCGATCGAAGGCATGCCTTGGTATA

ATCACTGAGTAGTCATTTTATTACTTTGTTTTGACAAGTCAGTAGTTCAT

CCATTTGTCCCATTTTTTCAGCTTGGAAGTTTGGTTGCACTGGCCTTGGT

CTAATAACTGAGTAGTCATTTTATTACGTTGTTTCGACAAGTCAGTAGCT

CATCCATCTGTCCCATTTTTTCAGCTAGGAAGTTTGGTTGCACTGGCCTT

GGACTAATAACTGATTAGTCATTTTATTACATTGTTTCGACAAGTCAGTA

GCTCATCCATCTGTCCCATTTTTCAGCTAGGAAGTTCGGATCTGGGCCA

TTTGTTCCAGGCACGGGATAAGCATTCAG
```

Example 2: Construct Design

Unless otherwise indicated, molecular biological and biochemical manipulations described in this and subsequent Examples were performed by standard methodologies as disclosed in, for example, Ausubel et al. (1995), and Sambrook et al. (1989), and updates thereof. The constructs used in the experiments (TABLE 1) are described in greater detail below.

Construct pDAS5144 (e.g. pDAB3620) was built containing two gene expression cassettes. The first gene expression cassette (SEQ ID NO:5) contained the *Zea mays* Peroxidase 5 upstream-promoter (International Patent App. No. 1998/056921) followed by the *Zea mays* alcohol dehydrogenase (I) intron 6 (Dennis et al., (1984) *Nucleic Acids Res.* 12:3983-4000) and Maize Streak Virus 5'-UTR (Mullineaux et al., (1984) *EMBO J.* 3:3063-3068) operably linked to the tcdA transgene (U.S. Patent App. No. 2009/0221501) and flanked by the *Zea mays* Peroxidase 5 3'-UTR (International Patent App. No. 1998/056921). The second gene expression cassette contained a selectable marker gene and was made up of the *Oryza sativa* Actin promoter (U.S. Pat. No. 6,429,357) operably linked to a phosphinothricin acetyl transferase (Wohlleben et al., (1988) *Gene* 70: 25-37) transgene and terminated by the *Zea mays* Lipase 3'-UTR (U.S. Pat. No. 7,179,902). This construct was mobilized into the Superbinary pSB1 binary vector (Japan Tobacco, Tokyo, JP). The constructs used to complete pDAS5144 were molecularly confirmed via restriction enzyme digestion and DNA sequencing.

```
                                                  (SEQ ID NO: 5)
TACAAAAAAGCAGGCTCCGCAAGCTTGCATGCCTGCAGATCCCCGGGGAT

CTCCGCGGGGCCCACCACTGTTGTAACTTGTAAGCCACTAGCTCACGTT

CTCCATGAGCTCTTCTCTCTGCTGTTTCTTCCTCTGCTAACTGCGTTATG

ATATGACGTCGTATAAATAATCTCACAATACTTCCTTATTTTCAGCATGG

CCTCTTTTATGTTTATTTAACAGTAGCAACCAACGCCGCTCGATGTTTCC

TTCAAGAAACGGCCACTCACTATGTGGTGTGCAGAAGAACAAATGTAAGC
```

-continued

AGCTCCTACAGGTACCAGTAGTCATGTCAGTGTGGAAGCTTTCCAACCAA
CGCCTCCTTCGAGGAACCTGGTCGTGCTGACATGAATGTAGGCCATGCAA
GCACAAGCACCTAACGCGAATCATCACGACGCGCCGTGTACTGGGCGTTG
GTACATCACACCCCGCGTTTGACCTGATCGGAAGCATGCGTGTGTGTTGG
CTGCAGGACCGGCTATAGGTTTCCTGCATTGGACAGCAGAAGCCAGTCAT
GTTAGGCACTCACGCGCTCCTGCCGTTTGATGAATCATCCGGTCTTTCGT
ATTGATCACTAGTTCACTACGCTGATATAGCAAATTTTAAGATGTGAAAC
CACGAGACGAGCGATAAATCTTAGACGTTACCTATCCATATGAAGCTTGT
GCGAAAAAAGGCGTGCCGCTGTAGCATCATTCGTATACACTTTTGTCCC
CAAAGACAGGGATACGAATCCATGCTCGACAGAACCCTCCCTTCCCTGCA
GATAACGACACTTAAGTATAACAAAAGTAGTTGGATTATTTCAGAAGCAA
AATCTCACTTTTCGCTGGCCTTTTTGTACTTTGGTTACTTGAGTTCAGAC
AGTGTATGCTATATTGTCATGTGCTGCGTAAGGTTTAAATATGGTTCGAC
AAATATATCAGTATATCACTACTTTGTTATGGGTGGGGCCTAGCACAAAC
TTGATACAGCTAGGATAAAGTTAGAACGATGACTGATCTACTGTAAAGCG
ACACCTGTCCTGTTATGGTAGTTTAAGTCCATTCCTGGACGACTCCAGAT
CCAGGATATGATGCTGTTACATAATGCGATTGTTCACAATAAAATTGCAT
GATGTTCTTCTACTCTTTAGGCAGTTTTGTTCAACAGGCAAGTTGCATAA
TGCATGTGCATATATGAGCAGCATAATCATCAATTAATCATAGGTTCGTC
ATTTTAGTTTCACTCCTTCACATTATTCCAGCCCTTGAAGAAAAATGTAG
CAGTGCTTGCTGTTTAATAAGTGGCAGAGCTGTTTTCACTCCACCTACGC
TTGTCTAGGACCAAAATTTTAATCTGTCACTTTGAGCTAAAACTGAAGCA
CCAAACCGCTACAAAAGAACGTAGGAGCTGAATTGTAACTTGATGGGATT
ACTATAGCAGTTGCTACAGTTCTAGCTAGCTACCTTATTCTATACGCATC
ACCCTAACAACCCGGCTGACTGCTGCATCTGACCCCACCGTCCCCTGCTC
CAAACCAACTCTCCTTTCCTTGCATGCACTACACCCACTTCCTGCAGCTA
TATATACCACCATATGCCCATCTTATGAAACCATCCACAAGAGGAGAAGA
AACAATCAACCAGCAACACTCTTCTCTTATAACATAGTACAGCGAAGGTA
ACTCACGGTACCCTGAAGGCTCGACAAGGCAGTCCACGGAGGAGCTGATA
TTTGGTGGACAAGCTGTGGATAGGAGCAACCCTATCCCTAATATACCAGC
ACCACCAAGTCAGGGCAATCCCCAGATCACCCCAGCAGATTCGAAGAAGG
TACAGTACACACATGTATATATGTATGATGTATCCCTTCGATCGAAGG
CATGCCTTGGTATAATCACTGAGTAGTCATTTTATTACTTTGTTTTGACA
AGTCAGTAGTTCATCCATTTGTCCCATTTTTTCAGCTTGGAAGTTTGGTT
GCACTGGCACTTGGTCTAATAACTGAGTAGTCATTTTATTACGTTGTTTC
GACAAGTCAGTAGCTCATCCATCTGTCCCATTTTTTCAGCTAGGAAGTTT
GGTTGCACTGGCCTTGGACTAATAACTGATTAGTCATTTTATTACATTGT
TTCGACAAGTCAGTAGCTCATCCATCTGTCCCATTTTTCAGCTAGGAAGT
TCGGATCTGGGCCATTTGTTCCAGGCACGGGATAAGCATTCAGCCATGG
CTAATGAGTCAGTCAAGGAGATCCCGGATGTTCTCAAATCCCAGTGTGGT
TTCAACTGCCTCACGGACATCTCCCACAGCTCATTCAATGAGTTCCGCCA

-continued

GCAAGTCTCTGAGCACCTCTCATGGTCGGAGACGCATGACCTCTACCACG
ATGCTCAGCAAGCCCAGAAAGACAACCGGCTGTATGAGGCACGGATCCTC
AAGAGGGCCAACCCGCAGCTCCAGAATGCGGTCCACCTCGCCATCCTTGC
TCCAAATGCGGAATTGATTGGCTACAATAACCAATTCTCGGGAAGGGCCT
CACAGTATGTTGCGCCTGGCACAGTTTCGTCCATGTTCAGCCCAGCAGCG
TACCTCACAGAGCTGTACAGAGAGGCGAGGAACCTTCATGCGTCTGACTC
CGTGTACTATCTGGACACACGCAGACCGGACCTGAAGTCAATGGCCCTCA
GCCAGCAAAACATGGACATTGAACTGTCCACCCTTTCCTTGAGCAATGAG
CTTCTGTTGGAATCCATCAAGACTGAGAGCAAGCTGGAAAACTACACAAA
GGTGATGGAGATGCTGTCCACCTTCAGACCATCTGGAGCGACTCCATACC
ACGATGCCTATGAGAATGTGAGGGAGGTCATTCAGCTTCAAGACCCTGGC
CTTGAGCAGCTCAATGCCAGCCCAGCCATTGCGGGACTGATGCACCAAGC
CTCCCTGCTTGGGATCAATGCCTCCATCAGCCCTGAGCTGTTCAACATCT
TGACTGAAGAGATCACTGAGGGCAATGCGGAGGAACTGTACAAGAAAAAC
TTCGGCAACATTGAGCCTGCCAGCCTTGCAATGCCGGAATACCTGAAACG
CTATTACAACTTGTCGGATGAGGAACTTTCGCAGTTCATTGGCAAAGCCT
CAAACTTTGGGCAGCAAGAGTACAGCAACAATCAGCTCATCACACCTGTT
GTGAACTCATCTGATGGCACTGTGAAGGTTTACCGCATCACAAGGGAGTA
CACCACAAATGCCTACCAGATGGATGTTGAACTGTTCCCGTTTGGAGGTG
AAAACTACCGGCTTGACTACAAGTTCAAGAACTTCTACAATGCATCCTAC
CTGTCGATCAAGCTGAACGACAAACGGGAGCTTGTGAGGACGGAAGGTGC
TCCCCAAGTGAACATTGAATACTCTGCCAACATCACACTCAACACAGCGG
ACATCAGCCAGCCGTTTGAAATTGGCTTGACCAGAGTGCTTCCCTCGGGC
TCCTGGGCCTATGCGGCAGCCAAGTTTACGGTTGAGGAGTACAACCAGTA
CAGCTTCCTCCTGAAGCTCAACAAGGCAATCCGGCTGAGCAGAGCCACTG
AGCTGTCACCCACCATCCTGGAGGGCATTGTGAGGTCTGTCAACCTTCAG
CTTGACATCAACACTGATGTGCTTGGCAAGGTGTTCCTGACCAAGTATTA
CATGCAGCGCTATGCCATCCATGCGGAGACGGCACTGATCCTCTGCAATG
CACCCATATCGCAGCGCTCGTATGACAACCAGCCCAGCCAGTTCGACAGA
CTCTTCAACACTCCCCTTCTGAACGGCCAGTACTTCAGCACTGGAGATGA
AGAGATTGACCTGAACTCTGGCTCGACGGGTGACTGGAGGAAAACCATCT
TGAAGAGGGCCTTCAACATTGATGACGTTTCCCTCTTCCGCCTTTTGAAG
ATCACAGATCACGACAACAAGGATGGCAAGATCAAGAACAATCTCAAGAA
CCTTTCCAACCTCTACATTGGCAAACTGCTTGCAGACATCCACCAGCTGA
CCATTGATGAGTTGGACCTGTTGCTGATTGCAGTTGGTGAGGGCAAGACC
AACCTCTCTGCAATCTCAGACAAAGTTGGCAACCCTCATCCGCAAGCT
GAACACGATCACAAGCTGGCTTCACACGCAGAAGTGGTCTGTTTTCCAAC
TGTTCATCATGACCAGCACGTCCTACAACAAGACCCTGACTCCGGAGATC
AAGAACCTTTTGGATACAGTCTATCATGGTCTCCAAGGCTTTGACAAGGA
CAAGGCGGACCTGCTTCATGTCATGGCACCCTACATTGCAGCCACACTCC
AGCTCTCCTCTGAAAATGTTGCCCACTCAGTGCTGTTGTGGGCTGACAAG

-continued

CTCCAGCCTGGGGATGGAGCCATGACTGCTGAGAAGTTCTGGGACTGGCT

CAACACGAAGTACACACCTGGCTCCTCTGAGGCAGTTGAGACTCAAGAAC

ACATTGTGCAGTACTGCCAAGCGCTTGCACAGTTGGAGATGGTTTACCAC

TCAACTGGCATCAACGAGAATGCCTTCCGCCTCTTTGTCACAAAGCCTGA

GATGTTTGGTGCTGCCACTGGAGCCGCTCCTGCCCATGATGCCCTGTCAC

TCATCATGTTGACGAGGTTTGCAGACTGGGTCAACGCCCTTGGTGAGAAA

GCCTCGTCTGTCCTGGCAGCCTTTGAAGCCAACTCCCTGACTGCGGAACA

GCTTGCGGATGCCATGAACCTTGATGCCAACTTGCTCCTGCAAGCTTCGA

TCCAAGCCCAGAACCATCAGCATTTGCCACCTGTCACGCCTGAAAATGCG

TTCTCATGCTGGACCTCCATCAACACCATACTCCAGTGGGTGAACGTGGC

GCAACAGCTCAATGTGGCACCTCAAGGAGTGTCAGCGCTGGTTGGGCTTG

ACTACATCCAGTCCATGAAGGAGACACCGACCTACGCGCAGTGGGAGAAT

GCAGCTGGCGTCTTGACAGCTGGTCTGAACTCACAGCAAGCCAACACGCT

GCATGCGTTCTTGGATGAGAGCCGCTCTGCTGCCCTCAGCACGTACTATA

TCCGGCAAGTTGCCAAGGCAGCGGCTGCCATCAAGTCTCGGGATGACCTC

TACCAGTACTTGCTCATTGACAATCAGGTTTCTGCTGCCATCAAAACGAC

CCGGATTGCTGAGGCCATAGCCAGCATCCAGCTCTACGTCAACAGAGCGC

TTGAGAACGTTGAAGAGAATGCCAACTCTGGAGTGATTTCTCGCCAGTTT

TTCATAGACTGGGACAAGTACAACAAGCGCTACTCCACCTGGGCTGGGGT

CTCTCAGCTTGTCTACTATCCTGAGAACTACATAGATCCGACGATGCGGA

TTGGCCAGACCAAGATGATGGATGCCCTCCTTCAGTCGGTGTCCCAGAGC

CAGCTCAATGCTGACACTGTGGAGGATGCCTTCATGAGCTACCTCACCTC

CTTCGAGCAAGTTGCCAACCTCAAGGTCATCTCTGCTTACCACGACAACA

TCAACAATGACCAAGGGCTCACCTACTTCATTGGCCTGTCTGAAACTGAT

GCGGGTGAGTATTACTGGCGCTCAGTGGACCACAGCAAGTTCAACGATGG

CAAGTTTGCTGCAAATGCCTGGTCTGAGTGGCACAAGATTGACTGCCCCA

TCAACCCGTACAAGTCCACCATCAGACCTGTCATCTACAAGAGCCGCTTG

TACTTGCTCTGGCTTGAGCAGAAGGAAATCACGAAGCAGACTGGCAACTC

CAAAGATGGCTACCAGACTGAGACGGACTACCGCTATGAGTTGAAACTTG

CTCACATCCGCTATGATGGTACATGGAACACTCCGATAACGTTTGATGTG

AACAAGAAGATTTCGGAGCTGAAACTGGAGAAGAACAGAGCGCCTGGGCT

CTACTGTGCTGGCTACCAAGGGGAAGATACGCTGTTGGTGATGTTCTACA

ACCAGCAAGACACCCTTGACTCGTACAAGAACGCTTCCATGCAAGGCCTC

TACATCTTTGCTGACATGGCTTCCAAAGACATGACTCCGGAGCAGAGCAA

TGTCTACCGGGACAACTCCTACCAGCAATTTGACACCAACAATGTTCGGA

GGGTCAATAACCGCTATGCGGAAGATTATGAGATCCCAAGCTCAGTGTCT

AGCCGCAAGGACTATGGCTGGGGAGACTACTATCTCAGCATGGTGTACAA

TGGTGACATACCCACGATCAACTACAAGGCTGCCTCCTCAGACCTGAAGA

TATACATCAGCCCCAAGCTCCGCATCATTCACAATGGCTATGAGGGCCAG

AAGAGGAACCAGTGCAACTTGATGAACAAGTATGGCAAACTTGGGGACAA

GTTCATTGTCTACACCTCGCTTGGTGTGAACCCGAACAATTCCTCGAACA

-continued

AGCTCATGTTCTACCCGGTCTACCAGTACAGCGGCAACACCTCTGGCTTG

AACCAAGGGGAGGCTCCTGTTCCACAGAGACACCACGTACCCGAGCAAGGT

GGAGGCGTGGATTCCTGGTGCCAAAAGGTCACTCACCAACCAGAATGCAG

CCATTGGTGATGACTATGCCACAGACAGCCTGAACAAGCCTGATGACCTG

AAGCAGTACATCTTCATGACTGACTCCAAGGGCACAGCCACTGATGTGTC

TGGTCCGGTGGAGATCAACACTGCAATCAGCCCAGCCAAGGTCCAAATCA

TTGTCAAAGCTGGTGGCAAGGAACAGACCTTCACAGCTGACAAAGATGTG

AGCATCCAGCCAAGCCCCTCCTTTGATGAGATGAACTACCAGTTCAACGC

TCTTGAAATTGATGGCTCGGGACTCAACTTCATCAACAATTCGGCTTCAA

TTGATGTGACGTTCACTGCCTTTGCGGAGGATGGGAGGAAATTGGGCTAT

GAGAGCTTCTCAATACCAGTCACCTTGAAGGTTTCCACTGACAATGCACT

CACGCTTCATCACAACGAGAATGGAGCGCAGTACATGCAATGGCAGAGCT

ACCGCACAAGGTTGAACACCCTCTTTGCAAGGCAACTTGTGGCCAGAGCC

ACGACTGGCATTGACACCATACTCAGCATGGAAACGCAGAACATCCAAGA

GCCACAGTTGGGCAAGGGTTTCTATGCCACCTTTGTGATCCCACCCTACA

ACCTGTCAACGCATGGTGATGAGCGCTGGTTCAAGCTGTACATCAAGCAC

GTGGTTGACAACAATTCCCACATCATATACTCGGGTCAGCTCACTGACAC

GAACATCAACATCACCCTGTTCATCCCACTTGATGACGTTCCCCTGAACC

AAGACTACCATGCCAAGGTCTACATGACCTTCAAGAAATCACCGTCAGAT

GGCACCTGGTGGGACCGCACTTCGTTCGGGATGACAAAGGCATTGTCAC

AATCAACCCCAAGTCCATACTCACCCACTTTGAGTCTGTGAATGTTCTGA

ATAACATCCTCAGAGCCGATGGACTTCTCGGGTGCCAACTCCCTGTAC

TTCTGGGAGTTGTTCTATTACACGCCGATGCTTGTGGCGCAGAGGTTGCT

CCATGAACAGAACTTTGATGAGGCCAACCGCTGGCTCAAGTATGTCTGGA

GCCCCTCGGGTTACATTGTGCATGGCCAGATCCAGAACTACCAATGGAAT

GTTCGCCCATTGCTTGAGGACACCTCCTGGAACTCTGACCCCCTTGACTC

GGTGGACCCTGATGCGGTGGCTCAGCATGACCCCATGCACTACAAGGTCT

CAACCTTCATGAGGACCCTGGACCTTCTGATTGCCAGAGGAGACCATGCT

TACCGCCAATTGGAACGGGACACACTGAATGAGGCAAAGATGTGGTACAT

GCAAGCTCTGCACCTCTTGGGAGACAAGCCGTACCTCCCGCTCAGCACCA

CATGGTCAGACCCAAGGTTGGACAGAGCAGCTGACATCACAACTCAGAAT

GCTCATGACTCTGCCATTGTGGCTCTGAGGCAGAACATCCCAACACCTGC

GCCACTGTCGCTGAGATCTGCGAACACCCTGACAGACCTGTTCCTCCCCC

AGATCAATGAGGTCATGATGAACTACTGGCAAACCTTGGCGCAGCGGGTC

TACAACCTCCGCCACAACCTCTCCATTGATGGGCAGCCGCTGTACCTCCC

AATCTATGCCACACCAGCTGACCCAAAGGCGCTTCTCAGCGCAGCTGTGG

CCACGAGCCAAGGGGAGGCAAGCTCCCTGAGAGCTTCATGTCGCTCTGG

AGGTTTCCCCACATGTTGGAGAATGCCAGAGGCATGGTGAGCCAACTGAC

TCAGTTTGGCTCGACGCTCCAGAACATCATTGAGAGGCAAGATGCAGAGG

CTCTGAATGCGTTGCTCCAGAATCAAGCAGCTGAGTTGATCCTGACGAAC

CTGTCAATCCAAGACAAGACCATTGAGGAACTTGATGCGGAAAAGACAGT

-continued
CCTTGAAAAGAGCAAGGCTGGAGCCCAAAGCCGGTTCGACTCATATGGCA

AGCTGTATGATGAGAACATCAATGCTGGGGAGAATCAAGCCATGACCCTG

AGGGCTTCAGCAGCGGGTCTGACCACGGCAGTGCAAGCGTCTCGCTTGGC

TGGGGCTGCGGCTGACCTCGTTCCCAACATCTTTGGGTTTGCTGGTGGCG

GATCAAGGTGGGGAGCCATTGCAGAAGCAACGGGCTATGTGATGGAGTTC

TCTGCCAATGTCATGAACACTGAGGCAGACAAAATCAGCCAATCGGAGAC

CTACAGACGGAGACGGCAAGAATGGGAGATACAAAGGAACAATGCAGAGG

CAGAACTGAAGCAAATAGATGCCCAACTGAAGTCCTTGGCTGTCAGAAGG

GAGGCTGCGGTCCTCCAAAAGACCTCCCTCAAGACCCAGCAAGAGCAAAC

CCAGTCCCAGTTGGCGTTCCTCCAGAGGAAGTTCTCGAACCAAGCGCTGT

ACAACTGGCTGAGGGGAAGGTTGGCAGCCATCTACTTCCAGTTCTATGAC

CTTGCTGTGGCCAGATGCCTCATGGCGGAACAAGCCTACCGCTGGGAACT

GAATGATGACTCTGCCAGATTCATCAAACCGGGTGCATGGCAAGGCACAT

ATGCTGGACTCCTTGCTGGGGAGACACTCATGCTCTCATTGGCCCAGATG

GAGGATGCTCACCTCAAACGGGACAAGAGGGCTCTGGAAGTGGAGCGGAC

AGTCAGCCTTGCGGAGGTCTATGCGGGACTGCCCAAAGACAATGGACCAT

TTTCGTTGGCGCAAGAGATAGACAAGTTGGTCAGCCAAGGGTCTGGATCA

GCGGGTTCTGGAAACAACAATCTGGCGTTCGGTGCTGGCACTGACACCAA

GACGTCCCTCCAAGCCTCAGTCTCCTTTGCTGACCTGAAGATAAGGGAGG

ACTACCCAGCGTCCCTTGGGAAGATCAGACGCATCAAGCAGATTTCAGTG

ACCCTGCCAGCTCTTCTGGGTCCATACCAAGATGTTCAAGCGATCCTCTC

CTATGGGACAAGGCTGGTTTGGCGAATGGCTGTGAGGCCCTTGCTGTGT

CACATGGCATGAATGACTCTGGGCAGTTCCAGCTTGATTTCAACGATGGC

AAGTTCCTGCCATTCGAGGGCATAGCCATTGATCAAGGCACCCTGACCCT

CTCCTTCCCCAATGCTTCGATGCCAGAGAAGGGAAAACAAGCCACCATGC

TCAAGACCCTGAATGATATCATACTCCACATCCGCTACACCATCAAGTGA

GTAGTTAGCTTAATCACCTAGAGCTCGTTTAAACTGAGGGCACTGAAGTC

GCTTGATGTGCTGAATTGTTTGTGATGTTGGTGGCGTATTTTGTTTAAAT

AAGTAAGCATGGCTGTGATTTTATCATATGATCGATCTTTGGGGTTTTAT

TTAACACATTGTAAAATGTGTATCTATTAATAACTCAATGTATAAGATGT

GTTCATTCTTCGGTTGCCATAGATCTGCTTATTTGACCTGTGATGTTTTG

ACTCCAAAAACCAAAATCACAACTCAATAAACTCATGGAATATGTCCACC

TGTTTCTTGAAGAGTTCATCTACCATTCCAGTTGGCATTTATCAGTGTTG

CAGCGGCGCTGTGCTTTGTAACATAACAATTGTTACGGCATATATCCAAC

GGCCGGCCTAGGCCACGGTGGCCAGATCCACTAGAGGCGCGCCTCTAGTT

CTAGAGCGGCCGCTTAATTCACTGGCCGTCGTTTTACAACGTCGTGACTG

GGAAAACCCTGGCGTTACCCAACTTAATCGCCTTGCAGCACATCCCCCTT

TCGCCAGCTGGCGTAATAGCGAAGAGGCCCGCACCGATCGCCCTTCCCAA

CAGTTGCAAATGGCGCGCCGACCCAGCTTTC

Construct pDAS5128 (e.g. pDAB3619) was built containing two gene expression cassettes. The first gene expression cassette (SEQ ID NO:6) contained the Zea mays Ubiquitin 1 promoter (Christensen et al., (1992) *Plant Molecular Biology* 18; 675-689) followed by the Zea mays alcohol dehydrogenase (I) intron 6 (Dennis et al., (1984) *Nucleic Acids Res.* 12:3983-4000) and Maize Streak Virus 5'-UTR (Mullineaux et al., (1984) *EMBO J.* 3:3063-3068) operably linked to the tcdA transgene (U.S. Patent App. No. 2009/0221501) and flanked by the Zea mays Peroxidase 5 3'-UTR (International Patent App. No. 1998/056921). The second gene expression cassette contained a selectable marker gene and was made up of the Oryza sativa Actin promoter (U.S. Pat. No. 6,429,357) operably linked to a phosphinothricin acetyl transferase (Wohlleben et al., (1988) *Gene* 70: 25-37) transgene and terminated by the Zea mays Lipase 3'-UTR (U.S. Pat. No. 7,179,902). This construct was mobilized into the Superbinary pSB1 binary vector (Japan Tobacco, Tokyo, JP). The constructs used to complete pDAS5128 were molecularly confirmed via restriction enzyme digestion and DNA sequencing. The novel Zea mays Ubiquitin 1 promoter followed by the Zea mays alcohol dehydrogenase (I) intron 6 and Maize Streak Virus 5'-UTR is disclosed herein as SEQ ID NO:7.

(SEQ ID NO: 6)
GTGCAGCGTGACCCGGTCGTGCCCCTCTCTAGAGATAATGAGCATTGCAT
GTCTAAGTTATAAAAAATTACCACATATTTTTTTTGTCACACTTGTTTGA
AGTGCAGTTTATCTATCTTTATACATATATTTAAACTTTACTCTACGAAT
AATATAATCTATAGTACTACAATAATATCAGTGTTTTAGAGAATCATATA
AATGAACAGTTAGACATGGTCTAAAGGACAATTGAGTATTTTGACAACAG
GACTCTACAGTTTTATCTTTTTAGTGTGCATGTGTTCTCCTTTTTTTTTG
CAAATAGCTTCACCTATATAATACTTCATCCATTTTATTAGTACATCCAT
TTAGGGTTTAGGGTTAATGGTTTTTATAGACTAATTTTTTTAGTACATCT
ATTTTATTCTATTTTAGCCTCTAAATTAAGAAAACTAAAACTCTATTTTA
GTTTTTTTATTTAATAGTTTAGATATAAAATAGAATAAAATAAAGTGACT
AAAAATTAAACAAATACCCTTTAAGAAATTAAAAAAACTAAGGAAACATT
TTTCTTGTTTCGAGTAGATAATGCCAGCCTGTTAAACGCCGTCGACGAGT
CTAACGGACACCAACCAGCGAACCAGCAGCGTCGCGTCGGGCCAAGCGAA
GCAGACGGCACGGCATCTCTGTCGCTGCCTCTGGACCCCTCTCGAGAGTT
CCGCTCCACCGTTGGACTTGCTCCGCTGTCGGCATCCAGAAATTGCGTGG
CGGAGCGGCAGACGTGAGCCGGCACGGCAGGCGGCCTCCTCCTCCTCTCA
CGGCACCGGCAGCTACGGGGGATTCCTTTCCCACCGCTCCTTCGCTTTCC
CTTCCTCGCCCGCCGTAATAAATAGACACCCCCTCCACACCCTCTTTTCC
CAACCTCGTGTTGTTCGGAGCGCACACACACACAACCAGATCTCCCCCAA
ATCCACCCGTCGGCACCTCCGCTTCAAGGGTACCCTGAAGGCTCGACAAG
GCAGTCCACGGAGGAGCTGATATTTGGTGGACAAGCTGTGGATAGGAGCA
ACCCTATCCCTAATATACCAGCACCACCAAGTCAGGGCAATCCCCAGATC
ACCCCAGCAGATTCGAAGAAGGTACAGTACACACACATGTATATATGTAT
GATGTATCCCTTCGATCGAAGGCATGCCTTGGTATAATCACTGAGTAGTC
ATTTTATTACTTTGTTTTGACAAGTCAGTAGTTCATCCATTTGTCCCATT
TTTTCAGCTTGGAAGTTTGGTTGCACTGGCACTTGGTCTAATAACTGAGT
AGTCATTTTATTACGTTGTTTCGACAAGTCAGTAGCTCATCCATCTGTCC
CATTTTTTCAGCTAGGAAGTTTGGTTGCACTGGCCTTGGACTAATAACTG
ATTAGTCATTTTATTACATTGTTTCGACAAGTCAGTAGCTCATCCATCTG
TCCCATTTTTCAGCTAGGAAGTTCGGATCTGGGGCCATTTGTTCCAGGCA
CGGGATAAGCATTCAGCCATGGCTAATGAGTCAGTCAAGGAGATCCCGGA
TGTTCTCAAATCCCAGTGTGGTTTCAACTGCCTCACGGACATCTCCCACA
GCTCATTCAATGAGTTCCGCCAGCAAGTCTCTGAGCACCTCTCATGGTCG
GAGACGCATGACCTCTACCACGATGCTCAGCAAGCCCAGAAAGACAACCG
GCTGTATGAGGCACGGATCCTCAAGAGGGCCAACCCGCAGCTCCAGAATG
CGGTCCACCTCGCCATCCTTGCTCCAAATGCGGAATTGATTGGCTACAAT
AACCAATTCTCGGGAAGGGCCTCACAGTATGTTGCGCCTGGCACAGTTTC
GTCCATGTTCAGCCCAGCAGCGTACCTCACAGAGCTGTACAGAGAGGCGA
GGAACCTTCATGCGTCTGACTCCGTGTACTATCTGGACACACGCAGACCG
GACCTGAAGTCAATGGCCCTCAGCCAGCAAAACATGGACATTGAACTGTC
CACCCTTTCCTTGAGCAATGAGCTTCTGTTGGAATCCATCAAGACTGAGA
GCAAGCTGGAAAACTACACAAAGGTGATGGAGATGCTGTCCACCTTCAGA
CCATCTGGAGCGACTCCATACCACGATGCCTATGAGAATGTGAGGGAGGT
CATTCAGCTTCAAGACCCTGGCCTTGAGCAGCTCAATGCCAGCCCAGCCA
TTGCGGGACTGATGCACCAAGCCTCCCTGCTTGGGATCAATGCCTCCATC
AGCCCTGAGCTGTTCAACATCTTGACTGAAGAGATCACTGAGGGCAATGC
GGAGGAACTGTACAAGAAAAACTTCGGCAACATTGAGCCTGCCAGCCTTG
CAATGCCGGAATACCTGAAACGCTATTACAACTTGTCGGATGAGGAACTT
TCGCAGTTCATTGGCAAAGCCTCAAACTTTGGGCAGCAAGAGTACAGCAA
CAATCAGCTCATCACACCTGTTGTGAACTCATCTGATGGCACTGTGAAGG
TTTACCGCATCACAAGGGAGTACACCACAAATGCCTACCAGATGGATGTT
GAACTGTTCCCGTTTGGAGGTGAAAACTACCGGCTTGACTACAAGTTCAA

```
GAACTTCTACAATGCATCCTACCTGTCGATCAAGCTGAACGACAAACGGG
AGCTTGTGAGGACGGAAGGTGCTCCCCAAGTGAACATTGAATACTCTGCC
AACATCACACTCAACACAGCGGACATCAGCCAGCCGTTTGAAATTGGCTT
GACCAGAGTGCTTCCCTCGGGCTCCTGGGCCTATGCGGCAGCCAAGTTTA
CGGTTGAGGAGTACAACCAGTACAGCTTCCTCCTGAAGCTCAACAAGCA
ATCCGGCTGAGCAGAGCCACTGAGCTGTCCACCCACCATCCTGGAGGGCAT
TGTGAGGTCTGTCAACCTTCAGCTTGACATCAACACTGATGTGCTTGGCA
AGGTGTTCCTGACCAAGTATTACATGCAGCGCTATGCCATCCATGCGGAG
ACGGCACTGATCCTCTGCAATGCACCCATATCGCAGCGCTCGTATGACAA
CCAGCCCAGCCAGTTCGACAGACTCTTCAACACTCCCCTTCTGAACCGCC
AGTACTTCAGCACTGGAGATGAAGAGATTGACCTGAACTCTGGCTCGACG
GGTGACTGGAGGAAAACCATCTTGAAGAGGGCCTTCAACATTGATGACGT
TTCCCTCTTCCGCCTTTTGAAGATCACAGATCACGACAACAAGGATGGCA
AGATCAAGAACAATCTCAAGAACCTTTCCAACCTCTACATTGGCAAACTG
CTTGCAGACATCCACCAGCTGACCATTGATGAGTTGGACCTGTTGCTGAT
TGCAGTTGGTGAGGGCAAGACCAACCTCTCTGCAATCTCAGACAAACAGT
TGGCAACCCTCATCCGCAAGCTGAACACGATCACAAGCTGGCTTCACACG
CAGAAGTGGTCTGTTTTCCAACTGTTCATCATGACCAGCACGCTCCTACAA
CAAGACCCTGACTCCGGAGATCAAGAACCTTTTGGATACAGTCTATCATG
GTCTCCAAGGCTTTGACAAGGACAAGGCGGAACCTGCTTCATGTCATGGCA
CCCTACATTGCAGCCACACTCCAGCTCTCCTCTGAAAATGTTGCCCACTC
AGTGCTGTTGTGGGCTGACAAGCTCCAGCCTGGGGATGGAGCCATGACTG
CTGAGAAGTTCTGGGACTGGCTCAACACGAAGTACACACCTGGCTCCTCT
GAGGCAGTTGAGACTCAAGAACACATTGTGCAGTACTGCCAAGCGCTTGC
ACAGTTGGAGATGGTTTACCACTCAACTGGCATCAACGAGAATGCCTTCC
GCCTCTTTGTCACAAAGCCTGAGATGTTTGGTGCTGCCACTGGAGCCGCT
CCTGCCCATGATGCCCTGTCACTCATCATGTTGACGAGGTTTGCAGACTG
GGTCAACGCCCTTGGTGAGAAAGCCTCGTCTGTCCTGGCAGCCTTTGAAG
CCAACTCCCTGACTGCGGAACAGCTTGCGGATGCCATGAACCTTGATGCC
AACTTGCCTGCAAGCTTCGATCCAAGCCCAGAACCATCAGCATTTGCC
ACCTGTCACGCCTGAAAATGCGTTCTCATGCTGGACCTCCATCAACACCA
TACTCCAGTGGGTGAACGTGGCCAACAGCTCAATGTGGCACCTCAAGGA
GTGTCAGCGCTGGTTGGGCTTGACTACATCCAGTCCATGAAGGAGACACC
GACCTACGCGCAGTGGGAGAATGCAGCTGGCGCTCTTGACAGCTGGTCTGA
ACTCACAGCAAGCCAACACGCTGCATGCGTTCTTGGATGAGAGCCGCTCT
GCTGCCCTCAGCACGTACTATATCCGGCAAGTTGCCAAGGCAGCGGCTGC
CATCAAGTCTCGGGATGACCTCTACCAGTACTTGCTCATTGACAATCAGG
TTTTCTGCTGCCATCAAAACGACCCGGATTGCTGAGGCCATAGCCAGCATC
CAGCTCTACGTCAACAGAGCGCTTGAGAACGCTTGAAGAGAATGCCAACTC
TGGAGTGATTTCTCGCCAGTTTTTCATAGACTGGGACAAGTACAACAAGC
GCTACTCCACCTGGGCTGGGGTCTCTCAGCTTGTCTACTATATCCTGAGAAC
TACATAGATCCGACGATGCGGATTGGCCAGACCAAGATGATGGATGCCCT
CCTTCAGTCGGTGTCCCAGAGCCAGCTCAATGCTGACACTGTGGAGAGATG
CCTTCATGAGCTACCTCACCTCCTTCGAGCAAGTTGCCAACCTCAAGGTC
ATCTCTGCTTACCACGACAACATCAACAATGACCAAGGGCTCACCTACTT
CATTGGCCTGTCTGAAACTGATGCGGGTGAGTATTACTGGCGCTCAGTGG
ACCACAGCAAGTTCACCAAGTTTTGCTGCAAGTCACTGGTCTGAG
TGGCACAAGATTGACTGCCCCATCAACCCGTACAAGTCCACCATCAGACC
TGTCATCTACAAGAGCCGCTTGTACTTGCTCTGGCTTGAGCAGAAGGAAA
TCACGAAGCAGACTGGCAACTCCAAAGATGGCTACCAGACTGAGACGGAC
TACCGCTATGAGTTGAAACTTGCTCACATCACGCTATGATGGTACATGGAA
CACTCCGATAACGTTTGATGTGAACAAGAAGATTTCGGAGCTGAAACTGG
AGAAGAACAGAGCGCCTGGGCTCTACTGTGCTGGCTACCAAGGGGAAGAT
ACGCTGTTGGTGATGTTCTACAACCAGCAAGACACCCTTGACTCGTACAA
GAACGCTTCCATCGCAAGGCCTCTACATCTTTGCTGACATGGCTTCCAAAG
ACATGACTCCGGAGACAGAGCAATGTCTACCGGACAATCCTACCAGCAA
TTTGACACCAACAATGTTCGGAGGGTCAATAACCGCTATGCGGAAGATTA
TGAGATCCCAAGCTCAGTGTCTAGCCGCAAGGACTATGGCTGGGGAGACT
ACTATCTCAGCATGGTGTGACAATGGTGACATACCCACGATCACTACAAG
GCTGCCTCCTCAGACCTGAAGATACACATCAGCCCCAAGCTCCGACATCAT
TCACAATGGCTATGAGGGCCAGAAGAGGAACCAGTGCAACTTGATGAACA
AGTATGGCAAACTTGGGGACAAGTTCATTGTCTACACCTCGCTTGGTGTG
AACCCGAACAATTCCTCGAACAAGCTCATGTTCTACCCGGTCTACCAGTA
CAGCGGCAACACCTCTGGCTTGAACAAGGGAGGCTCCTGTTCCACAGAG
ACACCACGTACCCGAGCAAGGTGGAGGCGTGGATTCCTGGTGCCAAAAGG
TCACTCACCAACCAGAATCAGCCATTGGTGATGACTATGCCACAGACAG
CCTGAACAAGCCTGATGACCTGAAGCAGTACATCTTCATGACTGACTCCA
AGGGCACAGCCAATGATGTCTGGTCCGGTGGAGATCAACACTGCAATC
AGCCCAGCCAAGGTCCAAATCATTGTCAAAGCTGGTGGCAAGGAACAGAC
CTTCACAGCTGACAAAGATGTGAGCATCCAGCCAAGCCCCTCCTTTGATG
AGATGAACTACCAGTTCAACGCTCTTGAAATTGATGGCTCGGGACTCAAC
TTCATCAACAATTCGGCTTCAATTGATGTGACAGTTCACTGCCTTTGCGGA
GGATGGGAGGAAATTGGGCTATGAGAGCTTCTCAATACACAGTCACCTTGA
AGGTTTCCACTGACAATGCACTCACGCTTCATCACACAGAGAATGGAGCGC
CAGTACATGCAATGGCAGAGCTACCGCACAAGGTTGAACACCCTCTTGC
AAGGCACTTGTGCCAGAGCCACGATGGCATTGACACCATCTCAGCA
TGGAAACGCAGAACATCCAAGAGCCACAGTTGGGCAAGGGTTTCTATGCC
ACCTTTGTGATCCCACCCTACAACCTGTCAACGCATGGTGATGAGCGCTG
GTTCAAGCTGTACATCAAGCACGTGGTTGACAACAATTCCCACATCATAT
ACTCGGGTCAGCTCACTGACACGGAACATCAACATCACCCTGTTCATCCCA
CTTGATGACGTTCCCCTGAACCAAGACTACCATGCCAAGGTCTACATGAC
CTTCAAGAAATCACCGTCAGATGGCACCTGGTGGGGACCGCACTTCGTTC
GGGATGACAAAGGCATTGTCACAATCAACCCCAAGTCCATACTCACCCAC
TTTGAGTCTGTGAATGTTCTGAATAACATCTCCTCAGAGCCGATGGACTT
CTCGGGTGCCAACTCCCTGTACTTCTGGGAGTTGTTCTATTACACGCCGA
TGCTTGTGGCGCAGAGGTTGCCATGAACAGAACTTTGATGAGGCCAAC
CGCTGGCTCAAGTATGTCTGGAGCCCCTCGGGTTACATTGTGCATGGCCA
GATCCTGCAGAACTACCAATGGAATGTTCGCCCATTGCTTGAGGACACCTCCT
GGAACTCTGACCCCCTTGACTCGGTGGACCCTGATGCGGTGGCTCAGCAT
GACCCCATGCACTACAAGGTCTCAACCTTCATGAGGACCCTGGACCTTCT
GATTGCTCAGAGGAGACCATGCTTACCGCCAATTGGAACGGGACACTGA
ATGAGGCAAAGATGTGGTACATGCAAGCTCTGCACCTCTTGGGAGACAAG
CCGTACCTCCCGCTCAGCACCACATGGTCAGACCCAAGGTTGGACAGAGC
AGCTGACATCACAACTCAGAATGCTCATGACTCTGCCATTGTGGCTCTGA
GGCAGAACATCCCAACCTGCGCCACTGTCGCTGAGATCTGCGAACACC
CTGACAGACCTGTTCCTCCCCAGATCAATGAGGTCATGATGAACTACTG
GCAAACCTTGGCGCAGCGGGTCTACAACCTCCGCCACACCTCTCCATTG
ATGGGCAGCCGCTGTACCTCCCAATCTATGCCACACCAGCTGACCCAAAG
GCGCTTCCAGCGCAGCTGTGGCCAGCAGCCAAGGGGAGGCAAGCTCCC
TGAGAGCTTCATGTCGCTCTGGAGGTTTCCCCACATGTTGGAGAATGCCA
GAGGCATGGTGAGCCAACTGACTCAGTTTGGCTCGACGTCCAGAACATC
ATTGAGAGGCAAGATGCAGAGGCTCTGAATGCGTTGCTCCAGAATCAAGC
AGCTGAGTTGATCCTGACGAACCTGTCAATCCAAGACAAGACCATTGAAG
AACTTGATGCGGAAAAGACAGTCCTTGAAAAGAGCAAGGCTGGAGCCCAA
AGCCGGTTCGACTCATATGGCAAGCTGTATGATGAGAACATCAATGCTGG
GGAGAATCAAGCCATGACCCTGAGGGCTTCAGCAGCGGGTCTGACCACGG
CAGTGCAAGCGTCTCGCTTGCTGGGGGCTGCGGCTGACCTCGTTCCCAAC
ATCTTTGGGTTGCTGGTGGCGGATCAAGGTGGGAGCCATTGCAGAAGC
AACGGGCTATGTGATGGAGTTCTCTGCCAATGTCATGAACACTGAGGCAG
ACAAAATCAGCCAATCGGAGACCTACAGACGGAGACGGCAAGAATGGGAG
ATACAAAGGAACAATGCAGAGGCAGAACTGAAGCAAATAGATGCCAACT
GAAGTCCTTGGCTGTCAGAAGGGAGGCTGCGGTCCTCCAAAAGACCTCCC
TCAAGACCCAGCAAGAGCAAACCCAGTCCCAGTTGGCGTTCCTCCAGAGG
AAGTTCTCGAACCAAGCGCTGTACAACTGGCTGAGGGGAAGGTTGGCAGC
CATCTACTTCCAGTTCTATGACCTTGCTGTGGCCAGATGCCTCATGCGG
AACAAGCCTACCGCTGGGAACTGAATGATGACTCTGCCAGATTCATCAAA
CCGGGTGCATGGCAAGGCACATATGCTGGACTCCTTGCTGGGGAGACACT
CATGCTCTCATTGGCCCAGATGGAGGATGCTCACCTCAAACGGGACAAGA
GGGCTCTGGAAGTGGAGCGGACAGTCAGCCTTGCGGAGGTCTATGCGGGA
CTGCCCAAAGACAATGACCCATTTTCGTTGGCGCAAGAGATAGACAAGTT
GGTCAGCCAAGGGTCTGGATCAGCGGGTTCTGGAAACAACAATCTGGCGT
TCGGTGCTGGCACTGACACCAAGACGTCCCTCCAAGCCTCAGTCTCCTTT
GCTGACCTGAAGATAAGGGAGGACTACCCAGCGTCCCTTGGGAAGATCAG
ACGCATCAAGCAGATTTCAGTGACCCTGCCAGCTCTTCTGGGTCCATACC
AAGATGTTCAAGCGATCCTCTCCTATGGGACAAGGCTGGTTTGGCGAAT
GGCTGTGAGGCCCTTGCTGTGTCACATGGCATGAATGACTCTGGGCAGTT
CCAGCTTGATTTCAACGATGGCAAGTTCCTGCCATTCGAGGGCATAGCCA
TTGATCAAGGCACCCTGACCTCTCCTTCCCCAATGCTTCGATGCAGAG
AAGGGAAAACAAGCCACCATGCTCAAGACCCTGAATGATATCATACTCCA
CATCCGCTACACCATCAAGTGAGTAGTTAGCTTAATCACCTAGAGCTCGT
TTAAACTGAGGGCACTGAAGTCGCTTGATGTGCTGAATTGTTTGTGATGT
TGGTGGCGTATTTTGTTAAATAAGTAAGCATGGCTGTGATTTTATCATA
TGATCGATCTTTGGGGTTTTATTTAACACATTGTAAAATGTGTATCTATT
AATAACTCAATGTATAAGATGTGTTCATTCTTCGGTTGCCATAGATCTGC
TTATTTGACCTGTGATGTTTTGACTCCAAAAACCAAAATCACAACTCAAT
AAACTCATGGAATATGTCCACCTGTTTCTTGAAGAGTTCATCTACCATTC
CAGTTGGCATTTATCAGTGTTGCAGCGGCGCTGTGCTTTGTAACATAACA
ATTGTTACGGCATATATCCAA (SEQ ID NO: 7)
GTGCAGCGTGACCCGGTCGTGCCCCTCTCTAGAGATAATGAGCATTGCAT
GTCTAAGTTATAAAAAATTACCACATATTTTTTTTGTCACACTTGTTTGA
AGTGCAGTTTATCTATCTTTATACATATATTTAAACTTTACTCTACGAAT
AATATAATCTATAGTACTACAATAATATCAGTGTTTTAGAGAATCATATA
AATGAACAGTTAGACATGGTCTAAAGGACAATTGAGTATTTTGACAACAG
GACTCTACAGTTTTATCTTTTTAGTGTGCATGTGTTCTCCTTTTTTTTTG
CAAATAGCTTCACCTATATAATACTTCATCCATTTTATTAGTACATCCAT
TTAGGGTTTAGGGTTAATGGTTTTTATAGACTAATTTTTTTAGTACATCT
ATTTTATTCTATTTTAGCCTCTAAATTAAGAAAACTAAAACTCTATTTTA
GTTTTTTTATTTAATAGTTTAGATATAAAAATAGAATAAAATAAAGTGACT
AAAATTAAACAAATACCCTTTAAGAAATTAAAAAAACTAAGGAAACATT
TTTCTTGTTTCGAGTAGATAATGCCAGCCTGTTAAACGCCGTCGACGAGT
CTAACAGACACCAACCAGCGAACCAGCGTCGCGTCGGGCCAAGAA
GCAGACGGCAGGCATCTCTGTCGCTGCCTCTGACCCCCTCTCGAGAGTT
CCGCTCCACCGTTGGACTTGCTCCGCTGTCGGCATCCAGAAATTGCGTGG
CGGAGCGGCAGACGTGAGCCGGCACGGCAGGCGGCCTCCTCCTCCTCTCA
CGGCACCGGCAGCTACGGGGGATTCCTTTCCCACCGCTCCTTCGCTTTCC
CTTCCTGCCCGCCTGTAATAAATAGACACCCCCTCCACACCCTCTTTCCC
CAACCTCGTGTTGTTCGGAGCGCACACACACACACAACCAGATCTCCCCA
ATCCACCCGTCGGCACCTCCGCTTCAAGGGTACCCTGAAGGCTCGACAAG
GCAGTCCACGGAGGAGCTGATATTTGGTGGACAAGCTGTGGATAGGAGCA
ACCCTATCCCTAATATACCAGCACCACCAAGTCAGGGCAATCCCCAGATC
```

-continued
ACCCCAGCAGATTCGAAGAAGGTACAGTACACACACATGTATATATGTAT
GATGTATCCCTTCGATCGAAGGCATGCCTTGGTATAATCACTGAGTAGTC
ATTTTATTACTTTGTTTTGACAAGTCAGTAGTTCATCCATTTGTCCCATT
TTTTCAGCTTGGAAGTTTGGTTGCACTGGCACTTGGTCTAATAACTGAGT
AGTCATTTTATTACGTTGTTTCGACAAGTCAGTAGCTCATCCATCTGTCC
CATTTTTTCAGCTAGGAAGTTTGGTTGCACTGGCCTTGGACTAATAACTG
ATTAGTCATTTTATTACATTGTTTCGACAAGTCAGTAGCTCATCCATCTG
TCCCATTTTTCAGCTAGGAAGTTCGGATCTGGGGCCATTTGTTCCAGGCA
CGGGATAAGCATTCAGCC Construct pDAS5143 (e.g. pDAB3924) was built containing two gene expression cassettes. The first gene expression cassette (SEQ ID NO:8) contained the Sugar Cane Bacilliform Virus upstream-promoter (U.S. Pat. No. 6,489,462) followed by the *Zea mays* alcohol dehydrogenase (I) intron 6 (Dennis et al., (1984) *Nucleic Acids Res.* 12:3983-4000) and Maize Streak Virus 5'-UTR (Mullineaux et al., (1984) *EMBO J.* 3:3063-3068) operably linked to the tcdA transgene (U.S. Patent App. No. 2009/0221501) and flanked by the *Zea mays* Peroxidase 5 3'-UTR (International Patent App. No. 1998/056921). The second gene expression cassette contained a selectable marker gene and was made up of the *Oryza sativa* Actin promoter (U.S. Pat. No. 6,429,357) operably linked to a phosphinothricin acetyl transferase (Wohlleben et al., (1988) *Gene* 70: 25-37) transgene and terminated by the *Zea mays* Lipase 3'-UTR (U.S. Pat. No. 7,179,902). This construct was mobilized into the Superbinary pSB1 binary vector (Japan Tobacco, Tokyo, JP). The constructs used to complete pDAS5143 were molecularly confirmed via restriction enzyme digestion and DNA sequencing. The novel Sugar Cane Bacilliform Virus promoter followed by the *Zea mays* alcohol dehydrogenase (I) intron 6 and Maize Streak Virus 5'-UTR is disclosed herein as SEQ ID NO:9.

(SEQ ID NO: 8)
ATCGGAAGTTGAAGACAAAGAAGGTCTTAAATCCTGGCTAGCAACACTGA
ACTATGCCAGAAACCACATCAAAGATATCGGCAAGCTTCTTGGCCCATTA
TATCCAAAGACCTCAGAGAAAGGTGACGAAGGCTCAATTCAGAAGATTG
GAAGCTGATCAATAGGATCAAGACAATGGTGAGAACGCTTCCAAATCTCA
CTATTCCACCAGAAGATGCATACATTATCATTGAAACAGATGCATGTGCA
ACTGGATGGGGAGCAGTATGCAAGTGGAAGAAAAACAAGGCAGACCCAAG
AAATACAGAGCAAATCTGTAGGTATGCCAGTGGAAAATTTGATAAGCCAA
AAGGAACCTGTGATGCAGAAATCTATGGGGTTATGAATGGCTTAGAAAAG
ATGAGATTGTTCTACTTGGACAAAAGAGAGATCACAGTCAGAACTGACAG
TAGTGCAATCGAAAGGTTCTACAACAAGAGTGCTGAACACAAGCCTTCTG
AGATCAGATGGATCAGGTTCATGGACTACATCACTGGTGCAGGACCAGAG
ATAGTCATTGAACACATAAAAAGGGAAGAGCAATTGGTTTAGCTGACATCTT
GTCCAGGCTCAAAGCCAAATTAGCTCAGAATGAACCAACGGAAGAGATGA
TCCTGCTTACACAAGCCATAAGGGAAGTAATTCCTTATCCAGATCATCCA
TACACTGAGCAACTCAGAGAATGGGGAAACAAAATTCTGGATCCATTCCC
CACATTCAAGAAGGACATGTTCGAAAGAACAGAGCAAGCTTTTATGCTAA
CAGAGGAACCAGTTCTACTCTGTGCATGCAGGAAGCCTGCAATTCAGTTA
GTGTCCAGAACATCTGCCAACCCAGGAAGGAAATTCTTCAAGTGCGCAAT
GAACAAATGCCATTGCTGGTACTGGGCAGATCTCATTGAAGAACACATTC
AAGACAGAATTGATGAATTTCTCAAGAATCTTGAAGTTCTGAAGACCGGT
GGCGTGCAAACAATGGAGGAGGAACTTATGAAGGAAGTCACCAAGCTGAA
GATAGAAGAGCAGGAGTTCGAGGAATACCAGGCCACACCAAGGGCTATGT
CGCCAGTAGCCGCAGAAGATGTGCTAGATCTCCAAGACGTAAGCAATGAC
GATTGAGGAGGCATTGACGTCAGGGATGACCGCAGCGGAGATACTGGGC
CCATTCAGTGGATGCTCCACTGAGTTGTATTATTGTGTGCTTTTCGGACA
AGTGTGCTGTCCACTTTCTTTTGGCACCTGTGCCACTTTATTCCTTGTCT
GCCACGATGCCTTTGCTTAGCTTGTAAGCAAGGATCGCAGTGCGTGTGTG
ACACCACCCCCCTTCCGACGCTCTGCCTATATAAGGCACCGTCTGTAAGC
TCTTACGATCATCGGTAGTTCACCAAGGTACCCGGGGTCGACCTCGAGGG
GGGGCCCGGTACCCTGAAGGCTCGACAAGGCAGTCCACGGAGGAGCTGAT
ATTTGGTGGACAAGCTGTGGATAGGAGCAACCCTATCCCTAATATACCAG
CACCACCAAGTCAGGGCAATCCCCAGATCACCCCAGCAGATTCGAAGAAG
GTACAGTACACACACATGTATATATGTATGATGTATCCCTTCGATCGAAG
GCATGCCTTGGTATAATCACTGAGTAGTCATTTTATTACTTTGTTTTGAC
AAGTCAGTAGTTCATCCATTTGTCCCATTTTTTCAGCTTGGAAGTTTGGT
TGCACTGGCACTTGGTCTAATAACTGAGTAGTCATTTTATTACGTTGTTT
CGACAAGTCAGTAGCTCATCCATCTGTCCCATTTTTTCAGCTAGGAAGTT

-continued
TGGTTGCACTGGCCTTGGACTAATAACTGATTAGTCATTTTATTACATTG
TTTCGACAAGTCAGTAGCTCATCCATCTGTCCCATTTTTCAGCTAGGAAG
TTCGGATCTGGGGCCATTTGTTCCAGGCACGGGATAAGCATTCAGCCATG
GCTAATGAGTCAGTCAAGGAGATCCCGGATGTTCTCAAATCCCAGTGTGG
TTTCAACTGCCTCACGGACATCTCCCACAGCTCATTCAATGAGTTCCGCC
AGCAAGTCTCTGAGCACCTCTCATGGTCGGAGACGCATGACCTCTACCAC
GATGCTCAGCAAGCCCAGAAAGACAACCGGCTGTATGAGGCACGGATCCT
CAAGAGGGCCAACCCGCAGCTCCAGAATGCGGTCCACCTCGCCATCCTTG
CTCCAAATGCGGAATTGATTGGCTACAATAACCAATTCTCGGGAAGGGCC
TCACAGTATGTTGCGCCTGGCACAGTTTCGTCCATGTTCAGCCCAGCAGC
GTACCTCACAGAGCTGTACAGAGAGGCGAGGAACCTTCATGCGTCTGACT
CCGTGTACTATCTGGACACACGCAGACCGGACCTGAAGTCAATGGCCCTC
AGCCAGCAAAACATGGACATTGAACTGTCCACCCTTTCCTTGAGCAATGA
GCTTCTGTTGGAATCCATCAAGACTGAGAGCAAGCTGGAAAACTACACAA
AGGTGATGGAGATGCTGTCCACCTTCAGACCATCTGGAGCGACTCCATAC
CACGATGCCTATGAGAATGTGAGGGAGGTCATTCAGCTTCAAGACCCTGG
CCTTGAGCAGCTCAATGCCAGCCCAGCCATTGCGGGACTGATGCACCAAG
CCTCCCTGCTTGGGATCAATGCCTCCATCAGCCCTGAGCTGTTCAACATC
TTGACTGAAGAGATCACTGAGGGCAATGCGGAGGAACTGTACAAGAAAAA
CTTCGGCAACATTGAGCCTGCCAGCCTTGCAATGCCGGAATACCTGAAAC
GCTATTACAACTTGTCGGATGAGGAACTTTCGCAGTTCATTGGCAAAGCC
TCAAACTTTGGGCAGCAAGAGTACAGCAACAATCAGCTCATCACACCTGT
TGTGAACTCATCTGATGGCACTGTGAAGGTTTACCGCATCACAAGGGAGT
ACACCACAAATGCCTACCAGATGGATGTTGAACTGTTCCCGTTTGGAGGT
GAAAACTACCGGCTTGACTACAAGTTCAAGAACTTCTACAATGCATCCTA
CCTGTCGATCAAGCTGAACGACAAACGGGAGCTTGTGAGGACGGAAGGTG
CTCCCCAAGTGAACATTGAATACTCTGCCAACATCACACTCAACACAGCG
GACATCAGCCAGCCGTTTGAAATTGGCTTGACCAGAGTGCTTCCCTCGGG
CTCCTGGGCCTATGCGGCAGCCAAGTTTACGGTTGAGGAGTACAACCAGT
ACAGCTTCCTCCTGAAGCTCAACAAGGCAATCCGGCTGAGCAGAGCCACT
GAGCTGTCACCCACCATCCTGGAGGGCATTGTGAGGTCTGTCAACCTTCA
GCTTGACATCAACACTGATGTGCTTGGCAAGGTGTTCCTGACCAAGTATT
ACATGCAGCGCTATGCCATCCATGCGGAGACGGCACTGATCCTCTGCAAT
GCACCCATATCGCAGCGCTCGTATGACAACCAGCCCAGCCAGTTCAGCAG
ACTCTTCAACACTCCCCTTCTGAACGGCCAGTACTTCAGCACTGGAGATG
AAGAGATTGACCTGAACTCTGGCTCGACGGGTGACTGGAGGAAAACCATC
TTGAAGAGGGCCTTCAACATTGATGACGTTTCCCTCTTCCGCCTTTTGAA
GATCACAGATCACGACAACAAGGATGGCAAGATCAAGAACAATCTCAAGA
ACCTTTCCAACCTCTACATTGGCAAACTGCTTGCAGACATCCACCAGCTG
ACCATTGATGAGTTGGACCTGTTGCTGATTGCAGTTGGTGAGGGCAAGAC
CAACCTCTCTGCAATCTCAGACAAACAGTTGGCAACCCTCATCCGCAAGC
TGAACACGATCACAAGCTGGCTTCACACGCAGAAGTGGTCTGTTTTCCAA
CTGTTCATCATGACCAGCAGCGTCCTACAACAAGACCCTGACTCCGGAGAT
CAAGAACCTTTTGGATACAGTCTATCATGGTCTCCAAGGCTTTGACAAGG
ACAAGGCGGACCTGCTTCATGTCATGGCACCCTACATTGCAGCCACACTC
CAGCTCTCCTCTGAAAATGTTGCCCACTCAGTGCTGTTGTGGGCTGACAA
GCTCCAGCCTGGGGATGGAGCCATGACTGCTGAGAAGTTCTGGGACTGGC
TCAACACGAAGTACACACCTGGCTCCTCTGAGGCAGTTGAGACTCAAGAA
CACATTGTGCAGTACTGCCAAGCGCTTGCACAGTTGGAGATGGTTTACCA
CTCAACTGGCATCAACGAGAATGCCTTCCGCCTCTTTGTCACAAAGCCTG
AGATGTTTGGTGCTGCCACTGGAGCCGCTCCTGCCCATGATGCCCTGTCA
CTCATCATGTTGACGAGGTTTGCAGACTGGGTCAACGCCCTTGGTGAGAA
AGCCTCGTCTGTCCTGGCAGCCTTTGAAGCCAACTCCCTGACTGCGGAAC
AGCTTGCGGATGCCATGAACCTTGATGCCAACTTGCTCCTGCAAGCTTCG
ATCCAAGCCCAGAACCATCAGCATTTGCCACCTGTCACGCCTGAAAATGC
GTTCTCATGCTGGACCTCCATCAACACCATACTCCAGTGGGTGAACGTGG
CGCAACAGCTCAATGTGGCACCTCAAGGAGTGTCAGCGCTGGTTGGGCTT
GACTACATCCAGTCCATGAAGGAGACACCGACCTACGCAGTGGGAGAA
TGCAGCTGGCGTCTTGACAGCTGGTCTGAACTCACAGCAAGCCAACACGC
TGCATGCGTTCTTGGATGAGAGCCGCTCTGCTGCCCTCAGCACGTACTAT
ATCCGGCAAGTTGCCAAGGCAGCGGCTGCCATCAAGTCTCGGGATGACCT
CTACCAGTACTTGCTCATTGACAATCAGGTTTCTGCTGCCATCAAAACGA
CCCGGATTGCTGAGGCCATAGCCAGCATCCAGCTCTACGTCAACAGAGCG
CTTGAGAACGTTGAAGAGAATGCCAACTCTGGAGTGATTTCTCGCCAGTT
TTTCATAGACTGGGACAAGTACAACAAGCGCTACTCCACCTGGGCTGGGG
TCTCTCAGCTTGTCTACTATCCTGAGAACTACATAGATCCGACGATGCGG
ATTGGCCAGACCAAGATGATGGATGCCCTCCTTCAGTCGGTGTCCCAGAG
CCAGCTCAATGCTGACACTGTGGAGGATGCTTCATGAGCTACCTCACCT
CCTTCGAGCAAGTTGCCAACCTCAAGGTCATCTCTGCTTACCACGACAAC
ATCAACAATGACCAAGGGCTCACCTACTTCATTGGCCTGTCTGAAACTGA
TGCGGGTGAGTATTACTGGCGCTCAGTGGACCACAGCAAGTTCAACGATG
GCAAGTTTGCTGCAAATGCCTGGCTGTGAGTGGCACAAGATTGACTGCCC
ATCAACCCGTACAAGTCCACCATCAGACCTGTCATCTACAAGAGCCGCTT
GTACTTGCTCTGGCTTGAGCAGAAGGAAATCACGAAGCAGACTGGCAACT
CCAAAGATGGCTACCAGACTGAGACGGACTACCGCTATGAGTTGAAACTT
GCTCACATCCGCTATGATGGTACATGGAACACTCCGATAACGTTTGATGT
GAACAAGAGATTTCGGAGCTGAACCTGAAACTGGAGAAGAACAGAGCGCCTGGGC
TCTACTGTGCTGGCTACCAAGGGGAAGATACGCTGTTGGTGATGTTCTAC
AACCAGCAAGCACCCTTGACTCGTACAAGAACGCTTCCATGCAAGGCCT
CTACATCTTTGCTGACATGGCTTCCAAAGACATGACTCCGGAGCAGAGCA
ATGTCTACCGGGACAACTCCTACCAGCAATTTGACACCAACAATGTTCGG -continued

```
AGGGTCAATAACCGCTATGCGGAAGATTATGAGATCCCAAGCTCAGTGTC
TAGCCGCAAGGACTATGGCTGGGGAGACTACTATCTCAGCATGGTGTACA
ATGGTGACATACCCACGATCAACTACAAGGCTGCCTCCTCAGACCTGAAG
ATATACATCAGCCCCAAGCTCCGCATCATTCACAATGGCTATGAGGGCCA
GAAGAGGAACCAGTGCAACTTGATGAACAAGTATGGCAAACTTGGGGACA
AGTTCATTGTCTACACCTCGCTTGGTGTGAACCCGAACAATTCCTCGAAC
AAGCTCATGTTCTACCCGGTCTACCAGTACAGCGGCAACACCTCTGGCTT
GAACCAAGGGAGGCTCCTGTTCCACAGAGACACCACGTACCCGAGCAAGG
TGGAGGCGTGGATTCCTGGTGCCAAAAGGTCACTCACCAACCAGAATGCA
GCCATTGGTGATGACTATGCCACAGACAGCCTGAACAAGCCTGATGACCT
GAAGCAGTACATCTTCATGACTGACTCCAAGGGCACAGCCACTGATGTGT
CTGGTCCGGTGGAGATCAACACTGCAATCAGCCCAGCCAAGGTCCAAATC
ATTGTCAAAGCTGGTGGCAAGGAACAGACCTTCACAGCTGACAAAGATGT
GAGCATCCAGCCAAGCCCCTCCTTTGATGAGATGAACTACCAGTTCAACG
CTCTTGAAATTGATGGCTCGGGACTCAACTTCATCAACAATTCGGCTTCA
ATTGATGTGACGTTCACTGCCTTTGCGGAGGATGGGAGGAAATTGGGCTA
TGAGAGCTTCTCAATACCAGTCACCTTGAAGGTTTCCACTGACAATGCAC
TCACGCTTCATCACAACGAGAATGGAGCGCAGTACATGCAATGGCAGAGC
TACCGCACAAGGTTGAACACCCTCTTTGCAAGGCAACTTGTGGCCAGAGC
CACGACTGGCATTGACACCATACTCAGCATGGAAACGCAGAACATCCAAG
AGCCACAGTTGGGCAAGGGTTTCTATGCCACCTTTGTGATCCCACCCTAC
AACCTGTCAACGCATGGTGATGAGCGCTGGTTCAAGCTGTACATCAAGCA
CGTGGTTGACAACAATTCCCACATCATATACTCGGGTCAGCTCACTGACA
CGAACATCAACATCACCCTGTTCATCCCACTTGATGACGTTCCCCTGAAC
CAAGACTACCATGCCAAGGTCTACATGACCTTCAAGAAATCACCGTCAGA
TGGCACCTGGTGGGGACCGCACTTCGTTCGGGATGACAAAGGCATTGTCA
CAATCAACCCCAAGTCCATACTCACCCACTTTGAGTCTGTGAATGTTCTG
AATAACATCTCCTCAGAGCCGATGGACTTCTCGGGTGCCAACTCCCTGTA
CTTCTGGGAGTTGTTCTATTACACGCCGATGCTTGTGGCGCAGAGGTTGC
TCCATGAACAGAACTTTGATGAGGCCAACCGCTGGCTCAAGTATGTCTGG
AGCCCCTCGGGTTACATTGTGCATGGCCAGATCCAGAACTACCAATGGAA
TGTTCGCCCATTGCTTGAGGACACCTCCTGGAACTCTGACCCCCTTGACT
CGGTGGACCCTGATGCGGTGGCTCAGCATGACCCCATGCACTACAAGGTC
TCAACCTTCATGAGGACCCTGGACCTTCTGATTGCCAGAGGAGACCATGC
TTACCGCCAATTGGAACGGGACACACTGAATGAGGCAAAGATGTGGTACA
TGCAAGCTCTGCACCTCTTGGGAGACAAGCCGTACCTCCCGCTCAGCACC
ACATGGTCAGACCCAAGGTTGGACAGAGCAGCTGACATCACAACTCAGAA
TGCTCATGACTCTGCCATTGTGGCTCTGAGGCAGAACATCCCAACACCTG
CGCCACTGTCGCTGAGATCTGCGAACACCCTGACAGACCTGTTCCTCCCA
CAGATCAATGAGGTCATGATGAACTACTGGCAAACCTTGGCGCAGCGGGT
CTACAACCTCCGCCACAACCTCTCCATTGATGGGCAGCCGCTGTACCTCC
CAATCTATGCCACACCAGCTGACCCAAAGGCGCTTCTCAGCGCAGCTGTG
GCCACGAGCCAAGGGGGAGGCAAGCTCCCTGAAGAGCTTCATGTCGCTCTG
GAGGTTTCCCCACATGTTGGAGAATGCCAGAGGCATGGTGAGCCAACTGA
CTCAGTTTGGCTCGACGCTCCAGAACATCATTGAGAGGCAAGATGCAGAG
GCTCTGAATGCGTTGCTCCAGAATCAAGCAGCTGAGTTGATCCTGACGAA
CCTGTCAATCCAAGACAAGACCATTGAGGAACTTGATGCGGAAAAGACAG
TCCTTGAAAAGAGCAAGGCTGGAGCCCAAAGCCGGTTCGACTCATATGGC
AAGCTGTATGATGAGAACATCAATGCTGGGGAGAATCAAGCCATGACCCT
GAGGGCTTCAGCAGCGGGTCTGACCACGGCAGTGCAAGCGTCTCGCTTGG
CTGGGGCTGCGGCTGACCTCGTTCCCAACATCTTTGGGTTTGCTGGTGGC
GGATCAAGGTGGGGAGCCATTGCAGAAGCAACGGGCTATGTGATGGAGTT
CTCTGCCAATGTCATGAACACTGAGGCAGACAAAATCAGCCAATCGGAGA
CCTACAGACGGAGACGGCAAGAATGGGAGATACAAAGGAACAATGCAGAG
GCAGAACTGAAGCAAATAGATGCCCAACTGAAGTCCTTGGCTGTCAGAAG
GGAGGCTGCGGTCCTCCAAAAGACCTCCCTCAAGACCCAAGCAAGAGCAAA
CCCAGTCCCAGTTGGCGTTCCTCCAGAGGAAGTTCTCGAACCAAGCGCTG
TACAACTGGCTGAGGGGAAGGTTGGCAGCCATCTACTTCCAGTTCTATGA
CCTTGCTGTGGCCAGATGCCTCATGGCGGAACAAGCCTACCGCTGGGAAC
TGAATGATGACTCTGCCAGATTCATCAAACCGGGTGCATGGCAAGGCACA
TATGCTGGACTCCTTGCTGGGGAGACACTCATGCTCTCATTGCCCAGAT
GGAGGATGCTCACCTCAAACGGGACAAGAGGGCTCTGGAAGTGGAGCGGA
CAGTCAGCCTTGCGGAGGTCTATGCGGGACTGCCCAAAGACAATGGACCA
TTTTCGTTGGCGCAAGAGATAGACAAGTTGGTCAGCCAAGGGTCTGGATC
AGCGGGTTCTGGAAACAACAATCTGGCGTTCGGTGCTGGCACTGACACCA
AGACGTCCTCCAAGCCTCAGTCTCCTTTGCTGACCTGAAGATAAGGGAG
GACTACCCAGCGTCCCTTGGGAAGATCAGACGCATCAAGCAGATTTCAGT
GACCCTGCCAGCTCTTCTGGGTCCATACCAAGATGTTCAAGCGATCCTCT
CCTATGGGGACAAGGCTGGTTTGGCGAATGGCTGTGAGGCCCTTGCTGTG
TCACATGGCATGAATGACTCTGGGCAGTTCCAGCTTGATTTCAACGATGG
CAAGTTCCTGCCATTCGAGGGCATAGCCATTGATCAAGGCACCCTGACCC
TCTCCTTCCCCAATGCTTCGATGCCAGAGAAGGGAAAACAAGCCACCATG
CTCAAGACCCTGAATGATATCATACTCCACATCCGCTACACCATCAAGTG
AGTAGTTAGCTTAATCACCTAGAGCTCGTTTAAACTGAGGGCACTGAAGT
CGCTTGATGTGCTGAATTGTTTGTGATGTTGGTGGCGTATTTTGTTTAAA
TAAGTAAGCAAGCGTGTGATTTTATCATATGATCGATCTTTGGGGTTTTA
TTTAACACATTGTAAATGTGTATCTATTAATAACTCAATGTATAAGATG
TGTTCATTCTTCGGTTGCCATAGATCTGCTTATTTGACCTGTGATGTTT
GACTCCAAAAACCAAATCACAACTCAATAAACTCATGGAATATGTCCAC
CTGTTTCTTGAAGAGTTCATCTACCATTCCAGTTGGCATTTATCAGTGTT
GCAGCGGCGCTGTGCTTTGTAACATAACAATTGTTACGGCATATATCCAA
```

-continued
(SEQ ID NO: 9)
```
ATCGGAAGTTGAAGACAAAGAAGGTCTTAAATCCTGGCTAGCAACACTGA
ACTATGCCAGAAACCACATCAAAGATATCGGCAAGCTTCTTGGCCCATTA
TATCCAAAGACCTCAGAGAAAGGTGAGCGAAGGCTCAATTCAGAAGATTG
GAAGCTGATCAATAGGATCAAGACAATGGTGAGAACGCTTCCAAATCTCA
CTATTCCACCAGAAGATGCATACATTATCATTGAAACAGATGCATGTGCA
ACTGGATGGGGAGCAGTATGCAAGTGGAAGAAAAACAAGGCAGACCCAAG
AAATACAGAGCAAATCTGTAGGTATGCCAGTGGAAAATTTGATAAGCCAA
AAGGAACCTGTGATGCGAAAATCTATGGGGTTATGAATGGCTTAGAAAAG
ATGAGATTGTTCTACTTGGACAAAAGAGAGATCACAGTCAGAACTGACAG
TAGTGCAATCGAAAGGTTCTACAACAAGAGTGCTGAACACAAGCCTTCTG
AGATCAGATGGATCAGGTTCATGGACTACATCACTGGTGCAGGACCAGAG
ATAGTCATTGAACACATAAAAGGGAAGAGCAATGGTTTAGCTGACATCTT
GTCCAGGCTCAAAGCCAAATTAGCTCAGAATGAACCAACGGAAGAGATGA
TCCTGCTTACACAAGCCATAAGGGAAGTAATTCCTTATCCAGATCATCCA
TACACTGAGCAACTCAGAGAATGGGGAAACAAAATTCTGGATCCATTCCC
CACATTCAAGAAGGACATGTTCGAAAGAACAGAGCAAGCTTTTATGCTAA
CAGAGGAACCAGTTCTACTCTGTGCATGCAGGAAGCCTGCAATTCAGTTA
GTGTCCAGAACATCTGCCAACCCAGGAAGGAAATTCTTCAAGTGCGCAAT
GAACAAATGCCATTGCTGGTACTGGGCAGATCTCATTGAAGAACACATTC
AAGACAGAATTGATGAATTTCTCAAGAATCTTGAAGTTCTGAAGACCGGT
GGCGTGCAACAATGGAGGAGGAACTTATGAAGGAAGTCACCAAGCTGAA
GATAGAAGAGCAGGAGTTCGAGGAATACCAGGCCCACACCAAGGGCTATGT
CGCCAGTAGCCGCAGAAGATGTGCTAGATCTCCAAGACGTAAGCAATGAC
GATTGAGGAGGCATTGACGTCAGGGATGACCGCAGCGGAGAGTACTGGGC
CCATTCAGTGGATGCTCCACTGAGTTGTATTATTGTGTGCTTTTCGGACA
AGTGTGCTGTCCACTTTCTTTTGGCACCTGTGCCACTTTATTCCTTGTCT
GCCACGATGCCTTTGCTTAGCTTGTAAGCAAGGATCGCAGTGCGTGTGTG
ACACCACCCCCCTTCCGACGCTCTGCCTATATAAGGCACCGTCTGTAAGC
TCTTACGATCATCGGTAGTTCACCAAGGTACCCGGGGTCGACCTCGAGGG
GGGGCCCGGTACCCTGAAGGCTCGACAAGGCAGTCCACGGAGGAGCTGAT
ATTTGGTGGACAAGCTGTGGATAGGAGCAACCCTATCCCTAATATACCAG
CACCACCAAGTCAGGGCAATCCCCAGATCACCCCAGCAGATTCGAAGAAG
GTACAGTACACACACATGTATATATGTATGATGTATCCCTTCGATCGAAG
GCATGCCTTGGTATAATCACTGAGTAGTCATTTTACTTTGTTTTGAC
AAGTCAGTAGTTCATCCATTTGTCCCATTTTTTCAGCTTGGAAGTTTGGT
TGCACTGGCACTTGGTCTAATAACTGAGTAGTCATTTTATTACGTTGTTT
CGACAAGTCAGTAGCTCATCCATCTGTCCCATTTTTTCAGCTAGGAAGTT
TGGTTGCACTGGCCTTGGACTAATAACTGATTAGTCATTTTATTACATTG
TTTCGACAAGTCAGTAGCTCATCCATCTGTCCCATTTTTCAGCTAGGAAG
TTCGGATCTGGGGCCATTTGTTCCAGGCACGGGATAAGCATTCAGCC
```

Construct pDAB1405, a control construct, was built containing two gene expression cassettes, both of which were flanked by the RB7 Matrix Attachment Regions (MAR; International Patent App. No. WO9727207). The first gene expression cassette contained the *Zea mays* Ubiquitin 1 promoter operably linked to the green fluorescent protein transgene (U.S. Pat. No. 6,172,188) and flanked by the *Zea mays* Peroxidase 5 3'-UTR. The second gene expression cassette contained a selectable marker gene and was made up of the *Oryza sativa* Actin promoter (U.S. Pat. No. 6,429,357) operably linked to a phosphinothricin acetyl transferase (Wohlleben et al., (1988) Gene 70: 25-37) transgene and terminated by the *Zea mays* Lipase 3'-UTR (U.S. Pat. No. 7,179,902). This construct was mobilized into the Superbinary pSB1 binary vector (Japan Tobacco, Tokyo, JP). The constructs used to complete pDAB1405 were molecularly confirmed via restriction enzyme digestion and DNA sequencing.

TABLE 1

Constructs are designated by pDAS number with a brief description of regulatory elements and selectable marker used in each construct.

| Construct Name | Promoter | Intron | Leader | Gene of Interst | 3'-UTR | Selectable Marker |
|---|---|---|---|---|---|---|
| pDAS5128 | ZmUbi1 | ADH1 intron 6 | MSV | tcdA | Per 5 | PAT |
| pDAS5143 | SCBV | ADH1 intron 6 | MSV | tcdA | Per 5 | PAT |
| pDAS5144 | ZmPer 5 | ADH1 intron 6 | MSV | tcdA | Per 5 | PAT |
| pDAB1405 | ZmUbi1 | — | — | gfp | Per5 | PAT |

Example 3: Plant Transformation and Molecular Confirmation

Plant Material.

Zea mays c.v. Hi-II was used for all transformation experiments. Plants were grown in the greenhouse and ears were harvested at about 9-11 days after pollination, when immature zygotic embryos were between 1-2 mm in length. Ears were dehusked, rinsed, and stored at 4° C. for up to 1 day prior to use.

Agrobacterium Culture Initiation.

Agrobacterium tumefaciens strain LBA4404 harboring the constructs described above were maintained as glycerol stocks at −80° C. Prior to the initiation of the transformation experiments, bacteria were streaked from the glycerol stocks onto YEP plates containing 250 mg/L streptomycin, 100 mg/L spectinomycin and 10 mg/L tetracycline. The plates were incubated at 28° C. for 24 hours then transferred to 19° C. for 2 days until a lawn of cells developed on each plate.

Cocultivation of Immature Embryos.

One to two loops of Agrobacterium were taken from each YEP plate and suspended in 45 ml of N6-inf medium (N6 salts and vitamins, 1.5 mg/L 2,4-D, 700 mg/L L-Proline, 6.84% sucrose, 3.6% glucose, pH adjusted to 5.2) supplemented with 100 µM acetosyringone, and vortexed until a uniform suspension was obtained. Bacteria were transferred to Nephelo™ flasks and the culture density was adjusted to approximately 200 Klett units using the blue filter. Flasks were shaken at 75 rpm on a rotary shaker for 2-4 hours at room temperature while immature embryos were isolated. Maize ears were sterilized by rinsing in 70% ethanol for 5 minutes followed by 20-30 minute immersion in a 20% bleach solution containing several drops of Liquinox®. The ears were triple rinsed in sterile deionized water and wrapped in sterile paper towels and foil until use. The cocultivation and selection protocol closely followed that outlined by Frame et al. (*Plant Physiol.* 129: 12-22, 2005). Immature zygotic embryos were excised from maize kernels and placed in Eppendorf tubes containing 2 ml of N6-inf medium with 100 µM acetosyringone. Embryos from multiple ears were either pooled in tubes or kept separate. Embryos were washed in infection medium 1-2 times and the solution was replaced with approximately 1 ml of bacterial suspension. The tube was gently inverted a few times and incubated at room temperature for 5 minutes. Embryos were transferred to N6-AS (KW) medium (N6 Salts and vitamins, 1.5 mg/L 2,4-D, 700 mg/L L-proline, 0.85 mg/L silver nitrate, 300 mg/L L-cysteine, 3% sucrose, 3 g/L Gelrite™, 100 µM acetosyringone and pH adjusted to 5.8) in 100×15 mm plates. After excess liquid was removed from the plate, embryos were oriented with the scutellar side up using a microscope.

Plates were sealed with 3M® tape or Parafilm®, and incubated for 3 to 4 days at 20° C. in the dark. For TcdA constructs 50-120 embryos were treated per construct, and approximately 30-50 embryos were treated for the positive control construct (pDAB1405). To monitor transformation efficiency putative positive control isolates were evaluated for GFP expression after 2 weeks. The remaining *Agrobacterium* suspension was spun down at 5000 rpm in a tabletop centrifuge, and the pellet was resuspended in 100 µl of liquid, and then streaked on a YEP +strep/spec/tet plate, and allowed to incubate for 3 days at 28° C., then used for revalidation. As a positive control to assess tissue culture response of the maize donor material, approximately 5 embryos per ear were plated on 15Ag medium (N6 salts and vitamins, 100 mg/L Enzymatic casein hydrolysate, 1 mg/L 2,4D, 2% sucrose, 2.5 g/L Gelrite™, pH 5.8, supplemented with 10 mg/L silver nitrate and 25 mM L-proline) and incubated at 28° C. in the dark for 2 weeks. Control embryos were scored for embryogenic response at 2 and 4 weeks and then discarded.

Isolation, Selection, and Regeneration.

After 3-4 days of cocultivation, surviving embryos were transferred to KW-Resting medium (N6 salts and vitamins, 1.5 mg/L 2,4-D, 700 mg/L L-proline, 500 mg/L MES, 0.85 mg/L silver nitrate, 100 mg/L vancomycin, 100 mg/L cefotaxime, 3% sucrose, 8 g/L TC agar and pH adjusted to 5.8). Ten embryos were placed on each 60×20 mm plate and sealed with 3M® tape or Parafilm®. Plates were incubated in a dark culture room at 28° C. for 7 days. Because all constructs contained the PAT gene as the selectable marker, the bialaphos-based formulation Herbiace® was used as the selective agent. Embryos were transferred to N6 (1.5H) KW medium (N6 salts and vitamins, 1.5 mg/L 2,4-D, 700 mg/L L-proline, 500 mg/L MES, 0.85 mg/L silver nitrate, 100 mg/L vancomycin, 100 mg/liter cefotaxime, 1.5 mg/L Herbiace®, 3% sucrose, 8 g/L TC agar and pH adjusted to 5.8). After approximately two weeks embryos were transferred to medium with a doubled level of Herbiace®, and subsequent transfers were to N6 (3.0H) KW medium (N6 salts and vitamins, 1.5 mg/L 2,4-D, 700 mg/L L-proline, 500 mg/L MES, 0.85 mg/L silver nitrate, 100 mg/L vancomycin, 100 mg/L cefotaxime, 3.0 mg/L Herbiace®, 3% sucrose, 8 g/L TC agar and pH adjusted to 5.8. After the first transfer to N6 (3.0H) KW medium, any fast growing embryogenic tissue was subcultured to a separate plate of N6 (3.0H) KW medium to bulk up putative transgenic isolates. When sufficient quantities of embryogenic callus material were obtained, samples were taken for zygosity and expression assays. Events meeting copy number and expression criteria were transferred to 28(1H) regeneration medium (MS salts and vitamins, 5 mg/L BAP, 25 µg/L 2,4-D, 3% sucrose, 1 mg/L Herbiace®, 2.5 g/L Gelrite™ and pH adjusted to 5.7) and cultured for seven days in low light (13 µEm-$_{2S-1}$) with 16:8 hour photoperiod, followed by seven days in high light (40 µEm-$_{2S-1}$). Emerging shoots were transferred to 36(1H) medium (MS salts and vitamins, 3% sucrose, 1 mg/L Herbiace®, 2.5 g/L Gelrite™, pH 5.7) in 100×25 mm plates. When shoots reached about 3-5 mm in length they were transferred to SHGA rooting medium (SH salts and vitamins, 1 g/L myo-inositol, 1% sucrose, 2.5 g/L Gelrite™, pH 5.8) in 25×150 mm glass tubes. Plantlets were transferred to the greenhouse after adequate root development was observed.

Transfer and Establishment of T0 Plants in the Greenhouse.

Transgenic plants were assigned unique identifiers and transferred to the greenhouse. Plants were transplanted from tubes to small pots (3.5" SVD) and covered with a Humidome™ for one week to help acclimate the plants to the greenhouse environment (~28° C. day temp/~26° C. night temp/16:8 supplemental lighting). Plants were then transplanted from small pots to root trainers for insect-bioassay (Spencer-Lemaire Industries, Edmonton, Alberta Canada; style Tinus 350-4). Three plants per event were placed in root trainers while the remaining three plants per event were transferred to 5-gallon pots by the greenhouse staff for hand pollinations and T1 seed production. Approximately four days after transplanting to root trainers, plants were infested for bioassay.

Production of T1 Seed.

Plants that passed the bioassay and the corresponding three plants per event that were not bioassayed were transplanted to 5 gallon pots. Observations were taken on a weekly basis to track any abnormal phenotypes. As ears emerged, shoot bags were placed over the shoot prior to silk emergence to ensure no cross-contamination by stray pollen. If any shoots produced silk before covering, notes were made and the shoot was removed. The second shoot was covered to use for pollinations. Plants that produced abnormal or no shoots were recorded in the database. Tassels from the T0 plants were removed prior to shedding to eliminate transgenic pollen flow in the greenhouse. Silks were cut back to provide an even brush to accept pollen during pollinations. Pollen from the inbred *Zea mays* c.v. 5XH751 was used for all pollinations.

After the pollinations had been completed, the plants were placed in the greenhouse and allowed to grow and develop. Ears were peeled back at 21 days after pollination to enhance dry down followed by complete harvest (ear removed from plant) at 42 days after pollination. Ears were placed in a drier for 1 week followed by seed processing (shelling, counting, packaging in pre-printed envelopes, and seed count entry into database).

Example 4: Protein Expression of Transgenic Plants/Events

Protein Expression by Western Blot in Callus Plant Material.

Maize callus samples were analyzed for the presence of TcdA by western blots. In preparation for analysis, 200 mg of callus sample was collected into 96 well cluster tube boxes (Corning, Corning, N.Y.) and stored at −80° C. At the time of analysis, the samples were extracted by adding 4 steel beads (3.5 mm, Bio Spec Products, Bartlesville, Okla.) plus 200 µl of extraction buffer (1× Phosphate Buffered Saline (PBS) +0.1% Triton-X-100). Samples were beat using beads in the Kleco bead Mill™ (Garcia Machine, Visalia, Calif.) for 3 minutes at the maximum setting. After processing, the samples were centrifuged at 3000 rcf for 5 minutes in a plate centrifuge (Qiagen). The resulting supernatant was transferred by pipetting to new tubes. Western samples were prepared by mixing extract with an appropriate amount of sample buffer (NuPage LDS™ 4×Sample buffer (Invitrogen, Carlsbad, Calif.) with 40 mM dithiothreitol). A purified protein positive control (PA1, 0.4 mg/ml) was prepared in sample buffer as above to a concentration of 6.25 ng/µl. Forty microliters of each prepared sample and standard were placed in PCR tubes (Thermo Scientific) and heated in a thermocycler (Applied BioSystems, Foster City, Calif.) for 5 minutes at 90° C. Samples were resolved on 3-8% Tris-Acetate gels (Invitrogen EA0375) with Tris-Acetate-SDS running buffer (Invitrogen).

In addition, the inner gel chamber had antioxidant (Invitrogen) added to the running buffer. Samples were loaded according to gel specifications with 25 µL of sample loaded for callus samples, 4 µl loaded for the purified protein control (25 ng) and 15 µl of a molecular weight marker (SeeBlue Marker™, Invitrogen, Carlsbad, Calif.). Gels were run at a constant 150 V for 75 minutes. Meanwhile, transfer pads and 0.2 µm nitrocellulose membranes (Invitrogen) were prepared by soaking in transfer buffer (1×NuPage Transfer Buffer™ (Invitrogen)+10-20% methanol).

After resolving the proteins on the gel, the blot module (Invitrogen) and gels to be transferred were assembled according to the manufacturer's instructions. Gels were then transferred at a constant 45 V for at least 1.5 hours (2 hours for 2 gels per blot module). Early callus Western blots were run using the Bio-Rad Criterion™ system (4-20% Tris-HCl gels [Bio-Rad, Hercules, Calif.] and 1× Tris/Glycine/SDS running buffer). However, due to poor gel to gel quality the decision was made to switch to the above specified Invitrogen system. Post transfer, the membranes were blocked for 30 minutes at room temperature in Western Breeze Blocking buffer (Invitrogen). The blocking solution was removed and the primary antibodies (MAB anti-TcdA 148G4.1 and MAB anti-TcdA 148D11.1) were added at a concentration of 1.0 µg/ml in blocking buffer. The membranes were incubated for at least 1 hour at room temperature. The membranes were washed 3 times for 5 minutes each with Western Breeze™ wash solution (Invitrogen). The secondary antibody (Anti-Mouse HRP [Sigma, St. Louis, Mo.]) was prepared in blocking solution at a 1:3000 dilution. The membranes were incubated for 1 hour at room temperature before washing as above. Excess wash buffer was removed from the membranes by gently blotting the edge of the membrane to paper towels. The membranes were exposed to chemiluminescent substrate (Thermo Scientific) for 5 minutes. Excess substrate was removed as above and the membranes were wrapped in plastic wrap. In a darkroom, X-ray film (Thermo Scientific, Waltham, Mass.) was exposed to the membranes to visualize bands. Films were developed for 5 minute and 2 hour film exposures.

Protein Expression by ELISA in T0 Plant Material.

Maize leaf material was analyzed for the presence of TcdA using a mono-mono ELISA. Leaves from greenhouse grown plants were sampled by cutting a 2 cm leaf piece from the tip of the first fully expanded leaf, one week after plants were infested with rootworm eggs. Samples were collected into 96 well cluster tube boxes (Corning) and frozen at −80° C. Samples were prepared for extraction by adding 3 steel beads (3.5 mm, Bio Spec Products, Bartlesville, Okla.), 1 steel bead (4.5 mm Daisy) and 100 μl of PBEX extraction buffer (19 mM $NaH_2PO_4$, 31 mM $Na_2HPO_4$, 10 mM 0.5M EDTA, and 0.1% Triton®-X 100). The samples were pulverized using the Kleco Beadmill™ (Garcia Machine) for 3 minutes at the maximum setting. An additional 300 μl of PBEX extraction buffer was added to the samples and the samples were processed for an additional 1 minute. After processing, the samples were centrifuged at 3000 rcf for 5 minutes in a plate centrifuge (Qiagen). The resulting supernatant was transferred to new tubes. ELISA plates were prepared by Beacon Analytical Systems (Portland, Me.) as follows: Maxisorb Plates™ (Thermo Fisher Scientific) were coated with an anti-TcdA monoclonal antibody (MAB anti-TcdA 148G4.1) at a concentration of 1.0 μg/ml in 1×PBS. Following overnight incubation at 4° C., plates were blocked with 1% cold water fish gelatin (Sigma) in PBST (PBS+ 0.5% Tween®-20). Plates were dried and individually wrapped for storage. At the time of analysis, plates are warmed to room temperature and washed 4 times in a plate washer (TomTec) using 350 μl of PBST per wash prior to loading samples. A purified protein reference antigen (PA1, 0.4 mg/ml) was diluted in PBEX buffer to 150 ng/ml and used to generate a standard curve of serial dilutions from 150 ng/ml to 2.34 ng/ml. Samples were diluted in PBEX buffer to a starting dilution of 1:8 and serial diluted 3 additional times. Next, 100 μl of all standards and sample dilutions were loaded in duplicate onto the ELISA plate. Samples were incubated on the ELISA plates at room temperature for 1 hour. Following incubation, the plates were washed as above. A horseradish peroxidase conjugated monoclonal antibody (MAB anti-TcdA 148D11.1—HRP) (prepared by Covance, Denver, Pa.) was diluted to 1 μg/ml in PBS and added to plates at 100 μl per well. The plates were incubated at room temperature for 1 hour. After incubation the plates were washed. The stack of plates was rotated 180° and the wash step was repeated. Next, 1-Step Ultra TMB Substrate™ (Thermo Scientific) was added to the plates at 100 µl per well. As the wells with the lowest dilution of the standard curve began to show blue color, the reaction was stopped by adding 50 µl of stop solution (0.4 N $H_2SO_4$). The plates were read in a plate reader (Molecular Devices) using SoftMax® Pro v5 (Molecular Devices) at a wavelength of 450 nm minus a 650 nm reference. The TcdA concentration of test samples was calculated by linear regression of a quadratic standard curve.

Total soluble protein in leaf extracts was determined by Bradford assay. Maize leaf samples were diluted using Milli-Q® water in a 96 well polypropylene plate (Corning). A protein standard (Pre-diluted Protein Assay Standards: BSA [Thermo Scientific]) was diluted to a starting concentration of 0.5 mg/ml and serial diluted down the plate to 0.0625 mg/ml leaving the bottom wells as a water blank. Samples were transferred to a Maxisorb® plate (Thermo Fisher Scientific) and prepared protein dye (BioRad) was added to the wells. The plates were read in a plate reader (Molecular Devices) using SoftMax® Pro v5 (Molecular Devices) at a wavelength of 595 nm. The total soluble protein concentration was calculated by linear regression of a quadratic standard curve. Statistical analysis was conducted using JMP software (version 7.0.2, SAS Industries, Inc., Cary, N.C.). Protein expression (parts per million of TcdA) values were transformed using a log+1 transformation.

The ELISA herein used two monoclonal antibodies that could only recognize one epitope per antibody thus reducing the ability of the assay to recognize truncated TcdA. Because of this specificity, there is confidence that the expression levels determined by the ELISA represent full length TcdA. Since the lowest dilution of the leaf sample extract is 1:8, this results in a lower limit of detection of 16 ng/ml and a lower limit of quantitation (lowest dilution factor x lowest standard that has an O.D. of 2 times the background) of 36 ng/ml. Thus any results between 36 ng/ml and zero should not be considered accurate.

Protein Expression by ELISA in T1 Plant Material.

As a non-destructive screening method, maize plants were analyzed for the presence of the selectable marker Phosphinothrincin Acetyltransferase (PAT) by a qualitative enzyme linked immunosorbent assay (ELISA). Leaves from greenhouse grown plants were sampled by cutting a 2 cm leaf piece from the tip of the first fully expanded leaf. Samples were collected into 96 well cluster tube boxes (Corning) and frozen at −80° C. Samples were prepared for extraction by adding two steel beads (4.5 mm, Daisy, Rogers Ark.) and 100 μl of phosphate buffered saline with 0.5% Tween®-20 (PBST) extraction buffer. The samples were pulverized using the Kleco Beadmill™ (Garcia Machine) for three minutes at the maximum setting. An additional 300 μl of PBST extraction buffer was added to the samples and the samples were processed for an additional one minute. After bead beating, the samples were centrifuged at 3,000 rcf for five minutes in a plate centrifuge (Qiagen). The resulting supernatant was transferred to new tubes. ELISA plates from PAT kit AP014 (EnviroLogix, Portland, Me.) were warmed to room temperature in preparation for use. A purified protein reference antigen (PAT Standard, TSN 104799, 63 μg/ml) was diluted in PBST buffer to 10 ng/ml and used to generate a standard curve of the following dilutions: 5 ng/ml, 0.625 ng/ml, and 0.156 ng/ml. To prepare the plates for use, 50 μl of enzyme conjugate (EnviroLogix, Portland, Me.) was added to each well followed by 50 μl of PBST. Next, 50 μl of the standards and samples were loaded onto the ELISA plate in their respective wells and allowed to incubate at room temperature for one hour. Following incubation, the plates were washed four times in a plate washer (TomTec) using 350 μl of PBST per wash. EnviroLogix TMB Substrate™ was added to the plates at 100 μl per well and allowed to incubate for 15 minutes. The reaction was stopped by adding 100 μl of stop solution. The plates were read in a plate reader (Molecular Devices) using SoftMax® Pro v5 (Molecular Devices) at a wavelength of O.D. 450, the subtracted OD was greater than 0.7 nm.

Plants selected for insect bioassay were analyzed for the presence of TcdA by a Mono/Mono ELISA. Leaf samples were collected at two time points: one week post infestation with rootworm eggs and at the end of bioassay (21 days post infestation). Leaves were sampled by cutting a 2 cm leaf piece from the tip of the first fully expanded leaf. Samples were collected into 96 well cluster tube boxes (Corning) and frozen at −80° C. Samples were prepared for extraction by adding two steel beads (4.5 mm, Daisy) and 100 μl of PBEX extraction buffer (19 mM $NaH_2PO_4$, 31 mM $Na_2HPO_4$, 10 mM 0.5M EDTA, and 0.1% Triton®-X 100). The samples were pulverized using the Kleco Beadmill™ (Garcia Machine) for three minutes at the maximum setting. An additional 300 μl of PBEX extraction buffer was added to the samples and the samples were processed for an additional 1 minute. After bead beating, the samples were centrifuged at 3000 rcf for five minutes in a plate centrifuge (Qiagen). Root samples for each plant were collected at the end of bioassay. Root samples (200 mg per plant) were prepared for extraction by adding four steel beads (4.5 mm, Daisy) and 400 μl of PBEX extraction buffer to a 2 ml tube. The samples were pulverized using the Kleco Beadmill™ (Garcia Machine) for 3 minutes at the maximum setting. After bead beating, the samples were centrifuged at 3000 rcf for five minutes in a plate centrifuge (Qiagen). The resulting supernatant was transferred to new tubes. ELISA plates were prepared by Beacon Analytical Systems (Portland, Me.) as follows: MaxiSorb plates (Thermo Fisher Scientific) were coated with an anti-TcdA monoclonal antibody (MAB anti-TcdA 148G4.1) at a concentration of 1.0 μg/ml in 1×PBS. Following overnight incubation at 4° C., plates were blocked with 1% cold water fish gelatin (Sigma) in PBST (PBS+0.5% Tween®-20). Plates were dried and individually wrapped for storage. At the time of analysis, plates were warmed to room temperature and washed four times in a plate washer (TomTec) using 350 μl of PBST per wash prior to loading samples.

A purified protein reference antigen (PA1, 0.4 mg/ml) was diluted in PBEX buffer to 150 ng/ml and used to generate a standard curve of serial dilutions from 150 ng/ml to 2.344 ng/ml. Samples were diluted in PBEX buffer to a starting dilution of 1:8 and serial diluted 3 additional times (1:8, 1:16, 1:32, 1:64). Next, 100 μl of the standards and sample dilutions were loaded in duplicate onto the ELISA plate. Samples were incubated on the ELISA plates at room temperature for one hour. Following incubation, the plates were washed as above. A horseradish peroxidase conjugated monoclonal antibody (MAB anti-TcdA 148D11-HRP) was diluted to 1 μg/ml in PBS and added to plates at 100 μl per well. The plates were incubated at room temperature for 1 hour. After incubation the plates were washed with Step Ultra TMB™ substrate (Thermo Scientific). This wash solution was added to the plates at 100 μl per well. As the wells with the lowest dilution of the standard curve began to show blue color, the reaction was stopped by adding 50 μl of stop solution (0.4 N $H_2SO_4$). The plates were read in a plate reader (Molecular Devices) using SoftMax® Pro v5 (Molecular Devices) at a wavelength of O.D. 450 nm, with a subtraction of a 650 nm reference. The TcdA concentration of test samples was calculated by quadratic regression analysis.

After the bioassay, a subset of leaf and root samples were analyzed for the presence of TcdA by Western blots. Western samples were prepared by mixing extract with an appropriate amount of sample buffer (NuPage LDS™ 4× Sample buffer [Invitrogen] with 40 mM Dithiothreitol). A purified protein positive control (PA1, 0.4 mg/ml) was prepared in sample buffer as above to a concentration of 6.25 ng/μl. Next, 40 μl of each prepared sample and standard were placed in PCR tubes (Thermo Scientific) and heated in a thermocycler (Applied BioSystems) for 5 minutes at 90° C. Samples were resolved on 3-8% Tris-Acetate gels (Invitrogen) with Tris-Acetate-SDS running buffer (Invitrogen). In addition, the inner gel chamber had antioxidant (Invitrogen) added to the running buffer. Samples were loaded according to gel specifications with 25 μl of sample loaded for each of the leaf and root samples, 4 μl loaded for the purified protein control (25 ng) and 15 μl of a molecular weight marker (SeeBlue Marker™, Invitrogen). Gels were run at a constant 150 V for 75 minutes. While the gels ran, transfer pads and 0.2 μm nitrocellulose membranes (Invitrogen) were prepared by soaking in transfer buffer (1× NuPage® Transfer Buffer (Invitrogen)+10-20% methanol). After resolving the proteins on the gel, the blot module (Invitrogen) and gels to be transferred were assembled according to the manufacturer's instructions. Gels were then transferred at a constant 45 V for at least 1.5 hours (2 hours for 2 gels per blot module). Post transfer, the membranes were blocked for 30 minutes at room temperature in Western Breeze® blocking buffer (Invitrogen). The blocking solution was removed and the primary antibodies (MAB anti-TcdA 148G4.1 and MAB anti-TcdA 148D11.1) were added at a concentration of 1.0 μg/ml in blocking buffer. The membranes were incubated for at least 1 hour at room temperature. The membranes were washed 3 times for 5 minutes each with Western Breeze® wash solution (Invitrogen). The secondary antibody (Anti-Mouse HRP (Sigma)) was prepared in blocking solution at a 1:3000 dilution. The membranes were incubated for 1 hour at room temperature before washing as above. Excess wash buffer was removed from the membranes by gently blotting the edge of the membrane to paper towels. The membranes were exposed to chemiluminescent substrate (Thermo Scientific) for 5 minutes. Excess substrate was removed as above and the membranes were wrapped in plastic wrap. In a darkroom, X-ray film (Thermo Scientific) was exposed to the membranes to visualize bands. Films were developed for 5 minute and 2 hour film exposures.

Total soluble protein in leaf and root extracts was determined by Bradford assay. Maize leaf and root samples were diluted using Milli-Q® water in a 96 well polypropylene plate (Corning). A protein standard (Pre-diluted Protein Assay Standards: BSA™ (Thermo Scientific)) was diluted to a starting concentration of 0.5 mg/ml and serial diluted down the plate to 0.0625 mg/ml leaving the bottom wells as a water blank. Samples were transferred to a MaxiSorb Plate™ (Thermo Fisher Scientific) and prepared protein dye (BioRad) was added to the wells. The plates were read in a plate reader (Molecular Devices) using SoftMax® Pro v5 (Molecular Devices) at a wavelength of O.D. 595 nm. The total soluble protein concentration was calculated by quadratic regression analysis.

Statistical analysis was conducted using JMP® software (version 7.0.2, SAS Industries, Inc., Cary, N.C.). Protein expression (parts per million of TcdA) values were transformed using a log transformation.

Example 5: $T_0$ Transgenic Plant Expression Screening

Protein Expression Analysis in T0 Plants.

The Western blot and ELISA data showed that the transgenic pDAS5144 events specifically expressed the TcdA protein in root tissues. The expression of TcdA in both callus and T0 leaf samples for the pDAS5144 events was surprisingly low as shown in TABLE 2. The maize leaf expression profile of TcdA for the various constructs is reported in parts per million (PPM). The expression of TcdA in the pDAS5144 construct was significantly less than the other constructs. The average expression of TcdA in the pDAS5144 constructs was 14 PPM. The range of expression for leaf material from this construct was 0-200 PPM. The lower expression level in leaf tissue is a result of the promoter tissue specificity.

TABLE 2

Expression of TcdA protein in T0 maize leaves and callus by construct.

| | Construct | Number of Events | Number Positive | % Positive | Leaf PPM Range | Average PPM | Average PPM Top Quartile | Tukey-Kramer means comparison* | Log + 1 Mn PPM |
|---|---|---|---|---|---|---|---|---|---|
| Leaf Expression | pDAS5128 | 114 | — | — | 0-650 | 81 | 250 | A | 1.00 |
| | pDAS5143 | 127 | — | — | 0-850 | 64 | 220 | A | 0.85 |
| | pDAS5144 | 123 | — | — | 0-200 | 14 | 60 | B | 0.41 |
| Callus Expression | pDAS5128 | 165 | 86 | 52% | — | — | — | — | — |
| | pDAS5143 | 97 | 33 | 34% | — | — | — | — | — |
| | pDAS5144 | 105 | 11 | 10% | — | — | — | — | — |

*Levels not connected by the same letter are significantly different.

Protein Expression Analysis in T1 Plants.

TABLE 3 lists the results of quantitative ELISA analysis for the TcdA protein isolated from T1 maize leaves one week post infestation during an insect bioassay. The T1 maize leaves for the various events were harvested and submitted for insect bioassay to test the efficacy of the expressed TcdA protein. The average TcdA expression (PPM) was recorded by construct, with range and top quartile results. In addition, the Tukey-Kramer means separation analysis results for average TcdA expression in maize leaves is reported for each set of events. The TcdA protein expression of plants containing construct pDAS5144 was negligible in the leaf tissues. Despite negligible expression of TcdA in maize leaves, bioassay results indicated that the pDAS5144 events provided tolerance to insect infestation (e.g., rootworm infestation). Analyzing the combination of the bioassay data and protein expression data (from the leaves) showed no correlation between protein expression in leaves and root damage levels by the rootworms. The lower TcdA expression level in leaf tissue combined with the expression of TcdA in roots suggests that the novel chimeric gene promoter regulatory element express the tcda transgene in a root-tissue specific manner.

TABLE 3

Average TcdA protein expression levels (ppm) in maize leaves, by construct, for samples collected during insect bioassay.

| Construct | Number of Events | Leaf PPM Range | Average PPM | Average PPM Top Quartile | Tukey-Kramer means comparison* | Log + 1 Mn PPM |
|---|---|---|---|---|---|---|
| pDAS5128 | 241 | 0-686 | 55 | 209 | B | 0.64 |
| pDAS5143 | 73 | 0-789 | 141 | 452 | A | 1.06 |
| pDAS5144 | 99 | 0-102 | 2 | 8 | C | 0.04 |

*Levels not connected by the same letter are significantly different.

Protein Expression Analysis after Insect Bioassay.

ELISA and Western blots were used to analyze a subset of leaf and root material after completion of insect bioassay experiments. TABLES 4 and 5 list the average TcdA protein expression in leaf and root material, respectively. While there were significant differences in expression levels of TcdA protein in T1 maize leaves between constructs, the differences between constructs were less distinguished in roots analyzed following the insect bioassay as compared to leaves. The pDAS5144 events produced the greatest range of TcdA protein expression, resulting in expression of TcdA protein in the transgenic events that were assayed. Comparatively, from the total protein recovered, noTcdA protein was detectable in the leaf tissues. These results further suggest that the transgene expression from construct pDAS5144, in which TcdA is driven by the novel chimeric gene promoter regulatory elements, is root specific.

TABLE 4

Expression of TcdA protein (PPM) in maize leaves, by construct, after the completion of the insect bioassay.

| Construct | Number of Events Leaf | Leaf Range PPM | Leaf Average PPM | Leaf Average PPM Top Quartile | Tukey-Kramer Means Comparison* | Log + 1 Mn PPM |
|---|---|---|---|---|---|---|
| pDAS5128 | 33 | 0-468 | 79 | 147 | B | 1.26 |
| pDAS5143 | 18 | 0-872 | 389 | 590 | A | 2.25 |
| pDAS5144 | 56 | 0 | 0 | 0 | C | 0.00 |

*Levels not connected by the same letter are significantly different.

TABLE 5

Expression of TcdA protein (PPM) in maize roots, by construct, after the completion of the insect bioassay.

| Construct | Number of Events Root | Root Range PPM | Root Average PPM | Root Average PPM Top Quartile | Tukey-Kramer Means Comparison* | Log + 1 Mn PPM |
|---|---|---|---|---|---|---|
| pDAS5128 | 33 | 0-1401 | 389 | 840 | AB | 2.10 |
| pDAS5143 | 18 | 0-1200 | 449 | 885 | AB | 2.21 |
| pDAS5144 | 56 | 0-1393 | 252 | 606 | B | 1.56 |

*Levels not connected by the same letter are significantly different.

Protein Expression at V6 and VT Stages of Development.

Further studies were performed to assess the expression levels of TcdA by the novel chimeric gene promoter regulatory elements at the V6 and VT stages of corn plant development. Maize plants were grown expressing the transgene TcdA from each of the constructs 5116, 5117, and 5144. Protein was isolated for the T1 leaf tissue and quantitated, these results were compared to total protein isolated from the whole plant. These results as shown in TABLE 6 further confirm that the tcda transgene expression from the novel chimeric gene promoter regulatory elements of construct pDAS5144 is root specific. The TcdA protein was detected from total protein isolated from whole plants, but there was no TcdA protein detected in the leaves. Additionally, the novel chimeric gene promoter regulatory elements of construct pDAS5144 expressed the tcda transgene at both the V6 and VT stages of maize growth and development.

TABLE 6

Total TcdA protein from T1 maize leaves harvested at the V6 and VT stages of plant growth and development.

| Construct | Leaf N | Mean Leaf Expression at V6 in PPM | Mean Leaf Expression at VT in PPM | Root N | Mean Root Expression at V6 in PPM | Mean Root Expression at VT in PPM |
|---|---|---|---|---|---|---|
| pDAS5128 | 96 | 90 | 114 | 68 | 149 | 179 |
| pDAS5143 | 84 | 439 | 67 | 57 | 106 | 101 |
| pDAS5144 | 49 | 0.0 | 0.0 | 34 | 28.0 | 12.0 |

As such a novel chimeric gene promoter regulatory elements were operably linked and used to express a transgene as a gene expression cassette, and the resulting expression profile was characterized. Disclosed for the first time is a chimeric promoter comprising an upstream-promoter polynucleotide sequence that was obtained from Zea mays Peroxidase 5 followed by the Zea mays alcohol dehydrogenase (I) intron 6 and Maize Streak Virus 5'-UTR for use in gene expression constructs. Constructs expressing the novel chimeric gene promoter regulatory elements were shown to express a transgene in a root tissue specific manner. The tissue specificity results are surprising, given that a chimeric promoter comprising an upstream-promoter polynucleotide sequence that was obtained from Zea mays Peroxidase 5 followed by the Zea mays alcohol dehydrogenase intron 1, expressed a transgene in both leaf and root tissues. see Table 22 of U.S. Pat. No. 6,384,207.

What is claimed is:

1. A chimeric polynucleotide sequence comprising SEQ ID NO:1, and wherein the chimeric polynucleotide sequence promotes root-specific expression of a transgene.

2. The chimeric polynucleotide sequence of claim 1, wherein the polynucleotide consists of SEQ ID NO:1.

3. The chimeric polynucleotide sequence of claim 1, wherein the chimeric polynucleotide sequence is operably linked to a transgene.

4. The chimeric polynucleotide sequence of claim 3, wherein the transgene is tcdA.

5. The chimeric polynucleotide sequence of claim 1, wherein the operably linked transgene encodes a polypeptide or small RNA.

6. A transgenic cell comprising a synthetic polynucleotide comprising SEQ ID NO:1, wherein the synthetic polynucleotide is a root-specific promoter.

7. The transgenic cell of claim 6, wherein the synthetic polynucleotide consists of SEQ ID NO:1.

8. The transgenic cell of claim 6, wherein the transgenic cell is produced by a plant transformation method.

9. The transgenic cell of claim 8, wherein the plant transformation method is selected from the group consisting of an *Agrobacterium*-mediated transformation method, a biolistics transformation method, a silicon carbide transformation method, a protoplast transformation method, and a liposome transformation method.

10. A transgenic plant comprising the transgenic cell of claim 6.

11. The transgenic plant of claim 10, wherein the transgenic plant is a monocotyledonous or a dicotyledonous plant.

12. The transgenic plant of claim 11, wherein the monocotyledonous plant is selected from the group consisting of a maize plant, a rice plant, and a wheat plant.

13. A transgenic seed from the transgenic plant of claim 10, wherein the seed comprises said chimeric polynucleotide.

\* \* \* \* \*

SEQUENCE LISTING

```
<160> NUMBER OF SEQ ID NOS: 9

<210> SEQ ID NO 1
<211> LENGTH: 2179
<212> TYPE: DNA
<213> ORGANISM: Artificial Sequence
<220> FEATURE:
<223> OTHER INFORMATION: The chimeric promoter sequences are made up of
      an upstream-promoter polynucleotide sequence that was obtained
      from Zea mays Peroxidase 5 followed by the Zea mays alcohol
      dehydrogenase (I) intron 6 and Maize Streak Virus 5' -UTR

<400> SEQUENCE: 1
accactgttg taacttgtaa gccactagct cacgttctcc atgagctctt ctctctgctg      60
tttcttcctc tgctaactgc gttatgatat gacgtcgtat aaataatctc acaatacttc     120
cttattttca gcatggcctc tttatgttt atttaacagt agcaaccaac gccgctcgat      180
gtttccttca agaaacggcc actcactatg tggtgtgcag aagaacaaat gtaagcagct    240
cctacaggta ccagtagtca tgtcagtgtg gaagctttcc aaccaacgcc tccttcgagg    300
aacctggtcg tgctgacatg aatgtaggcc atgcaagcac aagcacctaa cgcgaatcat    360
cacgacgcgc cgtgtactgg gcgttggtac atcacacccc gcgtttgacc tgatcggaag    420
catgcgtgtg tgttggctgc aggaccggct ataggtttcc tgcattggac agcagaagcc    480
agtcatgtta ggcactcacg cgctcctgcc gtttgatgaa tcatccggtc tttcgtattg    540
atcactagtt cactacgctg atatagcaaa ttttaagatg tgaaaccacg agacgagcga    600
taaatcttag acgttaccta tccatatgaa gcttgtgcga aaaaaaggcg tgccgctgta    660
gcatcattcg tatacacttt tgtccccaaa gacagggata cgaatccatg ctcgacagaa    720
ccctcccttc cctgcagata acgacactta agtataacaa aagtagttgg attatttcag    780
aagcaaaatc tcacttttcg ctggcctttt tgtactttgg ttacttgagt tcagacagtg    840
tatgctatat tgtcatgtgc tgcgtaaggt ttaaatatgg ttcgacaaat atatcagtat    900
atcactactt tgttatgggt ggggcctagc acaaacttga tacagctagg ataaagttag    960
aacgatgact gatctactgt aaagcgacac ctgtcctgtt atggtagttt aagtccattc    1020
ctggacgact ccagatccag gatatgatgc tgttacataa tgcgattgtt cacaataaaa    1080
ttgcatgatg ttcttctact ctttaggcag ttttgttcaa caggcaagtt gcataatgca    1140
tgtgcatata tgagcagcat aatcatcaat taatcatagg ttcgtcattt tagtttcact    1200
ccttcacatt attccagccc ttgaagaaaa atgtagcagt gcttgctgtt taataagtgg    1260
cagagctgtt ttcactccac ctacgcttgt ctaggaccaa aattttaatc tgtcactttg    1320
agctaaaact gaagcaccaa accgctacaa aagaacgtag gagctgaatt gtaacttgat    1380
gggattacta tagcagttgc tacagttcta gctagctacc ttattctata cgcatcaccc    1440
taacaacccg gctgactgct gcatctgacc ccaccgtccc ctgctccaaa ccaactctcc    1500
tttccttgca tgcactacac ccacttcctg cagctatata taccaccata tgcccatctt    1560
```

| | |
|---|---|
| atgaaaccat ccacaagagg agaagaaaca atcaaccagc aacactcttc tcttataaca | 1620 |
| tagtacagcg aaggtaactc acggtaccct gaaggctcga caaggcagtc cacggaggag | 1680 |
| ctgatatttg gtggacaagc tgtggatagg agcaaccta tccctaatat accagcacca | 1740 |
| ccaagtcagg gcaatcccca gatcaccca gcagattcga agaaggtaca gtacacacac | 1800 |
| atgtatatat gtatgatgta tcccttcgat cgaaggcatg ccttggtata atcactgagt | 1860 |
| agtcatttta ttactttgtt ttgacaagtc agtagttcat ccatttgtcc cattttttca | 1920 |
| gcttggaagt ttggttgcac tggccttggt ctaataactg agtagtcatt ttattacgtt | 1980 |
| gtttcgacaa gtcagtagct catccatctg tcccattttt tcagctagga agtttggttg | 2040 |
| cactggcctt ggactaataa ctgattagtc attttattac attgtttcga caagtcagta | 2100 |
| gctcatccat ctgtcccatt tttcagctag gaagttcgga tctggggcca tttgttccag | 2160 |
| gcacgggata agcattcag | 2179 |

<210> SEQ ID NO 2
<211> LENGTH: 1642
<212> TYPE: DNA
<213> ORGANISM: Zea mays

<400> SEQUENCE: 2

| | |
|---|---|
| accactgttg taacttgtaa gccactagct cacgttctcc atgagctctt ctctctgctg | 60 |
| tttcttcctc tgctaactgc gttatgatat gacgtcgtat aaataatctc acaatacttc | 120 |
| cttattttca gcatggcctc ttttatgttt atttaacagt agcaaccaac gccgctcgat | 180 |
| gtttccttca agaaacggcc actcactatg tggtgtgcag aagaacaaat gtaagcagct | 240 |
| cctacaggta ccagtagtca tgtcagtgtg gaagctttcc aaccaacgcc tccttcgagg | 300 |
| aacctggtcg tgctgacatg aatgtaggcc atgcaagcac aagcacctaa cgcgaatcat | 360 |
| cacgacgcgc cgtgtactgg gcgttggtac atcacacccc gcgtttgacc tgatcggaag | 420 |
| catgcgtgtg tgttggctgc aggaccggct ataggtttcc tgcattggac agcagaagcc | 480 |
| agtcatgtta ggcactcacg cgctcctgcc gtttgatgaa tcatccggtc tttcgtattg | 540 |
| atcactagtt cactacgctg atatagcaaa ttttaagatg tgaaaccacg agacgagcga | 600 |
| taaatcttag acgttaccta tccatatgaa gcttgtgcga aaaaaaggcg tgccgctgta | 660 |
| gcatcattcg tatacacttt tgtccccaaa gacagggata cgaatccatg ctcgacagaa | 720 |
| ccctcccttc cctgcagata cgacactta agtataacaa aagtagttgg attattttcag | 780 |
| aagcaaaatc tcacttttcg ctggcctttt tgtactttgg ttacttgagt tcagacagtg | 840 |
| tatgctatat tgtcatgtgc tgcgtaaggt ttaaatatgg ttcgacaaat atatcagtat | 900 |
| atcactactt tgttatgggt ggggcctagc acaaacttga tacagctagg ataaagttag | 960 |
| aacgatgact gatctactgt aaagcgacac ctgtcctgtt atggtagttt aagtccattc | 1020 |
| ctggacgact ccagatccag gatatgatgc tgttacataa tgcgattgtt cacaataaaa | 1080 |
| ttgcatgatg ttcttctact cttaggcag ttttgttcaa caggcaagtt gcataatgca | 1140 |
| tgtgcatata tgagcagcat aatcatcaat taatcatagg ttcgtcattt tagtttcact | 1200 |
| ccttcacatt attccagccc ttgaagaaaa atgtagcagt gcttgctgtt taataagtgg | 1260 |
| cagagctgtt ttcactccac ctacgcttgt ctaggaccaa aatttaatc tgtcactttg | 1320 |
| agctaaaaact gaagcaccaa accgctacaa aagaacgtag gagctgaatt gtaacttgat | 1380 |
| gggattacta tagcagttgc tacagttcta gctagctacc ttattctata cgcatcaccc | 1440 |
| taacaacccg gctgactgct gcatctgacc ccaccgtccc ctgctccaaa ccaactctcc | 1500 |

```
tttccttgca tgcactacac ccacttcctg cagctatata taccaccata tgcccatctt    1560
atgaaaccat ccacaagagg agaagaaaca atcaaccagc aacactcttc tcttataaca    1620
tagtacagcg aaggtaactc ac                                             1642

<210> SEQ ID NO 3
<211> LENGTH: 117
<212> TYPE: DNA
<213> ORGANISM: maize streak virus

<400> SEQUENCE: 3
ctgaaggctc gacaaggcag tccacggagg agctgatatt tggtggacaa gctgtggata      60
ggagcaaccc tatccctaat ataccagcac caccaagtca gggcaatccc cagatca        117

<210> SEQ ID NO 4
<211> LENGTH: 341
<212> TYPE: DNA
<213> ORGANISM: zea mays

<400> SEQUENCE: 4
gtacagtaca cacacatgta tatatgtatg atgtatccct tcgatcgaag gcatgccttg      60
gtataatcac tgagtagtca ttttattact ttgttttgac aagtcagtag ttcatccatt     120
tgtcccattt tttcagcttg gaagtttggt tgcactggcc ttggtctaat aactgagtag     180
tcattttatt acgttgtttc gacaagtcag tagctcatcc atctgtccca tttttttcagc    240 taggaagttt ggttgcactg gccttggact aataactgat tagtcatttt attacattgt     300
ttcgacaagt cagtagctca tccatctgtc ccatttttca g                         341

<210> SEQ ID NO 5
<211> LENGTH: 10431
<212> TYPE: DNA
<213> ORGANISM: artificial sequence
<220> FEATURE:
<223> OTHER INFORMATION: pDAB3620 first gene expression cassette

<400> SEQUENCE: 5
tacaaaaaag caggctccgc aagcttgcat gcctgcagat ccccggggat ctccgcgggg      60
gcccaccact gttgtaactt gtaagccact agctcacgtt ctccatgagc tcttctctct     120
gctgtttctt cctctgctaa ctgcgttatg atatgacgtc gtataaataa tctcacaata     180
cttccttatt ttcagcatgg cctcttttat gtttatttaa cagtagcaac caacgccgct     240 cgatgttttcc ttcaagaaac ggccactcac tatgtggtgt gcagaagaac aaatgtaagc     300
agctcctaca ggtaccagta gtcatgtcag tgtggaagct ttccaaccaa cgcctccttc     360
gaggaacctg tcgtgctga catgaatgta ggccatgcaa gcacaagcac ctaacgcgaa     420
tcatcacgac gcgccgtgta ctgggcgttg gtacatcaca ccccgcgttt gacctgatcg     480
gaagcatgcg tgtgtgttgg ctgcaggacc ggctataggt ttcctgcatt ggacagcaga     540
agccagtcat gttaggcact cacgcgctcc tgccgtttga tgaatcatcc ggtctttcgt     600
attgatcact agttcactac gctgatatag caaattttaa gatgtgaaac cacgagacga     660
gcgataaatc ttagacgtta cctatccata tgaagcttgt gcgaaaaaaa ggcgtgccgc     720
tgtagcatca ttcgtataca cttttgtccc caaagacagg gatacgaatc catgctcgac     780
agaaccctcc cttccctgca gataacgaca cttaagtata acaaaagtag ttggattatt     840
tcagaagcaa aatctcactt ttcgctggcc ttttttgtact ttggttactt gagttcgagc     900
agtgtatgct atattgtcat gtgctgcgta aggtttaaat atggttcgac aaatatatca     960
```

-continued

```
gtatatcact actttgttat gggtggggcc tagcacaaac ttgatacagc taggataaag      1020
ttagaacgat gactgatcta ctgtaaagcg acacctgtcc tgttatggta gtttaagtcc      1080
attcctggac gactccagat ccaggatatg atgctgttac ataatgcgat tgttcacaat      1140
aaaattgcat gatgttcttc tactctttag gcagttttgt tcaacaggca agttgcataa      1200
tgcatgtgca tatatgagca gcataatcat caattaatca taggttcgtc attttagttt      1260
cactccttca cattattcca gcccttgaag aaaaatgtag cagtgcttgc tgtttaataa      1320
gtggcagagc tgttttcact ccacctacgc ttgtctagga ccaaaatttt aatctgtcac      1380
tttgagctaa aactgaagca ccaaaccgct acaaaagaac gtaggagctg aattgtaact      1440
tgatgggatt actatagcag ttgctacagt tctagctagc taccttattc tatacgcatc      1500
accctaacaa cccggctgac tgctgcatct gaccccaccg tccctgctc caaaccaact      1560
ctcctttcct tgcatgcact acacccactt cctgcagcta tatataccac catatgccca      1620
tcttatgaaa ccatccacaa gaggagaaga aacaatcaac cagcaacact cttctcttat      1680
aacatagtac agcgaaggta actcacggta ccctgaaggc tcgacaaggc agtccacgga      1740
ggagctgata tttggtggac aagctgtgga taggagcaac cctatcccta atataccagc      1800
accaccaagt cagggcaatc cccagatcac cccagcagat tcgaagaagg tacagtacac      1860
acacatgtat atatgtatga tgtatcccct cgatcgaagg catgccttgg tataatcact      1920
gagtagtcat tttattactt tgttttgaca agtcagtagt tcatccatttt gtcccatttt      1980
ttcagcttgg aagtttggtt gcactggcac ttggtctaat aactgagtag tcattttatt      2040
acgttgtttc gacaagtcag tagctcatcc atctgtccca ttttttcagc taggaagttt      2100
ggttgcactg gccttggact aataactgat tagtcatttt attacattgt ttcgacaagt      2160
cagtagctca tccatctgtc ccattttttca gctaggaagt tcggatctgg ggccatttgt      2220
tccaggcacg ggataagcat tcagccatgg ctaatgagtc agtcaaggag atcccggatg      2280
ttctcaaatc ccagtgtggt ttcaactgcc tcacggacat ctcccacagc tcattcaatg      2340
agttccgcca gcaagtctct gagcacctct catggtcgga gacgcatgac ctctaccacg      2400
atgctcagca agcccagaaa gacaaccggc tgtatgaggc acggatcctc aagagggcca      2460
acccgcagct ccagaatgcg gtccacctcg ccatccttgc tccaaatgcg gaattgattg      2520
gctacaataa ccaattctcg ggaagggcct cacagtatgt tgcgcctggc acagtttcgt      2580
ccatgttcag cccagcagcg tacctcacag agctgtacag agaggcgagg aaccttcatg      2640
cgtctgactc cgtgtactat ctggacacac gcagaccgga cctgaagtca atggccctca      2700
gccagcaaaa catggacatt gaactgtcca ccctttcctt gagcaatgag cttctgttgg      2760
aatccatcaa gactgagagc aagctggaaa actacacaaa ggtgatggag atgctgtcca      2820
ccttcagacc atctggagcg actccatacc acgatgccta tgagaatgtg agggaggtca      2880
ttcagcttca agaccctggc cttgagcagc tcaatgccag cccagccatt gcggactga      2940
tgcaccaagc ctccctgctt gggatcaatg cctccatcag ccctgagctg ttcaacatct      3000
tgactgaaga gatcactgag ggcaatgcgg aggaactgta caagaaaaac ttcggcaaca      3060
ttgagcctgc cagccttgca atgccggaat acctgaaacg ctattacaac ttgtcggatg      3120
aggaactttc gcagttcatt ggcaaagcct caaactttgg gcagcaagag tacagcaaca      3180
atcagctcat cacacctgtt gtgaactcat ctgatggcac tgtgaaggtt taccgcatca      3240
caagggagta caccacaaat gcctaccaga tggatgttga actgttcccg tttggaggtg      3300
aaaactaccg gcttgactac aagttcaaga acttctacaa tgcatcctac ctgtcgatca      3360
```

```
agctgaacga caaacgggag cttgtgagga cggaaggtgc tccccaagtg aacattgaat    3420
actctgccaa catcacactc aacacagcgg acatcagcca gccgtttgaa attggcttga    3480
ccagagtgct tccctcgggc tcctgggcct atgcggcagc caagtttacg gttgaggagt    3540
acaaccagta cagcttcctc ctgaagctca acaaggcaat ccggctgagc agagccactg    3600
agctgtcacc caccatcctg gagggcattg tgaggtctgt caaccttcag cttgacatca    3660
acactgatgt gcttggcaag gtgttcctga ccaagtatta catgcagcgc tatgccatcc    3720
atgcggagac ggcactgatc ctctgcaatg cacccatatc gcagcgctcg tatgacaacc    3780
agcccagcca gttcgacaga ctcttcaaca ctccccttct gaacggccag tacttcagca    3840
ctggagatga agagattgac ctgaactctg gctcgacggg tgactggagg aaaaccatct    3900
tgaagagggc cttcaacatt gatgacgttt ccctcttccg ccttttgaag atcacagatc    3960
acgacaacaa ggatggcaag atcaagaaca atctcaagaa cctttccaac ctctacattg    4020
gcaaactgct tgcagacatc caccagctga ccattgatga gttggacctg ttgctgattg    4080
cagttggtga gggcaagacc aacctctctg caatctcaga caaacagttg gcaaccctca    4140
tccgcaagct gaacacgatc acaagctggc ttcacacgca gaagtggtct gttttccaac    4200
tgttcatcat gaccagcacg tcctacaaca agaccctgac tccggagatc aagaaccttt    4260
tggatacagt ctatcatggt ctccaaggct tgacaagga caaggcggac ctgcttcatg    4320
tcatggcacc ctacattgca gccacactcc agctctcctc tgaaaatgtt gcccactcag    4380
tgctgttgtg ggctgacaag ctccagcctg gggatggagc catgactgct gagaagttct    4440
gggactggct caacacgaag tacacacctg gctcctctga ggcagttgag actcaagaac    4500
acattgtgca gtactgccaa gcgcttgcac agttggagat ggtttaccac tcaactggca    4560
tcaacgagaa tgccttccgc ctctttgtca caaagcctga gatgtttggt gctgccactg    4620
gagccgctcc tgcccatgat gccctgtcac tcatcatgtt gacgaggttt gcagactggg    4680
tcaacgccct tggtgagaaa gcctcgtctg tcctggcagc cttttgaagcc aactccctga    4740
ctgcggaaca gcttgcggat gccatgaacc ttgatgccaa cttgctcctg caagcttcga    4800
tccaagccca gaaccatcag catttgccac ctgtcacgcc tgaaaatgcg ttctcatgct    4860
ggacctccat caacaccata ctccagtggg tgaacgtggc gcaacagctc aatgtggcac    4920
ctcaaggagt gtcagcgctg gttgggcttg actacatcca gtccatgaag gagacaccga    4980
cctacgcgca gtgggagaat gcagctggcg tcttgacagc tggtctgaac tcacagcaag    5040
ccaacacgct gcatgcgttc ttggatgaga gccgctctgc tgccctcagc acgtactata    5100
tccggcaagt tgccaaggca gcggctgcca tcaagtctcg ggatgacctc taccagtact    5160
tgctcattga caatcaggtt tctgctgcca tcaaaacgac ccggattgct gaggccatag    5220
ccagcatcca gctctacgtc aacagagcgc ttgagaacgt tgaagagaat gccaactctg    5280
gagtgatttc tcgccagttt ttcatagact gggacaagta caacaagcgc tactccacct    5340
gggctggggt ctctcagctt gtctactatc ctgagaacta catagatccg acgatgcgga    5400
ttggccagac caagatgatg gatgccctcc ttcagtcggt gtcccagagc cagctcaatg    5460
ctgacactgt ggaggatgcc ttcatgagct acctcacctc cttcgagcaa gttgccaacc    5520
tcaaggtcat ctctgcttac cacgacaaca tcaacaatga ccaagggctc acctacttca    5580
ttggcctgtc tgaaactgat gcgggtgagt attactggcg ctcagtggac acagcaagt    5640
tcaacgatgg caagtttgct gcaaatgcct ggtctgagtg gcacaagatt gactgcccca    5700
tcaacccgta caagtccacc atcagacctg tcatcctaca agagccgctt gtacttgctct    5760
```

-continued

```
ggcttgagca gaaggaaatc acgaagcaga ctggcaactc caaagatggc taccagactg   5820
agacggacta ccgctatgag ttgaaacttg ctcacatccg ctatgatggt acatggaaca   5880
ctccgataac gtttgatgtg aacaagaaga tttcggagct gaaactggag aagaacagag   5940
cgcctgggct ctactgtgct ggctaccaag gggaagatac gctgttggtg atgttctaca   6000
accagcaaga caccettgac tcgtacaaga acgcttccat gcaaggcctc tacatctttg   6060
ctgacatggc ttccaaagac atgactccgg agcagagcaa tgtctaccgg gacaactcct   6120
accagcaatt tgacaccaac aatgttcgga gggtcaataa ccgctatgcg aagattatg    6180
agatcccaag ctcagtgtct agccgcaagg actatggctg gggagactac tatctcagca   6240
tggtgtacaa tggtgacata cccacgatca actacaaggc tgcctcctca gacctgaaga   6300
tatacatcag ccccaagctc cgcatcattc acaatggcta tgaggccag aagaggaacc    6360
agtgcaactt gatgaacaag tatggcaaac ttggggacaa gttcattgtc tacacctcgc   6420
ttggtgtgaa cccgaacaat tcctcgaaca agctcatgtt ctaccggtc taccagtaca    6480
gcggcaacac ctctggcttg aaccaaggga ggctcctgtt ccacagagac accacgtacc   6540
cgagcaaggt ggaggcgtgg attcctggtg ccaaaaggtc actcaccaac cagaatgcag   6600
ccattggtga tgactatgcc acagacagcc tgaacaagcc tgatgacctg aagcagtaca   6660
tcttcatgac tgactccaag ggcacagcca ctgatgtgtc tggtccggtg gagatcaaca   6720
ctgcaatcag cccagccaag gtccaaatca ttgtcaaagc tggtggcaag aacagacct    6780
tcacagctga caagatgtg agcatccagc caagcccctc ctttgatgag atgaactacc    6840
agttcaacgc tcttgaaatt gatggctcgg gactcaactt catcaacaat tcggcttcaa   6900
ttgatgtgac gttcactgcc tttgcggagg atgggaggaa attgggctat gagagcttct   6960
caataccagt caccttgaag gtttccactg acaatgcact cacgcttcat cacaacgaga   7020
atggagcgca gtacatgcaa tggcagagct accgcacaag gttgaacacc ctctttgcaa   7080
ggcaacttgt ggccagagcc acgactggca ttgacaccat actcagcatg gaaacgcaga   7140
acatccaaga gccacagttg ggcaagggtt tctatgccac cttttgtgatc ccaccctaca   7200
acctgtcaac gcatggtgat gagcgctggt tcaagctgta catcaagcac gtggttgaca   7260
acaattccca tcatcatatac tcgggtcagc tcactgacac gaacatcaac atcaccctgt   7320
tcatcccact tgatgacgtt ccctgaacc aagactacca tgccaaggtc tacatgacct    7380
tcaagaaatc accgtcagat ggcacctggt ggggaccgca cttcgttcgg gatgacaaag   7440
gcattgtcac aatcaacccc aagtccatac tcacccactt tgagtctgtg aatgttctga   7500
ataacatctc ctcagagccg atggacttct cgggtgccaa ctccctgtac ttctgggagt   7560
tgttctatta cacgccgatg cttgtggcgc agaggttgct ccatgaacag aactttgatg   7620
aggccaaccg ctggctcaag tatgtctgga gcccctcggg ttacattgtg catggccaga   7680
tccagaacta ccaatggaat gttcgcccat tgcttgagga cacctcctgg aactctgacc   7740
cccttgactc ggtggaccct gatgcggtgg ctcagcatga cccatgcac tacaaggtct    7800
caaccttcat gaggaccctg gaccttctga ttgccagagg agaccatgct taccgccaat   7860
tggaacggga cacactgaat gaggcaaaga tgtggtacat gcaagctctg cacctcttgg   7920
gagacaagcc gtacctcccg ctcagcacca catggtcaga cccaaggttg acagagcag    7980
ctgacatcac aactcagaat gctcatgact ctgccattgt ggctctgagg cagaacatcc   8040
caacacctgc gccactgtcg ctgagatctg cgaacaccct gacagacctg ttcctccccc   8100
agatcaatga ggtcatgatg aactactggc aaaccttggc gcagcgggtc tacaacctcc   8160
```

-continued

```
gccacaacct ctccattgat gggcagccgc tgtacctccc aatctatgcc acaccagctg      8220
acccaaaggc gcttctcagc gcagctgtgg ccacgagcca agggggaggc aagctccctg      8280
agagcttcat gtcgctctgg aggtttcccc acatgttgga gaatgccaga ggcatggtga      8340
gccaactgac tcagtttggc tcgacgctcc agaacatcat tgagaggcaa gatgcagagg      8400
ctctgaatgc gttgctccag aatcaagcag ctgagttgat cctgacgaac ctgtcaatcc      8460
aagacaagac cattgaggaa cttgatgcgg aaaagacagt ccttgaaaag agcaaggctg      8520
gagcccaaag ccggttcgac tcatatggca agctgtatga tgagaacatc aatgctgggg      8580
agaatcaagc catgaccctg agggcttcag cagcgggtct gaccacggca gtgcaagcgt      8640
ctcgcttggc tggggctgcg gctgacctcg ttcccaacat cttTgggttt gctggtggcg      8700
gatcaaggtg gggagccatt gcagaagcaa cgggctatgt gatggagttc tctgccaatg      8760
tcatgaacac tgaggcagac aaaatcagcc aatcggagac ctacagacgg agacggcaag      8820
aatgggagat acaaggaac aatgcagagg cagaactgaa gcaaatagat gcccaactga      8880
agtccttggc tgtcagaagg gaggctgcgg tcctccaaaa gacctccctc aagacccagc      8940
aagagcaaac ccagtcccag ttggcgttcc tccagaggaa gttctcgaac caagcgctgt      9000
acaactggct gaggggaagg ttggcagcca tctacttcca gttctatgac cttgctgtgg      9060
ccagatgcct catggcggaa caagcctacc gctgggaact gaatgatgac tctgccagat      9120
tcatcaaacc gggtgcatgg caaggcacat atgctggact ccttgctggg gagacactca      9180
tgctctcatt ggcccagatg gaggatgctc acctcaaacg ggacaagagg gctctggaag      9240
tggagcggac agtcagcctt gcggaggtct atgcgggact gcccaaagac aatggaccat      9300
tttcgttggc gcaagagata gacaagttgg tcagccaagg gtctggatca gcgggttctg      9360
gaaacaacaa tctggcgttc ggtgctggca ctgacaccaa gacgtccctc caagcctcag      9420
tctcctttgc tgacctgaag ataagggagg actacccagc gtcccttggg aagatcagac      9480
gcatcaagca gatttcagtg accctgccag ctcttctggg tccataccaa gatgttcaag      9540
cgatcctctc ctatggggac aaggctggtt tggcgaatgg ctgtgaggcc cttgctgtgt      9600
cacatggcat gaatgactct gggcagttcc agcttgattt caacgatggc aagttcctgc      9660
cattcgaggg catagccatt gatcaaggca ccctgaccct ctccttcccc aatgcttcga      9720
tgccagagaa gggaaaacaa gccaccatgc tcaagaccct gaatgatatc atactccaca      9780
tccgctacac catcaagtga gtagttagct taatcaccta gagctcgttt aaactgaggg      9840
cactgaagtc gcttgatgtg ctgaattgtt tgtgatgttg gtggcgtatt ttgtttaaat      9900
aagtaagcat ggctgtgatt ttatcatatg atcgatcttt ggggttttat ttaacacatt      9960
gtaaaatgtg tatctattaa taactcaatg tataagatgt gttcattctt cggttgccat     10020
agatctgctt atttgacctg tgatgttttg actccaaaaa ccaaaatcac aactcaataa     10080
actcatggaa tatgtccacc tgtttcttga agagttcatc taccattcca gttggcattt     10140
atcagtgttg cagcggcgct gtgctttgta acataacaat tgttacggca tatatccaac     10200
ggccggccta ggccacggtg gccagatcca ctagaggcgc gcctctagtt ctagagcggc     10260
cgcttaattc actggccgtc gttttacaac gtcgtgactg ggaaaaccct ggcgttaccc     10320
aacttaatcg ccttgcagca catccccctt tcgccagctg gcgtaatagc gaagaggccc     10380
gcaccgatcg cccttcccaa cagttgcaaa tggcgcgccg acccagcttt c              10431
```

<210> SEQ ID NO 6
<211> LENGTH: 9471
<212> TYPE: DNA
<213> ORGANISM: artificial sequence
<220> FEATURE:
<223> OTHER INFORMATION: pDAB3619 first gene expression cassette

<400> SEQUENCE: 6

| | | | | | |
|---|---|---|---|---|---|
| gtgcagcgtg | acccggtcgt | gcccctctct | agagataatg | agcattgcat gtctaagtta | 60 |
| taaaaaatta | ccacatattt | tttttgtcac | acttgtttga | agtgcagttt atctatcttt | 120 |
| atacatatat | ttaaacttta | ctctacgaat | aatataatct | atagtactac aataatatca | 180 |
| gtgttttaga | gaatcatata | aatgaacagt | tagacatggt | ctaaaggaca attgagtatt | 240 |
| ttgacaacag | gactctacag | ttttatcttt | ttagtgtgca | tgtgttctcc ttttttttg | 300 |
| caaatagctt | cacctatata | atacttcatc | cattttatta | gtacatccat ttagggttta | 360 |
| gggttaatgg | tttttataga | ctaatttttt | tagtacatct | attttattct attttagcct | 420 |
| ctaaattaag | aaaactaaaa | ctctatttta | gtttttttat | ttaatagttt agatataaaa | 480 |
| tagaataaaa | taaagtgact | aaaaattaaa | caaatacccT | ttaagaaatt aaaaaaacta | 540 |
| aggaaacatt | tttcttgttt | cgagtagata | atgccagcct | gttaaacgcc gtcgacgagt | 600 |
| ctaacggaca | ccaaccagcg | aaccagcagc | gtcgcgtcgg | ccaagcgaa gcagacggca | 660 |
| cggcatctct | gtcgctgcct | ctggacccct | cgagagtt | ccgctccacc gttggacttg | 720 |
| ctccgctgtc | ggcatccaga | aattgcgtgg | cggagcggca | gacgtgagcc ggcacggcag | 780 |
| gcggcctcct | cctcctctca | cggcaccggc | agctacgggg | gattcctttc ccaccgctcc | 840 |
| ttcgctttcc | cttcctcgcc | cgccgtaata | aatagacacc | cctccacac cctctttccc | 900 |
| caacctcgtg | ttgttcggag | cgcacacaca | caaccagA | tctcccccaa atccacccgt | 960 |
| cggcacctcc | gcttcaaggg | taccctgaag | gctcgacaag | gcagtccacg gaggagctga | 1020 |
| tatttggtgg | acaagctgtg | gataggagca | accctatccc | taatatacca gcaccaccaa | 1080 |
| gtcagggcaa | tccccagatc | accccagcag | attcgaagaa | ggtacagtac acacacatgt | 1140 |
| atatatgtat | gatgtatccc | ttcgatcgaa | ggcatgcctt | ggtataatca ctgagtagtc | 1200 |
| attttattac | tttgttttga | caagtcagta | gttcatccat | ttgtcccatt tttcagctt | 1260 |
| ggaagtttgg | ttgcactggc | acttggtcta | ataactgagt | agtcatttta ttacgttgtt | 1320 |
| tcgacaagtc | agtagctcat | ccatctgtcc | catttttca | gctaggaagt ttggttgcac | 1380 |
| tggccttgga | ctaataactg | attagtcatt | ttattacatt | gtttcgacaa gtcagtagct | 1440 |
| catccatctg | tcccattttt | cagctaggaa | gttcggatct | ggggccattt gttccaggca | 1500 |
| cgggataagc | attcagccat | ggctaatgag | tcagtcaagg | atcccgga tgttctcaaa | 1560 |
| tcccagtgtg | gtttcaactg | cctcacggac | atctcccaca | gctcattcaa tgagttccgc | 1620 |
| cagcaagtct | ctgagcacct | ctcatggtcg | gagacgcatg | acctctacca cgatgctcag | 1680 |
| caagcccaga | aagacaaccg | gctgtatgag | gcacggatcc | tcaagagggc caacccgcag | 1740 |
| ctccagaatg | cggtccacct | cgccatcctt | gctccaaatg | cggaattgat tggctacaat | 1800 |
| aaccaattct | cggaagggc | ctcacagtat | gttgcgcctg | gcacagtttc gtccatgttc | 1860 |
| agcccagcag | cgtacctcac | agagctgtac | agagaggcga | ggaaccttca tgcgtctgac | 1920 |
| tccgtgtact | atctggacac | acgcagaccg | gacctgaagt | caatggccct cagccagcaa | 1980 |
| aacatggaca | ttgaactgtc | cacccttttcc | ttgagcaatg | agcttctgtt ggaatccatc | 2040 |
| aagactgaga | gcaagctgga | aaactacaca | aaggtgatgg | agatgctgtc caccttcaga | 2100 |

```
ccatctggag cgactccata ccacgatgcc tatgagaatg tgagggaggt cattcagctt    2160
caagaccctg gccttgagca gctcaatgcc agcccagcca ttgcgggact gatgcaccaa    2220
gcctccctgc ttgggatcaa tgcctccatc agccctgagc tgttcaacat cttgactgaa    2280
gagatcactg agggcaatgc ggaggaactg tacaagaaaa acttcggcaa cattgagcct    2340
gccagccttg caatgccgga atacctgaaa cgctattaca acttgtcgga tgaggaactt    2400
tcgcagttca ttggcaaagc ctcaaacttt gggcagcaag agtacagcaa caatcagctc    2460
atcacacctg ttgtgaactc atctgatggc actgtgaagg tttaccgcat cacaagggag    2520
tacaccacaa atgcctacca gatggatgtt gaactgttcc cgtttggagg tgaaaaactac   2580 cggcttgact acaagttcaa gaacttctac aatgcatcct acctgtcgat caagctgaac    2640
gacaaacggg agcttgtgag gacggaaggt gctccccaag tgaacattga atactctgcc    2700
aacatcacac tcaacacagc ggacatcagc cagccgtttg aaattggctt gaccagagtg    2760
cttccctcgg gctcctgggc ctatgcggca gccaagttta cggttgagga gtacaaccag    2820
tacagcttcc tcctgaagct caacaaggca atccggctga gcagagccac tgagctgtca    2880
cccaccatcc tggagggcat tgtgaggtct gtcaaccttc agcttgacat caacactgat    2940
gtgcttggca aggtgttcct gaccaagtat tacatgcagc gctatgccat ccatgcggag    3000
acggcactga tcctctgcaa tgcacccata tcgcagcgct cgtatgacaa ccagcccagc    3060
cagttcgaca gactcttcaa cactcccctt ctgaacggcc agtacttcag cactggagat    3120
gaagagattg acctgaactc tggctcgacg ggtgactgga ggaaaaccat cttgaagagg    3180
gccttcaaca ttgatgacgt ttccctcttc cgccttttga agatcacaga tcacgacaac    3240
aaggatggca agatcaagaa caatctcaag aacctttcca acctctacat tggcaaactg    3300
cttgcagaca tccaccagct gaccattgat gagttggacc tgttgctgat tgcagttggt    3360
gagggcaaga ccaacctctc tgcaatctca gacaaacagt tggcaaccct catccgcaag    3420
ctgaacacga tcacaagctg gcttcacacg cagaagtggt ctgttttcca actgttcatc    3480
atgaccagca cgtcctacaa caagaccctg actccggaga tcaagaacct tttggataca    3540
gtctatcatg tctccaagg cttttgacaag gacaaggcgg acctgcttca tgtcatggca    3600
ccctacattg cagccacact ccagctctcc tctgaaaatg ttgcccactc agtgctgttg    3660
tgggctgaca gctccagcc tggggatgga gccatgactg ctgagaagtt ctgggactgg    3720
ctcaacacga agtacacacc tggctcctct gaggcagttg agactcaaga acacattgtg    3780
cagtactgcc aagcgcttgc acagttggag atggtttacc actcaactgg catcaacgag    3840
aatgccttcc gcctctttgt cacaaagcct gagatgtttg gtgctgccac tggagccgct    3900
cctgcccatg atgccctgtc actcatcatg ttgacgaggt ttgcagactg ggtcaacgcc    3960
cttggtgaga agcctcgtc tgtcctggca gcctttgaag ccaactccct gactgcggaa    4020
cagcttgcgg atgccatgaa ccttgatgcc aacttgctcc tgcaagcttc gatccaagcc    4080
cagaaccatc agcatttgcc acctgtcacg cctgaaaatg cgttctcatg ctggacctcc    4140
atcaacacca tactccagtg ggtgaacgtg gcgcaacagc tcaatgtggc acctcaagga    4200
gtgtcagcgc tggttgggct tgactacatc agtccatga aggagacacc gacctacgcg    4260
cagtgggaga atgcagctgg cgtcttgaca gctggtctga actcacagca agccaacacg    4320
ctgcatgcgt tcttggatga gagccgctct gctgccctca gcacgtacta tatccggcaa    4380
gttgccaagg cagcggctgc catcaagtct cgggatgacc tctaccagta cttgctcatt    4440
gacaatcagg tttctgctgc catcaaaacg acccggattg ctgaggccat agccagcatc    4500
```

```
cagctctacg tcaacagagc gcttgagaac gttgaagaga atgccaactc tggagtgatt    4560
tctcgccagt ttttcataga ctgggacaag tacaacaagc gctactccac ctgggctggg    4620
gtctctcagc ttgtctacta tcctgagaac tacatagatc cgacgatgcg gattggccag    4680
accaagatga tggatgccct ccttcagtcg gtgtcccaga gccagctcaa tgctgacact    4740
gtggaggatg ccttcatgag ctacctcacc tccttcgagc aagttgccaa cctcaaggtc    4800
atctctgctt accacgacaa catcaacaat gaccaagggc tcacctactt cattggcctg    4860
tctgaaactg atgcgggtga gtattactgg cgctcagtgg accacagcaa gttcaacgat    4920
ggcaagtttg ctgcaaatgc ctggtctgag tggcacaaga ttgactgccc catcaacccg    4980
tacaagtcca ccatcagacc tgtcatctac aagagccgct tgtacttgct ctggcttgag    5040
cagaaggaaa tcacgaagca gactggcaac tccaaagatg gctaccagac tgagacggac    5100
taccgctatg agttgaaact tgctcacatc cgctatgatg gtacatggaa cactccgata    5160
acgtttgatg tgaacaagaa gatttcggag ctgaaactgg agaagaacag agcgcctggg    5220
ctctactgtg ctggctacca aggggaagat acgctgttgg tgatgttcta caaccagcaa    5280
gacacccttg actcgtacaa gaacgcttcc atgcaaggcc tctacatctt tgctgacatg    5340
gcttccaaag acatgactcc ggagcagagc aatgtctacc gggacaactc ctaccagcaa    5400
tttgacacca acaatgttcg gagggtcaat aaccgctatg cggaagatta tgagatccca    5460
agctcagtgt ctagccgcaa ggactatggc tggggagact actatctcag catggtgtac    5520
aatggtgaca tacccacgat caactacaag gctgcctcct cagacctgaa gatatacatc    5580
agccccaagc tccgcatcat tcacaatggc tatgagggcc agaagaggaa ccagtgcaac    5640
ttgatgaaca gtatggcaa acttggggac aagttcattg tctacacctc gcttggtgtg    5700
aacccgaaca attcctcgaa caagctcatg ttctacccgg tctaccagta cagcggcaac    5760
acctctggct tgaaccaagg gaggctcctg ttccacagag acaccacgta cccgagcaag    5820
gtggaggcgt ggattcctgg tgccaaaagg tcactcacca accagaatgc agccattggt    5880
gatgactatg ccacagacag cctgaacaag cctgatgacc tgaagcagta catcttcatg    5940
actgactcca agggcacagc cactgatgtg tctggtccgg tggagatcaa cactgcaatc    6000
agcccagcca aggtccaaat cattgtcaaa gctggtggca aggaacagac cttcacagct    6060
gacaaagatg tgagcatcca gccaagcccc tcctttgatg agatgaacta ccagttcaac    6120
gctcttgaaa ttgatggctc gggactcaac ttcatcaaca attcggcttc aattgatgtg    6180
acgttcactg cctttgcgga ggatgggagg aaattgggct atgagagctt caatacca    6240 gtcaccttga aggtttccac tgacaatgca ctcacgcttc atcacaacga gaatggagcg    6300
cagtacatgc aatggcagag ctaccgcaca aggttgaaca ccctctttgc aaggcaactt    6360
gtggccagag ccacgactgg cattgacacc atactcagca tggaaacgca gaacatccaa    6420
gagccacagt tgggcaaggg tttctatgcc acctttgtga tcccacccta caacctgtca    6480
acgcatggtg atgagcgctg gttcaagctg tacatcaagc acgtggttga caacaattcc    6540
cacatcatat actcgggtca gctcactgac acgaacatca acatcaccct gttcatccca    6600
cttgatgacg ttcccctgaa ccaagactac catgccaagg tctacatgac cttcaagaaa    6660
tcaccgtcag atggcacctg gtggggaccg cacttcgttc gggatgacaa aggcattgtc    6720
acaatcaacc ccaagtccat actcacccac tttgagtctg tgaatgttct gaataacatc    6780
tcctcagagc cgatggactt ctcgggtgcc aactccctgt acttctggga gttgttctat    6840
tacacgccga tgcttgtggc gcagaggttg ctccatgaac agaactttga tgaggccaac    6900
```

```
cgctggctca agtatgtctg gagcccctcg ggttacattg tgcatggcca gatccagaac    6960
taccaatgga atgttcgccc attgcttgag gacacctcct ggaactctga ccccttgac    7020 tcggtggacc ctgatgcggt ggctcagcat gaccccatgc actacaaggt ctcaaccttc    7080
atgaggaccc tggaccttct gattgccaga ggagaccatg cttaccgcca attggaacgg    7140
gacacactga atgaggcaaa gatgtggtac atgcaagctc tgcacctctt gggagacaag    7200
ccgtacctcc cgctcagcac cacatggtca gacccaaggt tggacagagc agctgacatc    7260
acaactcaga atgctcatga ctctgccatt gtggctctga ggcagaacat cccaacacct    7320
gcgccactgt cgctgagatc tgcgaacacc ctgacagacc tgttcctccc ccagatcaat    7380
gaggtcatga tgaactactg gcaaaccttg gcgcagcggg tctacaacct ccgccacaac    7440
ctctccattg atgggcagcc gctgtacctc ccaatctatg ccacaccagc tgacccaaag    7500
gcgcttctca gcgcagctgt ggccacgagc caaggggag gcaagctccc tgagagcttc    7560
atgtcgctct ggaggtttcc ccacatgttg gagaatgcca gaggcatggt gagccaactg    7620
actcagtttg gctcgacgct ccagaacatc attgagaggc aagatgcaga ggctctgaat    7680
gcgttgctcc agaatcaagc agctgagttg atcctgacga acctgtcaat ccaagacaag    7740
accattgagg aacttgatgc ggaaaagaca gtccttgaaa agagcaaggc tggagcccaa    7800
agccggttcg actcatatgg caagctgtat gatgagaaca tcaatgctgg ggagaatcaa    7860
gccatgaccc tgagggcttc agcagcgggt ctgaccacgg cagtgcaagc gtctcgcttg    7920
gctggggctg cggctgacct cgttcccaac atctttgggt tgctggtgg cggatcaagg    7980 tggggagcca ttgcagaagc aacgggctat gtgatggagt tctctgccaa tgtcatgaac    8040
actgaggcag acaaaatcag ccaatcggag acctacagac ggagacggca gaatgggag    8100 atacaaagga acaatgcaga ggcagaactg aagcaaatag atgcccaact gaagtccttg    8160
gctgtcagaa gggaggctgc ggtcctccaa aagacctccc tcaagaccca gcaagagcaa    8220
acccagtccc agttggcgtt cctccagagg aagttctcga accaagcgct gtacaactgg    8280
ctgaggggaa ggttggcagc catctacttc cagttctatg accttgctgt ggccagatgc    8340 ctcatggcg aacaagccta ccgctgggaa ctgaatgatg actctgccag attcatcaaa    8400
ccgggtgcat ggcaaggcac atatgctgga ctccttgctg gggagacact catgctctca    8460
ttggcccaga tggaggatgc tcacctcaaa cgggacaaga gggctctgga agtgagcgg    8520 acagtcagcc ttgcggaggt ctatgcggga ctgcccaaag acaatggacc attttcgttg    8580
gcgcaagaga tagacaagtt ggtcagccaa gggtctggat cagcgggttc tggaaacaac    8640
aatctggcgt tcggtgctgg cactgacacc aagacgtccc tccaagcctc agtctccttt    8700
gctgacctga agataaggga ggactaccca gcgtcccttg ggaagatcag acgcatcaag    8760
cagatttcag tgaccctgcc agctcttctg gtccatacc aagatgttca agcgatcctc    8820
tcctatgggg acaaggctgg tttggcgaat ggctgtgagg cccttgctgt gtcacatggc    8880
atgaatgact ctgggcagtt ccagcttgat ttcaacgatg gcaagttcct gccattcgag    8940
ggcatagcca ttgatcaagg caccctgacc ctctccttcc ccaatgcttc gatgccagag    9000
aagggaaaac aagccaccat gctcaagacc ctgaatgata tcatactcca catccgctac    9060
accatcaagt gagtagttag cttaatcacc tagagctcgt ttaaactgag ggcactgaag    9120
tcgcttgatg tgctgaattg tttgtgatgt tggtggcgta ttttgtttaa ataagtaagc    9180
atggctgtga ttttatcata tgatcgatct ttggggtttt atttaacaca ttgtaaaatg    9240
tgtatctatt aataactcaa tgtataagat gtgttcattc ttcggttgcc atagatctgc    9300
```

```
ttatttgacc tgtgatgttt tgactccaaa aaccaaaatc acaactcaat aaactcatgg    9360
aatatgtcca cctgtttctt gaagagttca tctaccattc cagttggcat ttatcagtgt    9420
tgcagcggcg ctgtgctttg taacataaca attgttacgg catatatcca a             9471

<210> SEQ ID NO 7
<211> LENGTH: 1518
<212> TYPE: DNA
<213> ORGANISM: artificial sequence
<220> FEATURE:
<223> OTHER INFORMATION: The novel Zea mays Ubiquitin 1 promoter
      followed by the Zea mays alcohol dehydrogenase (I) intron 6 and
      Maize Streak Virus 5' -UTR

<400> SEQUENCE: 7
gtgcagcgtg acccggtcgt gcccctctct agagataatg agcattgcat gtctaagtta      60
taaaaaatta ccacatattt ttttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc tttttttttg    300
caaatagctt cacctatata atacttcatc cattttatta gtacatccat ttagggttta    360
gggttaatgg ttttttataga ctaatttttt tagtacatct attttattct attttagcct    420
ctaaattaag aaaactaaaa ctctatttta gttttttttat ttaatagttt agatataaaa    480
tagaataaaa taaagtgact aaaaattaaa caaataccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840 ttcgcttttcc cttcctcgcc cgccgtaata aatagacacc cctccacac cctctttccc    900 caacctcgtg ttgttcggag cgcacacaca caaccagga tctcccccaa atccaccccgt    960 cggcacctcc gcttcaaggg taccctgaag gctcgacaag gcagtccacg gaggagctga   1020
tatttggtgg acaagctgtg gataggagca accctatccc taatatacca gcaccaccaa   1080
gtcagggcaa tccccagatc accccagcag attcgaagaa ggtacagtac acacacatgt   1140
atatatgtat gatgtatccc ttcgatcgaa ggcatgcctt ggtataatca ctgagtagtc   1200
attttattac tttgttttga caagtcagta gttcatccat ttgtcccatt ttttcagctt   1260
ggaagtttgg ttgcactggc acttggtcta ataactgagt agtcattta ttacgttgtt   1320 tcgacaagtc agtagctcat ccatctgtcc cattttttca gctaggaagt ttggttgcac   1380
tggccttgga ctaataactg attagtcatt ttattacatt gtttcgacaa gtcagtagct   1440
catccatctg tcccattttt cagctaggaa gttcggatct ggggccatt gttccaggca   1500 cgggataagc attcagcc                                                 1518

<210> SEQ ID NO 8
<211> LENGTH: 9950
<212> TYPE: DNA
<213> ORGANISM: artificial sequence
<220> FEATURE:
<223> OTHER INFORMATION: pDAB3924 first gene expression cassette
```

```
<400> SEQUENCE: 8
atcggaagtt gaagacaaag aaggtcttaa atcctggcta gcaacactga actatgccag      60
aaaccacatc aaagatatcg gcaagcttct tggcccatta tatccaaaga cctcagagaa     120
aggtgagcga aggctcaatt cagaagattg gaagctgatc aataggatca agacaatggt     180
gagaacgctt ccaaatctca ctattccacc agaagatgca tacattatca ttgaaacaga     240
tgcatgtgca actggatggg gagcagtatg caagtggaag aaaaacaagg cagacccaag     300
aaatacagag caaatctgta ggtatgccag tggaaaattt gataagccaa aaggaacctg     360
tgatgcagaa atctatgggg ttatgaatgg cttagaaaag atgagattgt tctacttgga     420
caaaagagag atcacagtca gaactgacag tagtgcaatc gaaaggttct acaacaagag     480
tgctgaacac aagccttctg agatcagatg gatcaggttc atggactaca tcactggtgc     540
aggaccagag atagtcattg aacacataaa agggaagagc aatggtttag ctgacatctt     600
gtccaggctc aaagccaaat tagctcagaa tgaaccaacg gaagagatga tcctgcttac     660
acaagccata agggaagtaa ttccttatcc agatcatcca tacactgagc aactcagaga     720
atggggaaac aaaattctgg atccattccc cacattcaag aaggacatgt tcgaaagaac     780
agagcaagct tttatgctaa cagaggaacc agttctactc tgtgcatgca ggaagcctgc     840
aattcagtta gtgtccagaa catctgccaa cccaggaagg aaattcttca agtgcgcaat     900
gaacaaatgc cattgctggt actgggcaga tctcattgaa gaacacattc aagacagaat     960
tgatgaattt ctcaagaatc ttgaagttct gaagaccggt ggcgtgcaaa caatggagga    1020
ggaacttatg aaggaagtca ccaagctgaa gatagaagag caggagttcg aggaatacca    1080
ggccacacca agggctatgt cgccagtagc cgcagaagat gtgctagatc tccaagacgt    1140
aagcaatgac gattgaggag gcattgacgt cagggatgac cgcagcggag agtactgggc    1200
ccattcagtg gatgctccac tgagttgtat tattgtgtgc ttttcggaca agtgtgctgt    1260
ccactttctt ttggcacctg tgccacttta ttccttgtct gccacgatgc ctttgcttag    1320
cttgtaagca aggatcgcag tgcgtgtgtg acaccacccc ccttccgacg ctctgcctat    1380
ataaggcacc gtctgtaagc tcttacgatc atcggtagtt caccaaggta cccgggtcg    1440 acctcgaggg ggggcccggt accctgaagg ctcgacaagg cagtccacgg aggagctgat    1500
atttggtgga caagctgtgg ataggagcaa ccctatccct aatataccag caccaccaag    1560
tcagggcaat ccccagatca ccccagcaga ttcgaagaag gtacagtaca cacacatgta    1620
tatatgtatg atgtatccct tcgatcgaag gcatgccttg gtataatcac tgagtagtca    1680
ttttattact ttgttttgac aagtcagtag ttcatccatt tgtcccattt tttcagcttg    1740
gaagtttggt tgcactggca cttggtctaa taactgagta gtcattttat tacgttgttt    1800
cgacaagtca gtagctcatc catctgtccc atttttttcag ctaggaagtt tggttgcact    1860
ggccttggac taataactga ttagtcattt tattacattg tttcgacaag tcagtagctc    1920
atccatctgt cccattttt c agctaggaag ttcggatctg gggccatttg ttccaggcac    1980
gggataagca ttcagccatg gctaatgagt cagtcaagga gatcccggat gttctcaaat    2040
cccagtgtgg tttcaactgc ctcacggaca tctcccacag ctcattcaat gagttccgcc    2100
agcaagtctc tgagcacctc tcatggtcgg agacgcatga cctctaccac gatgctcagc    2160
aagcccagaa agacaaccgg ctgtatgagg cacggatcct caagagggcc aaccccgcagc    2220 tccagaatgc ggtccacctc gccatccttg ctccaaatgc ggaattgatt ggctacaata    2280
accaattctc gggaagggcc tcacagtatg ttgcgcctgg cacagtttcg tccatgttca    2340
```

```
gcccagcagc gtacctcaca gagctgtaca gagaggcgag gaaccttcat gcgtctgact   2400
ccgtgtacta tctggacaca cgcagaccgg acctgaagtc aatggccctc agccagcaaa   2460
acatggacat tgaactgtcc acccttcct tgagcaatga gcttctgttg gaatccatca    2520
agactgagag caagctggaa aactacacaa aggtgatgga gatgctgtcc accttcagac   2580
catctggagc gactccatac cacgatgcct atgagaatgt gagggaggtc attcagcttc   2640
aagaccctgg ccttgagcag ctcaatgcca gcccagccat tgcgggactg atgcaccaag   2700
cctccctgct tgggatcaat gcctccatca gccctgagct gttcaacatc ttgactgaag   2760
agatcactga gggcaatgcg gaggaactgt acaagaaaaa cttcggcaac attgagcctg   2820
ccagccttgc aatgccggaa tacctgaaac gctattacaa cttgtcggat gaggaacttt   2880
cgcagttcat tggcaaagcc tcaaactttg ggcagcaaga gtacagcaac aatcagctca   2940
tcacacctgt tgtgaactca tctgatggca ctgtgaaggt ttaccgcatc acaagggagt   3000
acaccacaaa tgcctaccag atggatgttg aactgttccc gtttggaggt gaaaactacc   3060
ggcttgacta caagttcaag aacttctaca atgcatccta cctgtcgatc aagctgaacg   3120
acaaacggga gcttgtgagg acggaaggtg ctccccaagt gaacattgaa tactctgcca   3180
acatcacact caacacagcg gacatcagcc agccgtttga aattggcttg accagagtgc   3240
ttccctcggg ctcctgggcc tatgcggcag ccaagtttac ggttgaggag tacaaccagt   3300
acagcttcct cctgaagctc aacaaggcaa tccggctgag cagagccact gagctgtcac   3360
ccaccatcct ggagggcatt gtgaggtctg tcaaccttca gcttgacatc aacactgatg   3420
tgcttggcaa ggtgttcctg accaagtatt acatgcagcg ctatgccatc catgcggaga   3480
cggcactgat cctctgcaat gcacccatat cgcagcgctc gtatgacaac cagcccagcc   3540
agttcgacag actcttcaac actcccttc tgaacggcca gtacttcagc actggagatg    3600
aagagattga cctgaactct ggctcgacgg gtgactggag gaaaaccatc ttgaagaggg   3660
ccttcaacat tgatgacgtt tccctcttcc gccttttgaa gatcacagat cacgacaaca   3720
aggatggcaa gatcaagaac aatctcaaga acctttccaa cctctacatt ggcaaactgc   3780
ttgcagacat ccaccagctg accattgatg agttggacct gttgctgatt gcagttggtg   3840
agggcaagac caacctctct gcaatctcag acaaacagtt ggcaaccctc atccgcaagc   3900
tgaacacgat cacaagctgg cttcacacgc agaagtggtc tgttttccaa ctgttcatca   3960
tgaccagcac gtcctacaac aagaccctga ctccggagat caagaacctt ttggatacag   4020
tctatcatgg tctccaaggc tttgacaagg acaaggcgga cctgcttcat gtcatggcac   4080
cctacattgc agccacactc cagctctcct ctgaaaatgt tgcccactca gtgctgttgt   4140
gggctgacaa gctccagcct ggggatggag ccatgactgc tgagaagttc tgggactggc   4200
tcaacacgaa gtacacacct ggctcctctg aggcagttga gactcaagaa cacattgtgc   4260
agtactgcca agcgcttgca cagttggaga tggtttacca ctcaactggc atcaacgaga   4320
atgccttccg cctctttgtc acaaagcctg agatgtttgg tgctgccact ggagccgctc   4380
ctgcccatga tgccctgtca ctcatcatgt tgacgaggtt tgcagactgg gtcaacgccc   4440
ttggtgagaa agcctcgtct gtcctggcag ccttttgaagc caactccctg actgcggaac   4500
agcttgcgga tgccatgaac cttgatgcca acttgctcct gcaagcttcg atccaagccc   4560
agaaccatca gcatttgcca cctgtcacgc ctgaaaatgc gttctcatgc tggacctcca   4620
tcaacaccat actccagtgg gtgaacgtgg cgcaacagc caatgtggca cctcaaggag   4680
tgtcagcgct ggttgggctt gactacatcc agtccatgaa ggagacaccg acctacgcgc   4740
```

-continued

| | |
|---|---|
| agtgggagaa tgcagctggc gtcttgacag ctggtctgaa ctcacagcaa gccaacacgc | 4800 |
| tgcatgcgtt cttggatgag agccgctctg ctgccctcag cacgtactat atccggcaag | 4860 |
| ttgccaaggc agcggctgcc atcaagtctc gggatgacct ctaccagtac ttgctcattg | 4920 |
| acaatcaggt ttctgctgcc atcaaaacga cccggattgc tgaggccata gccagcatcc | 4980 |
| agctctacgt caacagagcg cttgagaacg ttgaagagaa tgccaactct ggagtgattt | 5040 |
| ctcgccagtt tttcatagac tgggacaagt acaacaagcg ctactccacc tgggctgggg | 5100 |
| tctctcagct tgtctactat cctgagaact acatagatcc gacgatgcgg attggccaga | 5160 |
| ccaagatgat ggatgccctc cttcagtcgg tgtcccagag ccagctcaat gctgacactg | 5220 |
| tggaggatgc cttcatgagc tacctcacct ccttcgagca agttgccaac ctcaaggtca | 5280 |
| tctctgctta ccacgacaac atcaacaatg accaagggct cacctacttc attggcctgt | 5340 |
| ctgaaactga tgcgggtgag tattactggc gctcagtgga ccacagcaag ttcaacgatg | 5400 |
| gcaagtttgc tgcaaatgcc tggtctgagt ggcacaagat tgactgcccc atcaacccgt | 5460 |
| acaagtccac catcagacct gtcatctaca agagccgctt gtacttgctc tggcttgagc | 5520 |
| agaaggaaat cacgaagcag actggcaact ccaaagatgg ctaccagact gagacggact | 5580 |
| accgctatga gttgaaactt gctcacatcc gctatgatgg tacatggaac actccgataa | 5640 |
| cgtttgatgt gaacaagaag atttcggagc tgaaactgga gaagaacaga gcgcctgggc | 5700 |
| tctactgtgc tggctaccaa ggggaagata cgctgttggt gatgttctac aaccagcaag | 5760 |
| acacccttga ctcgtacaag aacgcttcca tgcaaggcct ctacatcttt gctgacatgg | 5820 |
| cttccaaaga catgactccg gagcagagca atgtctaccg ggacaactcc taccagcaat | 5880 |
| ttgacaccaa caatgttcgg agggtcaata accgctatgc ggaagattat gagatcccaa | 5940 |
| gctcagtgtc tagccgcaag gactatggct ggggagacta ctatctcagc atggtgtaca | 6000 |
| atggtgacat acccacgatc aactacaagg ctgcctcctc agacctgaag atatacatca | 6060 |
| gccccaagct ccgcatcatt cacaatggct atgagggcca agagaggaac cagtgcaact | 6120 |
| tgatgaacaa gtatggcaaa cttggggaca agttcattgt ctacacctcg cttggtgtga | 6180 |
| acccgaacaa ttcctcgaac aagctcatgt tctacccggt ctaccagtac agcggcaaca | 6240 |
| cctctggctt gaaccaaggg aggctcctgt tccacagaga caccacgtac ccgagcaagg | 6300 |
| tggaggcgtg gattcctggt gccaaaaggt cactcaccaa ccagaatgca gccattggtg | 6360 |
| atgactatgc cacagacagc ctgaacaagc ctgatgacct gaagcagtac atcttcatga | 6420 |
| ctgactccaa gggcacagcc actgatgtgt ctggtccggt ggagatcaac actgcaatca | 6480 |
| gcccagccaa ggtccaaatc attgtcaaag ctggtggcaa ggaacagacc ttcacagctg | 6540 |
| acaaagatgt gagcatccag ccaagcccct cctttgatga gatgaactac cagttcaacg | 6600 |
| ctcttgaaat tgatggctcg ggactcaact tcatcaacaa ttcggcttca attgatgtga | 6660 |
| cgttcactgc ctttgcggag gatgggagga aattgggcta tgagagcttc tcaataccag | 6720 |
| tcaccttgaa ggtttccact gacaatgcac tcacgcttca tcacaacgag aatggagcgc | 6780 |
| agtacatgca atggcagagc taccgcacaa ggttgaacac cctctttgca aggcaacttg | 6840 |
| tggcagagc cacgactggc attgacacca tactcagcat ggaaacgcag aacatccaag | 6900 |
| agccacagtt gggcaagggt ttctatgcca cctttgtgat cccacccta aacctgtcaa | 6960 |
| cgcatggtga tgagcgctgg ttcaagctgt acatcaagca cgtggttgac aacaattccc | 7020 |
| acatcatata ctcgggtcag ctcactgaca cgaacatcaa catcacccrg ttcatcccac | 7080 |
| ttgatgacgt tcccctgaac caagactacc atgccaaggt ctacatgacc ttcaagaaat | 7140 |

```
caccgtcaga tggcacctgg tggggaccgc acttcgttcg ggatgacaaa ggcattgtca    7200
caatcaaccc caagtccata ctcacccact ttgagtctgt gaatgttctg aataacatct    7260
cctcagagcc gatggacttc tcgggtgcca actccctgta cttctgggag ttgttctatt    7320
acacgccgat gcttgtggcg cagaggttgc tccatgaaca gaactttgat gaggccaacc    7380
gctggctcaa gtatgtctgg agcccctcgg gttacattgt gcatggccag atccagaact    7440
accaatggaa tgttcgccca ttgcttgagg acacctcctg gaactctgac ccccttgact    7500
cggtggaccc tgatgcggtg gctcagcatg accccatgca ctacaaggtc tcaaccttca    7560
tgaggaccct ggaccttctg attgccgaga gagaccatgc ttaccgccaa ttggaacggg    7620
acacactgaa tgaggcaaag atgtggtaca tgcaagctct gcacctcttg ggagacaagc    7680
cgtacctccc gctcagcacc acatggtcag acccaaggtt ggacagagca gctgacatca    7740
caactcagaa tgctcatgac tctgccattg tggctctgag gcagaacatc ccaacacctg    7800
cgccactgtc gctgagatct gcgaacaccc tgacagacct gttcctcccc cagatcaatg    7860
aggtcatgat gaactactgg caaaccttgg cgcagcgggt ctacaacctc cgccacaacc    7920
tctccattga tgggcagccg ctgtacctcc caatctatgc cacaccagct gacccaaagg    7980
cgcttctcag cgcagctgtg gccacagagcc aaggggagg caagctccct gagagcttca    8040
tgtcgctctg gaggtttccc cacatgttgg agaatgccag aggcatggtg agccaactga    8100
ctcagtttgg ctcgacgctc cagaacatca ttgagaggca agatgcagag gctctgaatg    8160
cgttgctcca gaatcaagca gctgagttga tcctgacgaa cctgtcaatc caagacaaga    8220
ccattgagga acttgatgcg gaaaagacag tccttgaaaa agcaaggct ggagcccaaa    8280
gccggttcga ctcatatggc aagctgtatg atgagaacat caatgctggg gagaatcaag    8340
ccatgaccct gagggcttca gcagcgggtc tgaccacggc agtgcaagcg tctcgcttgg    8400
ctggggctgc ggctgacctc gttcccaaca tctttgggtt tgctggtggc ggatcaaggt    8460
ggggagccat tgcagaagca acgggctatg tgatggagtt ctctgccaat gtcatgaaca    8520
ctgaggcaga caaaatcagc caatcggaga cctacagacg gagacggcaa gaatgggaga    8580
tacaaaggaa caatgcagag gcagaactga agcaaataga tgcccaactg aagtccttgg    8640
ctgtcagaag ggaggctgcg gtcctccaaa agacctccct caagacccag caagagcaaa    8700
cccagtccca gttggcgttc ctccagagga agttctcgaa ccaagcgctg tacaactggc    8760
tgaggggaag gttggcagcc atctacttcc agttctatga ccttgctgtg gccagatgcc    8820
tcatggcgga acaagcctac cgctgggaac tgaatgatga ctctgccaga ttcatcaaac    8880
cgggtgcatg gcaaggcaca tatgctggac tccttgctgg ggagacactc atgctctcat    8940
tggcccagat ggaggatgct cacctcaaac gggacaagag ggctctggaa gtggagcgga    9000
cagtcagcct tgcggaggtc tatgcgggac tgcccaaaga caatggacca ttttcgttgg    9060
cgcaagagat agacaagttg gtcagccaag ggtctggatc agcgggttct ggaaacaaca    9120
atctggcgtt cggtgctggc actgacacca agacgtccct ccaagcctca gtctcctttg    9180
ctgacctgaa gataagggag gactacccag cgtcccttgg gaagatcaga cgcatcaagc    9240
agatttcagt gaccctgcca gctccttctg gtccatacca agatgttcaa gcgatcctct    9300
cctatgggga caaggctggt ttggcgaatg gctgtgaggc ccttgctgtg tcacatggca    9360
tgaatgactc tgggcagttc cagcttgatt tcaacgatgg caagttcctg ccattcgagg    9420
gcatagccat tgatcaaggc accctgaccc tctccttccc caatgcttcg atgccagaga    9480
agggaaaaca agccaccatg ctcaagaccc tgaatgatat catactccac atccgctaca    9540
```

| | |
|---|---|
| ccatcaagtg agtagttagc ttaatcacct agagctcgtt taaactgagg gcactgaagt | 9600 |
| cgcttgatgt gctgaattgt ttgtgatgtt ggtggcgtat tttgtttaaa taagtaagca | 9660 |
| tggctgtgat tttatcatat gatcgatctt tggggtttta tttaacacat tgtaaaatgt | 9720 |
| gtatctatta ataactcaat gtataagatg tgttcattct tcggttgcca tagatctgct | 9780 |
| tatttgacct gtgatgtttt gactccaaaa accaaaatca caactcaata aactcatgga | 9840 |
| atatgtccac ctgtttcttg aagagttcat ctaccattcc agttggcatt tatcagtgtt | 9900 |
| gcagcggcgc tgtgctttgt aacataacaa ttgttacggc atatatccaa | 9950 |

<210> SEQ ID NO 9
<211> LENGTH: 1997
<212> TYPE: DNA
<213> ORGANISM: artificial sequence
<220> FEATURE:
<223> OTHER INFORMATION: The novel Sugar Cane Bacilliform Virus promoter
followed by the Zea mays alcohol dehydrogenase (I) intron 6 and
Maize Streak Virus 5'-UTR

<400> SEQUENCE: 9

| | |
|---|---|
| atcggaagtt gaagacaaag aaggtcttaa atcctggcta gcaacactga actatgccag | 60 |
| aaaccacatc aaagatatcg gcaagcttct tggcccatta tatccaaaga cctcagagaa | 120 |
| aggtgagcga aggctcaatt cagaagattg gaagctgatc aataggatca agacaatggt | 180 |
| gagaacgctt ccaaatctca ctattccacc agaaagatgca tacattatca ttgaaacaga | 240 |
| tgcatgtgca actggatggg gagcagtatg caagtggaag aaaaacaagg cagacccaag | 300 |
| aaatacagag caaatctgta ggtatgccag tggaaaattt gataagccaa aggaacctg | 360 |
| tgatgcagaa atctatgggg ttatgaatgg cttagaaaag atgagattgt tctacttgga | 420 |
| caaaagagag atcacagtca gaactgacag tagtgcaatc gaaaggttct acaacaagag | 480 |
| tgctgaacac aagccttctg agatcagatg gatcaggttc atggactaca tcactggtgc | 540 |
| aggaccagag atagtcattg aacacataaa agggaagagc aatggtttag ctgacatctt | 600 |
| gtccaggctc aaagccaaat tagctcagaa tgaaccaacg gaagagatga tcctgcttac | 660 |
| acaagccata agggaagtaa ttccttatcc agatcatcca tacactgagc aactcagaga | 720 |
| atggggaaac aaaattctgg atccattccc cacattcaag aaggacatgt tcgaaagaac | 780 |
| agagcaagct tttatgctaa cagaggaacc agttctactc tgtgcatgca ggaagcctgc | 840 |
| aattcagtta gtgtccagaa catctgccaa cccaggaagg aaattcttca gtgcgcaat | 900 |
| gaacaaatgc cattgctggt actgggcaga tctcattgaa gaacacattc aagacagaat | 960 |
| tgatgaattt ctcaagaatc ttgaagttct gaagaccggt ggcgtgcaaa caatggagga | 1020 |
| ggaacttatg aaggaagtca ccaagctgaa gatagaagag caggagttcg aggaatacca | 1080 |
| ggccacacca agggctatgt cgccagtagc cgcagaagat gtgctagatc tccaagacgt | 1140 |
| aagcaatgac gattgaggag gcattgacgt cagggatgac cgcagcggag agtactgggc | 1200 |
| ccattcagtg gatgctccac tgagttgtat tattgtgtgc ttttcggaca agtgtgctgt | 1260 |
| ccactttctt ttggcaccctg tgccacttta ttccttgtct gccacgatgc ctttgcttag | 1320 |
| cttgtaagca aggatcgcag tgcgtgtgtg acaccacccc ccttccgacg ctctgcctat | 1380 |
| ataaggcacc gtctgtaagc tcttacgatc atcggtagtt caccaaggta cccggggtcg | 1440 |
| acctcgaggg ggggcccggt accctgaagg ctcgacaagg cagtccacgg aggagctgat | 1500 |
| atttggtgga caagctgtgg ataggagcaa ccctatccct aatataccag caccaccaag | 1560 |
| tcagggcaat ccccagatca ccccagcaga ttcgaagaag gtacagtaca cacacatgta | 1620 |

```
tatatgtatg atgtatccct tcgatcgaag gcatgccttg gtataatcac tgagtagtca  1680
ttttattact ttgttttgac aagtcagtag ttcatccatt tgtcccattt tttcagcttg  1740
gaagtttggt tgcactggca cttggtctaa taactgagta gtcattttat tacgttgttt  1800
cgacaagtca gtagctcatc catctgtccc atttttttcag ctaggaagtt tggttgcact  1860
ggccttggac taataactga ttagtcattt tattacattg tttcgacaag tcagtagctc  1920
atccatctgt cccatttttc agctaggaag ttcggatctg gggccatttg ttccaggcac  1980
gggataagca ttcagcc                                                 1997
```